(12) United States Patent
Stockley et al.

(10) Patent No.: US 10,927,110 B2
(45) Date of Patent: Feb. 23, 2021

(54) CYANO-SUBTITUTED HETEROCYCLES WITH ACTIVITY AS INHIBITORS OF USP30

(71) Applicant: MISSION THERAPEUTICS LIMITED, Cambridge (GB)

(72) Inventors: Martin Lee Stockley, Cambridge (GB); Mark Ian Kemp, Cambridge (GB)

(73) Assignee: MISSION THERAPEUTICS LIMITED, Cambridge (GB)

(*) Notice: Subject to any disclaimer, the term of this patent is extended or adjusted under 35 U.S.C. 154(b) by 0 days.

(21) Appl. No.: 16/336,363

(22) PCT Filed: Sep. 27, 2017

(86) PCT No.: PCT/GB2017/052882
§ 371 (c)(1),
(2) Date: Mar. 25, 2019

(87) PCT Pub. No.: WO2018/060691
PCT Pub. Date: Apr. 5, 2018

(65) Prior Publication Data
US 2019/0218215 A1    Jul. 18, 2019

(30) Foreign Application Priority Data
Sep. 29, 2016 (GB) ................................. 1616511

(51) Int. Cl.
| | | |
|---|---|---|
| *A61P 3/00* | (2006.01) | |
| *A61P 43/00* | (2006.01) | |
| *A61P 35/00* | (2006.01) | |
| *A61P 25/00* | (2006.01) | |
| *A61P 9/00* | (2006.01) | |
| *C07D 471/04* | (2006.01) | |
| *C07D 471/14* | (2006.01) | |
| *C07D 401/04* | (2006.01) | |
| *C07D 401/14* | (2006.01) | |
| *C07D 413/14* | (2006.01) | |
| *C07D 413/04* | (2006.01) | |
| *C07D 498/04* | (2006.01) | |

(52) U.S. Cl.
CPC ......... *C07D 471/04* (2013.01); *C07D 401/04* (2013.01); *C07D 401/14* (2013.01); *C07D 413/04* (2013.01); *C07D 413/14* (2013.01); *C07D 471/14* (2013.01); *C07D 498/04* (2013.01)

(58) Field of Classification Search
CPC .. A61P 3/00; A61P 43/00; A61P 35/00; A61P 25/00; A61P 9/00; C07D 471/04; C07D 471/14; C07D 401/04; C07D 401/14; C07D 413/04; C07D 413/14; C07D 498/04
See application file for complete search history.

(56) References Cited

U.S. PATENT DOCUMENTS

2008/0300268 A1    12/2008  Singh et al.

FOREIGN PATENT DOCUMENTS

| | | |
|---|---|---|
| WO | 9508534 A1 | 3/1995 |
| WO | 0177073 A1 | 10/2001 |
| WO | 2009026197 A1 | 2/2009 |
| WO | 2009129365 A1 | 10/2009 |
| WO | 2009129370 A1 | 10/2009 |
| WO | 2009129371 A1 | 10/2009 |
| WO | 2013030218 A1 | 3/2013 |
| WO | 2013064445 A1 | 5/2013 |
| WO | 2014068527 A1 | 5/2014 |
| WO | 2014188173 A1 | 11/2014 |
| WO | 2015017502 A1 | 2/2015 |
| WO | 2015061247 A2 | 4/2015 |
| WO | 2015157955 A1 | 10/2015 |
| WO | 2015158283 A1 | 10/2015 |
| WO | 2015165279 A1 | 11/2015 |
| WO | 2015179190 A1 | 11/2015 |
| WO | 2016019237 A2 | 2/2016 |
| WO | 2016/046530 A1 | 3/2016 |
| WO | 2016065226 A1 | 4/2016 |
| WO | 2016156816 A1 | 10/2016 |
| WO | 2016192074 A1 | 12/2016 |
| WO | 2017/009650 A1 | 1/2017 |
| WO | 2017/093718 A1 | 6/2017 |
| WO | 2017/109488 A1 | 6/2017 |
| WO | 2017103614 A1 | 6/2017 |

(Continued)

OTHER PUBLICATIONS

Caplus an 2017:844788 (2017).*
Ahmad et al., caplus an 2016:681766 (2016).*
CancerPrevention, 2020, https://www.health.harvard.edu/newsletter_article/the-10-commandments-of-cancer-prevention.*
SchizophreniaPrevention, 2020, https://www.webmd.com/schizophrenia/features/is-it-possible-to-prevent-schizophrenia#1.*
CancerCure, 2020, https://www.medicalnewstoday.com/articles/322700.*

(Continued)

*Primary Examiner* — Sun Jae Yoo

(57) ABSTRACT

The present invention relates to a class of cyano-substituted-heterocycles of Formula (I) with activity as inhibitors of deubiquitilating enzymes, in particular, ubiquitin C-terminal hydrolase 30 or ubiquitin specific peptidase 30 (USP30), having utility in a variety of therapeutic areas including cancer and conditions involving mitochondrial dysfunction. (I)

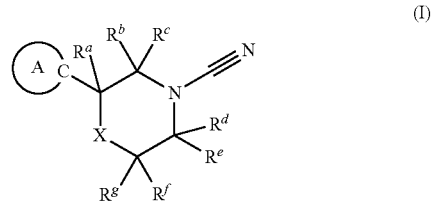

16 Claims, No Drawings

(56) References Cited

FOREIGN PATENT DOCUMENTS

| WO | 2017/141036 A1 | 8/2017 |
|---|---|---|
| WO | 2017/149313 A1 | 9/2017 |
| WO | 2017/158381 A1 | 9/2017 |
| WO | 2017/158388 A1 | 9/2017 |
| WO | 2017/163078 A1 | 9/2017 |
| WO | 2017172989 A1 | 10/2017 |
| WO | 2017198049 A1 | 11/2017 |
| WO | 2017198050 A1 | 11/2017 |
| WO | 2018060689 A1 | 4/2018 |
| WO | 2018060691 A1 | 4/2018 |
| WO | 2018060742 A1 | 4/2018 |
| WO | 2018065768 A1 | 4/2018 |
| WO | 2018220355 A1 | 12/2018 |
| WO | 2018234775 A1 | 12/2018 |

OTHER PUBLICATIONS

HeartFailure, 2020, https://www.heart.org/en/health-topics/heart-failure/treatment-options-for-heart-failure/medications-used-to-treat-heart-failure.*

MissionTherapeutics, 2020, https://missiontherapeutics.com/pipeline/usp30-inhibitor-programs/.*

Schizophrenia, 2020, https://www.webmd.com/schizophrenia/schizophrenia-therapy#1.*

SchizophreniaCure, 2020, https://www.helpguide.org/articles/mental-disorders/schizophrenia-treatment-and-self-help.htm.*

The International Search Report and Written Opinion, dated Nov. 17, 2017, in the corresponding PCT Appl. No. PCT/GB2017/052882.

Falgueyret et al., "Novel, Nonpeptidic Cyanamides as Potent and Reversible Inhibitors of Human Cathepsins K and L," J. Med. Chem. 2001, 44, 94-104.

Laine et al., "Discovery of Novel Cyanamide-Based Inhibitors of Cathepsin C," ACS Med. Chem. Lett. 2011, 2, 142-147.

Komander et al, "Breaking the chains: structure and function of the deubiquitinases", Nature Reviews Molecular Cell Biology, 10, 550-563, 2009.

Rydzewski et al, "Peptidic 1-Cyanopyrrolidines: Synthesis and SAR of a Series of Potent, Selective Cathepsin Inhibitors", Bioorganic & Medicinal Chemistry 10 (2002) 3277-3284.

Deaton et al, "Novel and potent cyclic cyanamide-based cathepsin K inhibitors", Bioorganic & Medicinal Chemistry Letters 15 (2005) 1815-1819.

Oballa et al, "A generally applicable method for assessing the electrophilicity and reactivity of diverse nitrile-containing compounds", Bioorganic & Medicinal Chemistry Letters 17 (2007) 998-1002.

Zapf et al, "Covalent Inhibitors of Interleukin—2 Inducible T Cell Kinase (Itk) with Nanomolar Potency in a Whole-Blood Assay", J. Med. Chem. 2012, 55, 10047-10063.

Nakamura et al, "Regulation of Mitochondrial Morphology by USP30, a Deubiquitinating Enzyme Present in the Mitochondrial Outer Membrane", Molecular Biology of the Cell, vol. 19, 1903-1911, May 2008.

Bingol et al, "The mitochondrial deubiquitinase USP30 opposes parkin-mediated mitophagy", Nature vol. 510, 370-375, 2014.

Liang et al, "USP30 deubiquitylates mitochondrial Parkin substrates and restricts apoptotic cell death", EMBO Reports, 1-10, 2015; DOI 10.15252/embr.201439820.

Bedford et al., "Ubiquitin-like protein conjugation and the ubiquitin—proteasome system as drug targets," Nat Rev Drug Discov. Jan. 2011;10(1)29-46.

Zheng et al., "Heterogeneous expression and biological function of ubiquitin carboxy-terminal hydrolase-L1 in osteosarcoma", Cancer Letters, 359, 36-46, 2015.

Ward et al., "Quantitative Chemical Proteomic Profiling of Ubiquitin Specific Proteases in Intact Cancer Cells," ACS Chem. Biol. 2016, 11, 3268-3272.

* cited by examiner

CYANO-SUBTITUTED HETEROCYCLES WITH ACTIVITY AS INHIBITORS OF USP30

This application is a National Stage Application of PCT/GB2017/052882 filed Sep. 27, 2017, which claims priority from UK Patent Application No. 1616511.0 filed on Sep. 29, 2016. The priority of said PCT and UK Patent Application are claimed. Each of the prior mentioned applications is hereby incorporated by reference herein in its entirety.

The present invention relates to a class of cyano-substituted-heterocycles with activity as inhibitors of deubiquitilating enzymes, in particular, ubiquitin C-terminal hydrolase 30 or ubiquitin specific peptidase 30 (USP30), uses thereof, processes for the preparation thereof and composition containing said inhibitors. These inhibitors have utility in a variety of therapeutic areas including cancer and conditions involving mitochondrial dysfunction.

Ubiquitin is a small protein consisting of 76 amino acids that is important for the regulation of protein function in the cell. Ubiquitylation and deubiquitylation are enzymatically mediated processes by which ubiquitin is covalently bound or cleaved from a target protein by deubiquitylating enzymes (DUBs), of which there are approximately 95 DUBs in human cells, divided into sub-families based on sequence homology. The USP family are characterised by their common Cys and His boxes which contain Cys and His residues critical for their DUB activities. The ubiquitylation and deubiquitylation processes have been implicated in the regulation of many cellular functions including cell cycle progression, apoptosis, modification of cell surface receptors, regulation of DNA transcription and DNA repair. Thus, the ubiquitin system has been implicated in the pathogenesis of numerous disease states including inflammation, viral infection, metabolic dysfunction, CNS disorders, and oncogenesis.

Ubiquitin is a master regulator of mitochondrial dynamics. Mitochondria are dynamic organelles whose biogenesis, fusion and fission events are regulated by the post-translational regulation via ubiquitylation of many key factors such as mitofusins. While ubiquitin ligases such as parkin are known to ubiquitylate a number of mitochondrial proteins, until recently, deubiquitylating enzymes remained elusive. USP30 is a 517 amino acid protein which is found in the mitochondrial outer membrane (Nakamura et al., Mol Biol 19:1903-11, 2008). It is the sole deubiquitylating enzyme bearing a mitochondrial addressing signal and has been shown to deubiquitylate a number of mitochondrial proteins. It has been demonstrated that USP30 opposes parkin-mediated mitophagy and that reduction of USP30 activity can rescue parkin-mediated defects in mitophagy.

Mitochondrial dysfunction can be defined as diminished mitochondrial content (mitophagy or mitochondrial biogenesis), as a decrease in mitochondrial activity and oxidative phosphorylation, but also as modulation of reactive oxygen species (ROS) generation. Hence a role for mitochondrial dysfunctions in a very large number of aging processes and pathologies including but not limited to, neurodegenerative diseases (e.g. Parkinson's disease (PD), Alzheimer's disease, Huntington's disease, Amylotrophic Lateral Sclerosis (ALS), multiple sclerosis), cancer, diabetes, metabolic disorders, cardio-vascular diseases, psychiatric diseases (e.g. Schizophrenia), and osteoarthritis.

For example, Parkinson's disease affects around 10 million people worldwide (Parkinson's Disease Foundation) and is characterised by the loss of dopaminergic neurons in the substantia nigra. The exact mechanisms underlying PD are unclear; however mitochondrial dysfunction is increasingly appreciated as a key determinant of dopaminergic neuronal susceptibility in PD and is a feature of both familial and sporadic disease, as well as in toxin-induced Parkinsonism. Parkin is one of a number of proteins that have been implicated with early onset PD. While most PD cases are linked to defects in alpha-synuclein, 10% of Parkinson's cases are linked to specific genetic defects, one of which is in the ubiquitin E3 ligase parkin. Parkin and the protein kinase PTEN-induced putative kinase 1 (PINK1) collaborate to ubiquitylate mitochondrial membrane proteins of damaged mitochondria resulting in mitophagy. Dysregulation of mitophagy results in increased oxidative stress, which has been described as a characteristic of PD. Inhibition of USP30 could therefore be a potential strategy for the treatment of PD. For example, PD patients with parkin mutations leading to reduced activity could be therapeutically compensated by inhibition of USP30.

It has been reported that depletion of USP30 enhances mitophagic clearance of mitochondria and also enhances parkin-induced cell death. USP30 has also been shown to regulate BAX/BAK-dependent apoptosis independently of parkin over expression. Depletion of USP30 sensitises cancer cells to BH-3 mimetics such as ABT-737, without the need for parkin over expression. Thus, an anti-apoptotic role has been demonstrated for USP30 and USP30 is therefore a potential target for anti-cancer therapy.

The ubiquitin-proteasome system has gained interest as a target for the treatment of cancer following the approval of the proteasome inhibitor bortezomib (Velcade®) for the treatment of multiple myeloma. Extended treatment with bortezomib is limited by its associated toxicity and drug resistance. However, therapeutic strategies that target specific aspects of the ubiquitin-proteasome pathway upstream of the proteaseome, such as DUBs, are predicted to be better tolerated (Bedford et al., Nature Rev 10:29-46, 2011).

Accordingly, there is a need for compounds that are inhibitors of USP30 for the treatment of indications where inhibition of USP30 is indicated.

Series of cyano-substituted-heterocycles are disclosed as deubiquitylating enzyme inhibitors in PCT applications WO 2016/046530, WO 2016/156816, WO 2017/009650, WO 2017/093718, WO 2017/103614, and PCT/GB2017/050830. Falgueyret et al., J. Med. Chem. 2001, 44, 94-104, and PCT application WO 01/77073 refer to cyanopyrrolidines as inhibitors of Cathepsins K and L, with potential utility in treating osteoporosis and other bone-resorption related conditions. PCT application WO 2015/179190 refers to N-acylethanolamine hydrolysing acid amidase inhibitors, with potential utility in treating ulcerative colitis and Crohn's disease. PCT application WO 2013/030218 refers to quinazolin-4-one compounds as inhibitors of ubiquitin specific proteases, such as USP7, with potential utility in treating cancer, neurodegenerative diseases, inflammatory disorders and viral infections. PCT applications WO 2014/068527, WO 2014/188173, WO 2015/017502, WO 2015/061247, WO 2016/019237 and WO 2016/192074 refer to inhibitors of Bruton's tyrosine kinase with potential utility in treating disease such as autoimmune disease, inflammatory disease and cancer. PCT applications WO 2009/026197, WO 2009/129365, WO 2009/129370, and WO 2009/129371, refer to cyanopyrrolidines as inhibitors of Cathepsin C with potential utility in treating COPD. United States patent application US 2008/0300268 refers to polyaromatic compounds as inhibitors of tyrosine kinase receptor PDGFR.

According to a first aspect, the present invention provides a compound of formula (I):

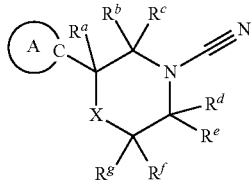

a tautomer thereof, or a pharmaceutically acceptable salt of said compound or tautomer, wherein:

X is selected from O, N($R^h$), and C($R^i$)($R^j$);

$R^a$ is selected from hydrogen, fluoro, optionally substituted $C_1$-$C_3$ alkyl, and optionally substituted $C_1$-$C_3$ alkoxy; or $R^a$ is linked to $R^b$ or $R^i$ to form an optionally substituted $C_3$-$C_4$ cycloalkyl ring;

$R^b$, $R^c$, $R^d$ and $R^e$, are each independently selected from hydrogen and optionally substituted $C_1$-$C_3$ alkyl; or form one or more spirocyclic groups where $R^b$ is linked to $R^c$ or $R^d$ is linked to $R^e$, or $R^b$ is linked to $R^a$ to form an optionally substituted $C_3$-$C_4$ cycloalkyl ring;

$R^f$ and $R^g$, are each independently selected from hydrogen, fluoro, cyano, optionally substituted $C_1$-$C_3$ alkyl, and optionally substituted $C_1$-$C_3$ alkoxy; or form a spirocyclic group where $R^f$ is linked to $R^g$, or $R^g$ is linked to $R^i$ to form an optionally substituted $C_3$-$C_4$ cycloalkyl ring;

when X is O or N($R^h$), none of $R^a$, $R^f$ and $R^g$, are fluoro or optionally substituted $C_1$-$C_3$ alkoxy;

$R^h$ is selected from hydrogen, optionally substituted $C_1$-$C_3$ alkyl, optionally substituted C(O)$C_1$-$C_3$ alkyl, optionally substituted S(O)$_2C_1$-$C_3$ alkyl, and optionally substituted 3 to 6-membered ring;

$R^i$ and $R^j$ are each independently selected from hydrogen, fluoro, cyano, optionally substituted $C_1$-$C_3$ alkyl, optionally substituted $C_1$-$C_3$ alkoxy, and optionally substituted 3 to 6-membered ring; or form a spirocyclic group where $R^i$ is linked to $R^j$, or $R^i$ is linked to $R^a$ or $R^g$ to form an optionally substituted $C_3$-$C_4$ cycloalkyl ring;

ring A is a 5 to 10-membered monocyclic or bicyclic, heteroaryl or heterocyclyl ring, which is unsubstituted, or substituted with one or more $Q^1(R^1)_n$ groups, which may be the same or different;

n is 0 or 1;

$Q^1$ is selected from $Q^{1a}$ and $Q^{1b}$;

$Q^{1a}$ is selected from oxo, halo, cyano, nitro, hydroxyl, $SR^4$, $NR^2R^3$, $CONR^2R^3$, $C_0$-$C_3$ alkylene-$NR^4COR^5$, $NR^4CONR^5R^6$, $COR^4$, $C(O)OR^4$, $SO_2R^4$, $SO_2NR^4R^5$, $NR^4SO_2R^5$, $NR^4SO_2NR^5R^6$, $NR^4C(O)OR^5$, optionally substituted $C_1$-$C_6$ alkyl, optionally substituted $C_1$-$C_6$ alkoxy, and optionally substituted $C_2$-$C_6$ alkenyl;

$Q^{1b}$ is selected from a covalent bond, an oxygen atom, a sulfur atom, $OR^7$, SO, $SO_2$, CO, C(O)O, $C_0$-$C_3$ alkylene-C(O)$NR^4$—$C_0$-$C_3$ alkylene, $C_0$-$C_3$ alkylene-$NR^4$—$C_0$-$C_3$ alkylene, $C_0$-$C_3$ alkylene-$NR^4$C(O)—$C_0$-$C_3$ alkylene, $NR^4CONR^5$, $SO_2NR^4$, $NR^4SO_2$, $NR^4SO_2NR^5$, $NR^4C(O)O$, $NR^4C(O)OR^7$, optionally substituted $C_1$-$C_6$ alkylene, and optionally substituted $C_2$-$C_6$ alkenylene;

$R^1$ is a 3 to 10-membered monocyclic or bicyclic, heterocyclyl, heteroaryl, cycloalkyl, or aryl ring;

$R^2$, $R^3$, $R^4$, $R^5$ and $R^6$, are each independently selected from hydrogen and optionally substituted $C_1$-$C_6$ alkyl;

$R^7$ is optionally substituted $C_1$-$C_6$ alkylene;

$R^1$ is unsubstituted or substituted with one or more substituents, each independently selected from halo, cyano, oxo, nitro, hydroxyl, $SR^8$, optionally substituted $C_1$-$C_6$ alkyl, optionally substituted $C_1$-$C_6$ alkoxy, optionally substituted $C_2$-$C_6$ alkenyl, optionally substituted $C_2$-$C_6$ alkynyl, $Q^{2a}$-$R^{11}$, $Q^{2a}$-O-$Q^{2b}$-$R^{11}$, $Q^{2a}$-S-$Q^{2b}$-$R^{11}$, $Q^{2a}$-SO-$Q^{2b}$-$R^{11}$, $Q^2$-$NR^8CONR^9R^{10}$, $Q^2$-$NR^8CONR^9$-$Q^{2a}$-$R^{11}$, $Q^{2a}$-$NR^8R^9$, $Q^{2a}$-$NR^8$-$Q^{2b}$-$R^{11}$, $Q^{2a}$-$COR^8$, $Q^{2a}$-CO-$Q^{2b}$-$R^{11}$, $Q^{2a}$-$NR^8COR^9$, $Q^{2a}$-$NR^8CO$-$Q^{2b}$-$R^{11}$, $Q^{2a}$-$NR^8C(O)OR^9$, $Q^{2a}$-$NR^8C(O)O$-$Q^{2b}$-$R^{11}$, $Q^{2a}$-$SO_2R^8$, $Q^{2a}$-$SO_2$-$Q^{2b}$-$R^{11}$, $Q^{2a}$-$CONR^8R^9$, $Q^{2a}$-$CONR^8$-$Q^{2b}$-$R^{11}$, $Q^{2a}$-$CO_2R^8$, $Q^{2a}$-$CO_2$-$Q^{2b}$-$R^{11}$, $Q^{2a}$-$SO_2NR^8R^9$, $Q^{2a}$-$SO_2NR^8$-$Q^{2b}$-$R^{11}$, $Q^{2a}$-$NR^8SO_2R^9$, $Q^{2a}$-$NR^8SO_2$-$Q^{2b}$-$R^{11}$, $Q^{2a}$-$NR^8SO_2NR^9R^{10}$, and $Q^{2a}$-$NR^8SO_2NR^9$-$Q^{2b}$-$R^{11}$;

$Q^{2a}$ and $Q^{2b}$ are each independently selected from a covalent bond, optionally substituted $C_1$-$C_6$ alkylene, and optionally substituted $C_2$-$C_6$ alkenylene;

$R^8$, $R^9$ and $R^{10}$, are each independently selected from hydrogen and optionally substituted $C_1$-$C_6$ alkyl; and $R^{11}$ is selected from optionally substituted heterocyclyl, optionally substituted heteroaryl, optionally substituted aryl, and optionally substituted cycloalkyl;

for use in the treatment of a disorder or condition where inhibition of USP30 is known, or can be shown, to produce a beneficial effect, in a mammal.

Unless otherwise indicated, the term substituted means substituted by one or more defined groups. In the case where groups may be selected from more than one alternatives, the selected groups may be the same or different. The term independently means that where more than one substituent is selected from more than one possible substituents, those substituents may be the same or different.

Unless otherwise indicated, alkyl, alkenyl, and alkoxy groups, including the corresponding divalent radicals, may be straight or branched and contain 1 to 6 carbon atoms and typically 1 to 4 carbon atoms. Examples of alkyl include methyl, ethyl, n-propyl, isopropyl, n-butyl, isobutyl, sec-butyl, pentyl and hexyl. Examples of alkoxy include methoxy, ethoxy, isopropoxy and n-butoxy.

$C_x$-$C_y$ alkyl refers to a saturated aliphatic hydrocarbon group having x-y carbon atoms which may be linear or branched. For example, $C_1$-$C_6$ alkyl contains from 1 to 6 carbon atoms and includes $C_1$, $C_2$, $C_3$, $C_4$, $C_5$ and $C_6$. "Branched" means that at least one carbon branch point is present in the group. For example, tert-butyl and isopropyl are both branched groups. Examples of $C_1$-$C_6$ alkyl groups include methyl, ethyl, propyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, tert-butyl, n-pentyl, isopentyl, neopentyl and n-hexyl. $C_1$-$C_6$ alkyl, $C_1$-$C_4$ alkyl and $C_1$-$C_3$ alkyl within the definitions of $R^a$, $R^b$, $R^c$, $R^d$, $R^e$, $R^f$, $R^g$, $R^h$, $R^i$, $R^j$, $R^2$, $R^3$, $R^4$, $R^5$, $R^6$, $R^8$, $R^9$, $R^{10}$, $Q^{1a}$, and within the definition of substituents for $R^1$, may be unsubstituted or substituted with one or more of the substituents defined herein. Examples of substituted $C_1$-$C_6$ alkyl therefore include $CF_3$, $CH_2CF_3$, $CH_2CN$, $CH_2OH$ and $CH_2CH_2OH$.

A $C_x$-$C_y$ alkylene group or moiety may be linear or branched and refers to a divalent hydrocarbon group having one less hydrogen atom from $C_x$-$C_y$ alkyl as defined above. $C_1$-$C_6$ alkylene may include intervening heteroatoms such as oxygen, and therefore includes alkyleneoxy groups. Alkyleneoxy as employed herein also extends to embodiments in which the or an oxygen atom (e.g. a single oxygen atom) is located within the alkylene chain, for example $CH_2CH_2OCH_2$ or $CH_2OCH_2$. Examples of $C_1$-$C_6$ alkylene groups include methylene, methyleneoxy, ethylene, ethyleneoxy, n-propylene, n-propyleneoxy, n-butylene, n-butyleneoxy, methylmethylene and dimethylmethylene. Unless stated otherwise, $C_1$-$C_6$ alkylene, $C_1$-$C_4$ alkylene and $C_1$-$C_3$ alkylene within the definitions of $R^7$, $Q^{1b}$, $Q^{2a}$ and $Q^{2b}$ may be unsubstituted or substituted with one or more of the substituents defined herein.

$C_2$-$C_6$ alkenyl refers to a linear or branched hydrocarbon chain radical containing at least two carbon atoms and at least one double bond and includes $C_2$-$C_4$ alkenyl. Examples of alkenyl groups include ethenyl, propenyl, 2-propenyl, 1-butenyl, 2-butenyl, 1-hexenyl, 2-methyl-1-propenyl, 1,2-butadienyl, 1,3-pentadienyl, 1,4-pentadienyl and 1-hexadienyl. Unless stated otherwise, $C_2$-$C_6$ alkenyl within the definitions of $Q^{1a}$ and within the definition of substituents for $R^1$, may be unsubstituted or substituted with one or more of the substituents defined herein.

$C_2$-$C_6$ alkenylene refers to a linear or branched hydrocarbon group having one less hydrogen atom from $C_2$-$C_6$ alkenyl as defined above. Examples of $C_2$-$C_6$ alkenylene include ethenylene, propenylene and butenylene. Unless stated otherwise, $C_2$-$C_6$ alkenylene and $C_2$-$C_4$ alkenylene within the definition of substituents for $Q^b$, $Q^{2a}$, $Q^{2b}$, may be unsubstituted or substituted with one or more of the substituents defined herein.

$C_2$-$C_6$ alkynyl refers to a linear or branched hydrocarbon chain radical containing at least two carbon atoms and at least one triple bond. Examples of alkenyl groups include ethynyl, propynyl, 2-propynyl, 1-butynyl, 2-butynyl and 1-hexynyl. Unless specified otherwise, $C_2$-$C_6$ alkynyl, within the definition of substituents for $R^1$, may be unsubstituted or substituted with one or more of the substituents defined herein.

$C_1$-$C_6$ alkoxy refers to a group or part of a group having an —O—$C_x$-$C_y$ alkyl group according to the definition of $C_x$-$C_y$ alkyl above. $C_1$-$C_6$ alkoxy contains from 1 to 6 carbon atoms and includes $C_1$, $C_2$, $C_3$, $C_4$, $C_5$ and $C_6$. Examples of $C_1$-$C_6$ alkoxy include methoxy, ethoxy, propoxy, iso-propoxy, butoxy, pentoxy and hexoxy. Alkoxy as employed herein also extends to embodiments in which the or an oxygen atom (e.g. a single oxygen atom) is located within the alkyl chain, for example $CH_2CH_2OCH_3$ or $CH_2OCH_3$. Thus, the alkoxy may be linked through carbon to the remainder of the molecule, for example, —$CH_2CH_2OCH_3$, or alternatively, the alkoxy is linked through oxygen to the remainder of the molecule, for example —$OC_{1-6}$ alkyl. In one instance, the alkoxy is linked through oxygen to the remainder of the molecule but the alkoxy group contains a further oxygen atom, for example, $OCH_2CH_2OCH_3$. Unless specified otherwise, $C_1$-$C_6$ alkoxy and $C_1$-$C_3$ alkoxy within the definitions $R^a$, $R^f$, $R^g$, $R^i$, $R^j$, $Q^{1a}$, and within the definition of substituents for $R^1$, may be unsubstituted or substituted with one or more of the substituents defined herein. Examples of substituted $C_1$-$C_6$ alkoxy therefore include $OCF_3$, $OCHF_2$, $OCH_2CF_3$, $CH_2CH_2OCH_3$ and $CH_2CH_2OCH_2CH_3$.

The term halo refers to chloro, bromo, fluoro or iodo, in particular chloro or fluoro. Haloalkyl and haloalkoxy groups may contain one or more halo substituents. Examples are trifluoromethyl and trifluoromethoxy. The term "oxo" means =O. The term "nitro" means NO2 and includes SF5 (a known mimetic of nitro).

Cycloalkyl, heterocyclyl, aryl and heteroaryl rings disclosed herein and within the definitions of $R^a$, $R^b$, $R^c$, $R^d$, $R^e$, $R^f$, $R^g$, $R^h$, $R^i$, $R^j$, $R^1$, $R^{11}$ and ring A may be monocyclic or bicyclic. Bicyclic ring systems include bridged, fused and spiro ring systems. In particular, the bicyclic ring systems are fused ring systems. A substituent if present may be attached to any suitable ring atom which may be a carbon atom or, in the case of heteroaryl and heterocyclic ring systems, a heteroatom.

"cycloalkyl" refers to a monocyclic saturated or partially unsaturated, non-aromatic ring, wherein all of the ring atoms are carbon, and having the number of ring atoms as indicated. For example, $C_3$-$C_{10}$ cycloalkyl refers to a monocyclic or bicyclic hydrocarbon ring containing 3 to 10 carbon atoms. Examples of $C_3$-$C_{10}$ cycloalkyl are cyclopropyl, cyclobutyl, cyclopentyl, cyclohexyl, cycloheptyl, cyclooctyl and decahydronaphthalenyl. Bicyclic cycloalkyl groups include bridged ring systems such as bicycloheptane and bicyclooctane. Unless specified otherwise, cycloalkyl within the definitions of $R^a$, $R^b$, $R^e$, $R^f$, $R^g$, $R^h$, $R^i$, $R^j$, $R^1$, $R^{11}$, may be unsubstituted or substituted with one or more of the substituents defined herein.

An "aryl" group/moiety refers to any monocyclic or bicyclic hydrocarbon group comprising at least one aromatic group and having from 5 to 10 carbon atom ring members. Examples of aryl groups include phenyl and naphthyl. Bicyclic rings may be fused aromatic rings where both rings are aromatic, for example, naphthalenyl. Preferred aryl groups are phenyl and naphthyl, more preferably phenyl. Unless specified otherwise, aryl within the definitions of $R^h$, $R^i$, $R^j$, $R^1$ and $R^{11}$, may be unsubstituted or substituted with one or more of the substituents defined herein.

"Heteroaryl" as used herein means a polyunsaturated, monocyclic or bicyclic 5 to 10-membered aromatic moiety containing at least one and up to 5 heteroatoms, particularly 1, 2 or 3 heteroatoms selected from N, O and S, and the remaining ring atoms are carbon atoms, in stable combinations known to the skilled person. Heteroaryl ring nitrogen and sulfur atoms are optionally oxidised, and the nitrogen atom(s) are optionally quaternized. A heteroaryl ring can be a single aromatic ring or a fused bicyclic ring where the bicyclic ring system can be aromatic, or one of the fused rings is aromatic and the other is at least partially saturated. Examples of fused rings where one of the rings is aromatic and the other is at least partially saturated include tetrahydropyridopyrazinyl, tetrahydroquinolinyl and tetrahydroisoquinolinyl. In such instances, attachment of the bicyclic ring to the group it is a substituent of, e.g. the cyanopyrrolidine core, is via the aromatic ring of the bicycle. In particular examples, a bicyclic heteroaryl is one in which the entire fused ring system is aromatic. A bicyclic heteroaryl can have the at least one heteroatom in either of the fused rings. For example, a bicyclic ring with an aromatic ring fused to a partially saturated ring may contain the at least one heteroatom in the aromatic ring or the partially saturated ring. Attachment of the bicyclic ring to the group it is a substituent of may be via either a heteroatom containing ring or a carbon only containing ring. The point of attachment of heteroaryl to the group it is a substituent of can be via a carbon atom or a heteroatom (e.g. nitrogen). In instances where ring A is a heteroaryl ring, attachment to the cyanopyrrolidine core is via a carbon ring atom in an aromatic ring, wherein the aromatic ring may be fused to a further aromatic or partially saturated ring.

Examples include pyridinyl, pyrazinyl, pyrimidinyl, pyridazinyl, furanyl, thiophenyl, pyrrolyl, oxazolyl, thiazolyl, pyrazolyl, triazolyl, tetrazolyl, indolyl, indolizinyl, isoindolyl, purinyl, furazanyl, imidazolyl, indazolyl, isothiazolyl, isoxazolyl, oxadiazolyl, tetrazolyl, thiadiazolyl, benzofuranyl, isobenzofuranyl, benzothiophenyl, isobenzothiophenyl, benzimidazolyl, benzothiazolyl, benzoxazolyl, napthyridinyl, pteridinyl, pyrazinyl, quinolinyl, isoquinolinyl, cinnolinyl, phthalazinyl, quinazolinyl, imidazopyridinyl, pyrazolopyridinyl, thiazolopyridinyl, triazinyl, dihydropyridinyl, dihydropyrrolopyridinyl, quinoxalinyl, dihydrobenzoxazinyl, tetrahydropyrazinyl, tetrahydroquinolinyl, oxazolopyridinyl, and tetrahydroisoquinolinyl. Unless specified otherwise, heteroaryl within the definitions of $R^h$, $R^i$, $R^j$, $R^1$, $R^{11}$ and ring A, may be unsubstituted or substituted with one or more of the substituents defined herein.

"Heterocyclyl" or "heterocyclic" as used herein in describing a ring means, unless otherwise stated, a monocyclic saturated or partially unsaturated, non-aromatic ring or a bicyclic saturated or partially unsaturated ring, wherein the bicyclic ring system is non-aromatic, the mono- or bicyclic ring having, for example, 3 to 10 members or 5 to 10 members, where at least one member and up to 5 members, particularly 1, 2 or 3 members of the ring are heteroatoms selected from N, O and S, and the remaining ring atoms are carbon atoms, in stable combinations known to those of skill in the art. Heterocyclic ring nitrogen and sulfur atoms are optionally oxidised, and the nitrogen atoms (s) are optionally quaternized. As used herein, the heterocyclic ring may be a fused ring to another ring system to form a bicycle, i.e. one or two of the heterocyclic ring carbons is common to an additional ring system. In instances where the heterocyclyl is a bicyclic ring, the second ring can be aromatic, e.g. a fused phenyl, pyridyl, pyrazolyl, or the like. The heterocyclyl may be linked through carbon or a heteroatom to the remainder of the molecule and in instances where the heterocylyl is a bicyclic ring, the link may be via the heteroatom containing ring or the fused ring. In instances where ring A is a heterocyclyl ring, attachment to the cyanopyrrolidine core is via a carbon ring atom in the non-aromatic ring, wherein the non-aromatic ring may be fused to a further ring which may be aromatic or non-aromatic. Examples of heterocyclyl groups include azetidinyl, pyrrolidinyl, piperidinyl, azepanyl, diazepanyl, dihydrofuranyl (e.g. 2,3-dihydrofuranyl, 2,5-dihydrofuranyl), dioxolanyl, morpholinyl, oxazolidinyl, oxazinanyl, indolinyl, isoindolinyl, piperazinyl, tetrahydrofuranyl, thiomorpholinyl, dihydropyranyl (e.g. 3,4-dihydropyranyl, 3,6-dihydropyranyl), homopiperazinyl, dioxanyl, hexahydropyrimidinyl, pyrazolinyl, pyrazolidinyl, 4H-quinolizinyl, quinuclidinyl, tetrahydropyranyl, tetrahydropyridinyl, tetrahydropyrimidinyl, tetrahydrothiophenyl, thiazolidinyl, benzopyranyl, tetrahydroquinolinyl, dihydropyrrolopyridinyl, dihydrobenzoxazinyl, pyrrolopyridinyl, dihydronaphthyridinyl, dihydroisoquinolinyl and tetrahydroisoquinolinyl. Unless specified otherwise, heterocyclyl within the definitions of $R^h$, $R^i$, $R^j$, $R^1$, $R^{11}$ and ring A, may be unsubstituted or substituted with one or more of the substituents defined herein.

"Optionally substituted" as applied to any group means that the said group may if desired be substituted with one or more substituents (e.g., 1, 2, 3 or 4 substituents) which may be the same or different.

Examples of suitable substituents for "substituted" and "optionally substituted" $C_1$-$C_6$ alkyl (including $C_1$-$C_4$ alkyl, $C_1$-$C_3$ alkyl and $C_1$-$C_2$ alkyl) and $C_1$-$C_6$ alkoxy (including $C_1$-$C_4$ alkoxy, $C_1$-$C_3$ alkoxy and $C_1$-$C_2$ alkoxy) and $C_2$-$C_6$ alkenyl (including $C_2$-$C_4$ alkenyl) and $C_2$-$C_6$ alkynyl (including $C_2$-$C_4$ alkynyl) within the definitions of $R^a$, $R^b$, $R^c$, $R^d$, $R^e$, $R^f$, $R^g$, $R^h$, $R^i$, $R^j$, $R^2$, $R^3$, $R^4$, $R^5$, $R^6$, $R^8$, $R^9$, $R^{10}$, $Q^{1a}$, and within the definition of substituents for $R^1$, and $C_1$-$C_6$ alkylene (including $C_1$-$C_3$ alkylene) and $C_2$-$C_6$ alkenylene within the definitions of $R^7$, $Q^{1b}$, $Q^{2a}$ and $Q^{2b}$, include $C_1$-$C_6$ alkoxy, halo, hydroxyl, thiol, cyano, amino and nitro, in particular, halo (preferably fluoro or chloro), hydroxyl and cyano.

Examples of suitable substituents for "substituted" and "optionally substituted" rings, i.e. cycloalkyl, heterocyclyl, aryl and heteroaryl rings, within the definitions of $R^a$, $R^b$, $R^c$, $R^d$, $R^e$, $R^f$, $R^g$, $R^h$, $R^i$, $R^j$, $R^1$, $R^{11}$ and ring A, include halo, cyano, oxo, nitro, amino, amide, hydroxy, $C_1$-$C_6$ alkyl or $C_1$-$C_3$ alkyl, $C_1$-$C_6$ alkoxy or $C_1$-$C_3$ alkoxy, aryl, heteroaryl, heterocyclyl, $C_3$-$C_6$ cycloalkyl, $C_{1-3}$ alkylamino, $C_{2-6}$ alkenylamino, di-$C_1$-$C_3$ alkylamino, $C_1$-$C_3$ acylamino, di-$C_1$-$C_3$ acylamino, carboxy, $C_1$-$C_3$ alkoxycarbonyl, carboxamidyl, mono-$C_{1-3}$ carbamoyl, di-$C_{1-3}$ carbamoyl or any of the above in which a hydrocarbyl moiety is itself substituted by halo, in particular fluoro, hydroxyl, cyano, amino and nitro. In groups containing an oxygen atom such as hydroxy and alkoxy, the oxygen atom can be replaced with sulfur to make groups such as thio (SH) and thio-alkyl (S-alkyl). Optional substituents therefore include groups such as S-methyl. In thio-alkyl groups, the sulfur atom may be further oxidised to make a sulfoxide or sulfone, and thus optional substituents therefore includes groups such as S(O)-alkyl and $S(O)_2$-alkyl.

Examples of suitable substituents for "substituted" and "optionally substituted" rings include in particular, halo, oxo, cyano, $C_1$-$C_3$ alkyl, $C_1$-$C_3$ alkoxy, heterocyclyl, cycloalkyl, heteroary or aryl, wherein the alkyl or alkoxy is optionally substituted with one or more (e.g. one, two or three) substituents selected from halo, hydroxyl, thiol, cyano, amino and nitro. In particular, suitable substituents for "substituted" and "optionally substituted" rings disclosed herein include fluoro, chloro, oxo, cyano, $C_1$-$C_3$ alkyl, $C_1$-$C_3$ alkoxy, wherein the alkyl or alkoxy is optionally substituted with one or more (e.g. one, two or three) substituents selected from halo, hydroxyl, thiol, cyano, amino and nitro, in particular, one or more fluoro.

Substituted groups thus include for example Br, Cl, F, CN, Me, Et, Pr, t-Bu, OMe, OEt, OPr, $C(CH_3)_3$, $CH(CH_3)_2$, $CF_3$, $OCF_3$, $C(O)NHCH_3$, cyclopropyl, phenyl, etc. In the case of aryl groups, the substitutions may be in the form of rings from adjacent carbon atoms in the aryl ring, for example cyclic acetals such as O—$CH_2$—O.

Preferred embodiments of the compound of formula (I) for use in the present invention are defined below.

$R^a$ may represent hydrogen. $R^a$ may represent $C_1$-$C_3$ alkyl. $R^a$ may represent $C_1$-$C_2$ alkyl (e.g. methyl or ethyl). $R^a$ may represent methyl or substituted methyl. When X is $C(R^i)(R^j)$, $R^a$ may represent fluoro. When X is $C(R^i)(R^j)$, $R^a$ may represent optionally substituted $C_1$-$C_3$ alkoxy (e.g. methoxy or ethoxy). In one embodiment, when $R^a$ is other than hydrogen, $R^b$, $R^c$, $R^d$, $R^e$, $R^f$, $R^g$, and $R^h$ or $R^i$ and $R^j$ if present, each represent hydrogen. The alkyl within the definition of $R^a$ may be unsubstituted or substituted with one or more substituents selected from $C_1$-$C_6$ alkoxy, halo, hydroxyl, thiol, cyano, amino, amido and nitro. In particular, the alkyl is optionally substituted with fluoro.

$R^b$ may represent hydrogen. $R^b$ may represent $C_1$-$C_3$ alkyl. $R^b$ may represent $C_1$-$C_2$ alkyl (e.g. methyl or ethyl). $R^b$ may represent methyl or substituted methyl. When $R^b$ represents $C_1$-$C_3$ alkyl and $R^a$, $R^c$, $R^d$, $R^e$, $R^f$, $R^g$, and $R^h$ or $R^i$ and $R^j$ if present, each represent hydrogen. The alkyl within the definition of $R^b$ may be unsubstituted or substituted with one or more substituents selected from $C_1$-$C_6$ alkoxy, halo, hydroxyl, thiol, cyano, amino, amido and nitro. In particular, the alkyl is optionally substituted with fluoro.

In one embodiment, when $R^b$ is other than hydrogen, $R^c$ is hydrogen. When $R^c$ is other than hydrogen, $R^b$ may be hydrogen, such that one of $R^b$ and $R^c$ is hydrogen.

In another embodiment, $R^b$ and $R^c$ may each represent methyl.

$R^d$ may represent hydrogen. $R^d$ may represent $C_1$-$C_3$ alkyl. $R^d$ may represent $C_1$-$C_2$ alkyl (e.g. methyl or ethyl). $R^d$ may represent methyl or substituted methyl. When $R^d$ represents $C_1$-$C_3$ alkyl and $R^a$, $R^b$, $R^c$, $R^e$, $R^f$, $R^g$, and $R^h$ or $R^i$ and $R^j$ if present, each represent hydrogen. The alkyl within the definition of $R^d$ may be unsubstituted or substituted with one or more substituents selected from $C_1$-$C_6$ alkoxy, halo, hydroxyl, thiol, cyano, amino, amido and nitro. In particular, the alkyl is optionally substituted with fluoro.

In one embodiment, when $R^d$ is other than hydrogen, $R^e$ is hydrogen. When $R^e$ is other than hydrogen, $R^d$ may be hydrogen, such that one of $R^d$ and $R^e$ is hydrogen.

In another embodiment, $R^d$ and $R^e$ may each represent methyl.

$R^f$ may represent hydrogen. $R^f$ may represent cyano. $R^f$ may represent $C_1$-$C_3$ alkyl. $R^f$ may represent $C_1$-$C_2$ alkyl (e.g. methyl or ethyl). $R^f$ may represent methyl or substituted methyl. When X is $C(R^i)(R^j)$, $R^f$ may represent fluoro. When X is $C(R^i)(R^j)$, $R^f$ may represent optionally substituted $C_1$-$C_3$ alkoxy (e.g. methoxy or ethyoxy). When $R^f$ is other than hydrogen, $R^a$, $R^b$, $R^c$, $R^d$, $R^e$, $R^g$, and $R^h$ or $R^i$ and $R^j$ if present, may each represent hydrogen. The alkyl within the definition of $R^f$ may be unsubstituted or substituted with one or more substituents selected from $C_1$-$C_6$ alkoxy, halo, hydroxyl, thiol, cyano, amino, amido and nitro. In particular, the alkyl is optionally substituted with fluoro.

In one embodiment, when $R^f$ is other than hydrogen, $R^g$ is hydrogen. When $R^g$ is other than hydrogen, $R^f$ may be hydrogen, such that one of $R^f$ and $R^g$ is hydrogen.

In another embodiment, $R^f$ and $R^g$ may each represent fluoro. Alternatively, $R^f$ and $R^g$ may each represent methyl.

$R^h$ is only present when X represents $N(R^h)$. $R^h$ may represent hydrogen. $R^h$ may represent $C_1$-$C_3$ alkyl. $R^h$ may represent $C_1$-$C_2$ alkyl (e.g. methyl or ethyl). $R^h$ may represent methyl or substituted methyl. $R^h$ may represent a 3 to 6-membered heterocyclyl, cycloalkyl, heteroaryl or aryl ring. When $R^h$ is other than hydrogen, $R^a$, $R^b$, $R^c$, $R^d$, $R^e$, $R^f$ and $R^g$ may each represent hydrogen. The alkyl within the definition of $R^h$ may be unsubstituted or substituted with one or more substituents selected from $C_1$-$C_6$ alkoxy, halo, hydroxyl, thiol, cyano, amino, amio and nitro, wherein the alkyl and alkoxy may be optionally substituted with halo.

$R^i$ and $R^j$ are only present when X represents $C(R^i)(R^j)$. $R^i$ may represent hydrogen. $R^i$ may represent fluoro. $R^i$ may represent cyano. $R^i$ may represent $C_1$-$C_3$ alkyl. $R^i$ may represent $C_1$-$C_2$ alkyl (e.g. methyl or ethyl). $R^i$ may represent methyl or substituted methyl. $R^i$ may represent $C_1$-$C_3$ alkoxy. $R^i$ may represent $C_1$-$C_2$ alkoxy (e.g. methoxy or ethoxy). $R^i$ may represent methoxy or substituted methoxy. $R^i$ may represent a 3 to 6-membered heterocyclyl, cycloalkyl, heteroaryl or aryl ring.

In one embodiment, when $R^i$ is other than hydrogen, $R^j$ is hydrogen. When $R^j$ is other than hydrogen, $R^i$ may be hydrogen, such that one of $R^i$ and $R^j$ is hydrogen.

Alternatively, $R^b$ and $R^c$ may together form a spirocyclic ring. In addition, or alternatively, $R^d$ and $R^e$ may together form a spirocyclic ring. In addition, or alternatively, $R^f$ and $R^g$ may together form a spirocyclic ring. In addition, or alternatively, if present, $R^i$ and $R^j$ may together form a spirocyclic ring. In such instances, preferably only one of $R^b/R^c$, $R^d/R^e$, $R^f/R^g$ and $R^i/R^j$ form a spirocyclic ring, wherein the remaining groups may each represent hydrogen.

The spirocyclic ring can contain 3, 4, 5 or 6 carbon ring atoms, in particular 3 or 4 carbon ring atoms. The spirocyclic ring shares one ring atom with the cyanopyrrolidine core. The spirocyclic ring may be unsubstituted or substituted with a substituent selected from halo, cyano, oxo, nitro, amino, amido, hydroxyl, $C_1$-$C_6$ alkyl or $C_1$-$C_3$ alkyl, $C_1$-$C_6$ alkoxy or $C_1$-$C_3$ alkoxy, wherein the alkyl and alkoxy may be optionally substituted with halo.

Neighbouring R groups attached to the carbon ring atoms of the cyanopyrrolidine core may together form an optionally substituted $C_3$-$C_4$ cycloalkyl ring. For example, $R^a$ together with $R^b$, $R^a$ together with $R^i$, and $R^g$ together with $R^i$. In such instances, preferably one cycloalkyl group is present whist the remaining R groups each represent hydrogen. The $C_3$-$C_4$ cycloalkyl ring may be unsubstituted or substituted with a substituent selected from halo, cyano, oxo, nitro, amino, amido, hydroxyl, $C_1$-$C_6$ alkyl or $C_1$-$C_3$ alkyl, $C_1$-$C_6$ alkoxy or $C_1$-$C_3$ alkoxy, wherein the alkyl and alkoxy may be optionally substituted with halo.

In all cases described herein, X represents O, $N(R^h)$ or $C(R^i)(R^j)$.

X may represent O.

X may represent $N(R^h)$. When X represents $N(R^h)$, $R^h$ represents hydrogen, optionally substituted $C_1$-$C_3$ alkyl, optionally substituted $C(O)C_1$-$C_3$ alkyl, optionally substituted $S(O)_2C_1$-$C_3$ alkyl or an optionally substituted 3 to 6-membered ring. The 3 to 6-membered ring may be a cycloalkyl, aryl, heterocyclyl or heteroaryl ring.

In particular, $R^h$ represents $C_1$-$C_3$ alkyl, $C(O)C_1$-$C_3$ alkyl, $S(O)_2C_1$-$C_3$ alkyl or a 5 or 6-membered aryl or heteroaryl ring.

Alternatively, X may represent $C(R^i)(R^j)$. When X represents $C(R^i)(R^j)$, $R^i$ and $R^j$ each independently represent hydrogen, fluoro, cyano, an optionally substituted $C_1$-$C_3$ alkyl, an optionally substituted $C_1$-$C_3$ alkoxy, an optionally substituted 3 to 6-membered ring, a spirocyclic group where $R^i$ is linked to $R^j$, or $R^i$ is linked to $R^a$ or $R^g$ to form an optionally substituted $C_3$-$C_4$ cycloalkyl ring.

One of $R^a$, $R^b$, $R^c$, $R^d$, $R^e$, $R^f$, $R^g$, and $R^h$ or $R^i$ and $R^j$ if present, may be other than hydrogen and the remaining each represent hydrogen.

Two of $R^a$, $R^b$, $R^c$, $R^d$, $R^e$, $R^f$, $R^g$, and $R^h$ or $R^i$ and $R^j$ if present, may be other than hydrogen and the remaining each represent hydrogen.

Three of $R^a$, $R^b$, $R^c$, $R^d$, $R^e$, $R^f$, $R^g$, and $R^h$ or $R^i$ and $R^j$ if present, may be other than hydrogen and the remaining each represent hydrogen.

Four of $R^a$, $R^b$, $R^c$, $R^d$, $R^e$, $R^f$, $R^g$, and $R^h$ or $R^i$ and $R^j$ if present, may be other than hydrogen and the remaining each represent hydrogen.

Five of $R^a$, $R^b$, $R^c$, $R^d$, $R^e$, $R^f$, $R^g$, and $R^h$ or $R^i$ and $R^j$ if present, may be other than hydrogen and the remaining each represent hydrogen.

Six of $R^a$, $R^b$, $R^c$, $R^d$, $R^e$, $R^f$, $R^g$, and $R^h$ or $R^i$ and $R^j$ if present, may be other than hydrogen and the remaining each represent hydrogen.

When one, two, three, four, five or six of $R^a$, $R^b$, $R^c$, $R^d$, $R^e$, $R^f$, $R^g$, and $R^h$ or $R^i$ and $R^j$ if present, are other than hydrogen, the other R groups represent a group in accordance with the definitions above. In particular, one, two, three or four of $R^a$, $R^b$, $R^c$, $R^d$, $R^e$, $R^f$, $R^g$, and $R^h$ or $R^i$ and $R^j$ if present, are other than hydrogen and the remaining each represent hydrogen. More particularly, one or two of $R^a$, $R^b$, $R^c$, $R^d$, $R^e$, $R^f$, $R^g$, and $R^h$ or $R^i$ and $R^j$ if present, are other than hydrogen and the remaining each represent hydrogen.

In one embodiment, $R^a$, $R^b$, $R^c$, $R^d$, $R^e$, $R^f$, $R^g$, and $R^h$ or $R^i$ and $R^j$ if present, each represent hydrogen.

In formula (I) defined herein, ring A represents a 5 to 10-membered (e.g. 5, 6, 7, 8, 9 or 10-membered) monocyclic or bicyclic heteroaryl or heterocyclyl ring.

Ring A may represent a 5 to 10-membered heteroaryl or hetoercyclyl ring substituted with one or more (e.g. one, two, three or four) of $Q^1(R^1)_n$, in particular one or two of $Q^1(R^1)_n$.

In particular, ring A may represent a 5 to 6-membered heteroaryl or heterocyclyl ring which is substituted with one or more (e.g. one, two, three or four) of $Q^1(R^1)_n$.

Alternatively, ring A may represent a 9 to 10-membered bicyclic heteroaryl or heterocyclyl ring which is substituted with one or more (e.g. one, two, three or four) of $Q^1(R^1)_n$.

Ring A may comprises one or more (e.g. 1, 2, 3 or 4) heteroatoms independently selected from nitrogen, oxygen and sulfur. In particular, ring A contains at least one nitrogen atom, for example, 1, 2 or 3 nitrogen atoms, preferably 1 or 2 nitrogen heteroatoms.

Ring A may be selected from the group consisting of azetidinyl, pyrrolidinyl, piperidinyl, azepanyl, diazepanyl, dihydrofuranyl (e.g. 2,3-dihydrofuranyl, 2,5-dihydrofuranyl), dioxolanyl, morpholinyl, oxazolidinyl, oxazinanyl, indolinyl, isoindolinyl, piperazinyl, tetrahydrofuranyl, thiomorpholinyl, dihydropyranyl (e.g. 3,4-dihydropyranyl, 3,6-dihydropyranyl), homopiperazinyl, dioxanyl, hexahydropyrimidinyl, pyrazolinyl, pyrazolidinyl, 4H-quinolizinyl, quinuclidinyl, tetrahydropyranyl, tetrahydropyridinyl, tetrahydropyrimidinyl, tetrahydrothiophenyl, thiazolidinyl, benzopyranyl, tetrahydroquinolinyl dihydropyrrolopyridinyl, dihydrobenzoxazinyl, pyrrolopyridinyl, dihydronaphthyridinyl, dihydroisoquinolinyl, tetrahydroisoquinolinyl, pyridinyl, pyrazinyl, pyrimidinyl, pyridazinyl, furanyl, thiophenyl, pyrrolyl, oxazolyl, thiazolyl, pyrazolyl, triazolyl, tetrazolyl, indolyl, indolizinyl, isoindolyl, purinyl, furazanyl, imidazolyl, indazolyl, isothiazolyl, isoxazolyl, oxadiazolyl, tetrazolyl, thiadiazolyl, benzofuranyl, isobenzofuranyl, benzothiophenyl, isobenzothiophenyl, benzimidazolyl, benzothiazolyl, benzoxazolyl, napthyridinyl, pteridinyl, pyrazinyl, quinolinyl, isoquinolinyl, cinnolinyl, phthalazinyl, quinazolinyl, imidazopyridinyl, pyrazolopyridinyl, thiazolopyridinyl, triazinyl, dihydropyridinyl, dihydropyrrolopyridinyl, quinoxalinyl, dihydrobenzoxazinyl, and tetrahydropyrazinyl.

In particular, ring A is selected from imidazopyridinyl, triazolyl, benzoimidazolyl and oxazolyl.

Ring A may be substituted with one or more $Q^1(R^1)_n$, wherein each occurrence of $Q^1(R^1)_n$ may be the same or different, wherein:

n is 0 or 1;

$Q^1$ represents $Q^{1a}$ or $Q^{1b}$ (i.e., when n is 0, $Q^1$ is $Q^{1a}$ and when n is 0, $Q^1$ is $Q^{1b}$); wherein $Q^{1a}$ is selected from oxo, halo, cyano, nitro, hydroxyl, $SR^4$, $NR^2R^3$, $CONR^2R^3$, $C_0$-$C_3$-alkylene-$NR^4COR^5$, $NR^4CONR^5R^6$, $COR^4$, $C(O)OR^4$, $SO_2R^4$, $SO_2NR^4R^5$, $NR^4SO_2R^5$, $NR^4SO_2NR^5R^6$, $NR^4C(O)OR^5$, optionally substituted $C_1$-$C_6$ alkyl, optionally substituted $C_1$-$C_6$ alkoxy, optionally substituted $C_2$-$C_6$ alkenyl;

$Q^{1b}$ is selected from a covalent bond, an oxygen atom, a sulfur atom, $OR^7$, SO, $SO_2$, CO, $C(O)O$, $C_0$-$C_3$-alkylene-C(O)$NR^4$—$C_0$-$C_3$ alkylene, $C_0$-$C_3$-alkylene-$NR^4$—$C_0$-$C_3$ alkylene, $C_0$-$C_3$-alkylene-$NR^4C(O)$—$C_0$-$C_3$ alkylene, $NR^4CONR^5$, $SO_2NR^4$, $NR^4SO_2$, $NR^4SO_2NR^5$, $NR^4C(O)O$, $NR^4C(O)OR^7$, optionally substituted $C_1$-$C_6$ alkylene, or optionally substituted $C_2$-$C_6$ alkenylene;

$R^1$ represents an optionally substituted 3 to 10-membered monocyclic or bicyclic heterocyclyl, hetoeraryl, cycloalkyl or aryl ring;

$R^2$ and $R^3$ each independently represent hydrogen or optionally substituted $C_1$-$C_6$ alkyl, wherein $R^2$ and $R^3$ cannot both be hydrogen;

$R^4$, $R^5$ and $R^6$ each independently represent hydrogen or optionally substituted $C_1$-$C_6$ alkyl;

$R^7$ represents optionally substituted $C_1$-$C_6$ alkylene;

Preferably, $Q^{1b}$ is not —NH— when $R^1$ is a nitrogen-containing heteroaryl ring.

Ring A may be substituted with one, two, three or four of $Q^1(R^1)_n$. For example, ring A may be substituted with one, two or three of $Q^1(R^1)_n$. In particular, ring A is substituted with one or two of $Q^1(R^1)_n$. Each occurrence of $Q^1(R^1)_n$ may be the same or different. More particularly, ring A is substituted with one of $Q^1(R^1)_n$. $Q^1$, $R^1$ and n are as defined herein.

In particular, $Q^{1a}$ may be selected from oxo, halo (e.g. fluoro, chloro or bromo), cyano, nitro, hydroxyl, $SR^4$ (e.g. thiol), $NR^2R^3$ (e.g. N,N-dimethylamino), $CONR^2R^3$, $C_0$-$C_3$-alkylene-$NR^4COR^5$ (e.g. N-acetyl), $NR^4CONR^5R^6$, $COR^4$ (e.g. acetyl), $C(O)OR^4$ (e.g. methoxycarbonyl or ethoxycarbonyl), $SO_2R^4$ (e.g. methyl sulphonyl), $SO_2NR^4R^5$ (e.g. dimethylaminosulphonyl), $NR^4SO_2R^5$, $NR^4SO_2NR^5R^6$, $NR^4C(O)OR^5$, optionally substituted $C_1$-$C_4$ alkyl (e.g. propyl, isobutyl or tert butyl), optionally substituted $C_1$-$C_2$ alkyl (e.g. methyl, ethyl or $CF_3$) optionally substituted $C_1$-$C_6$ alkoxy (e.g. methoxy, ethoxy or $OCF_3$) and optionally substituted $C_2$-$C_6$ alkenyl, wherein the alkyl, alkoxy, alkenyl may be unsubstituted or substituted with one or more substituents selected from $C_1$-$C_6$ alkoxy, halo, hydroxyl, thiol, cyano, amino and nitro.

$Q^{1b}$ may be selected from a covalent bond, an oxygen atom, a sulfur atom, $OR^7$, SO, $SO_2$, CO, $C(O)O$, $C_0$-$C_3$-alkylene-C(O)$NR^4$—$C_0$-$C_3$ alkylene, $C_0$-$C_3$-alkylene-$NR^4$—$C_0$-$C_3$ alkylene, $C_0$-$C_3$-alkylene-$NR^4C(O)$—$C_0$-$C_3$ alkylene, $NR^4CONR^5$, $SO_2NR^4$, $NR^4SO_2$, $NR^4SO_2NR^5$, $NR^4C(O)O$, $NR^4C(O)OR^7$, optionally substituted $C_1$-$C_6$ alkylene, or optionally substituted $C_2$-$C_6$ alkenylene, with the proviso that $Q^{1b}$ is not NH when $R^1$ is a nitrogen-containing heteroaryl ring. The alkylene or alkenylene is optionally substituted with one or more substituents selected from $C_1$-$C_6$ alkoxy, halo, hydroxyl, thiol, cyano, amino and nitro.

In particular, $Q^{1b}$ is a covalent bond.

$R^1$ represents a 3 to 10-membered monocyclic or bicyclic hetercyclyl, cycloalkyl, heteroaryl or aryl ring. $R^1$ may be selected from cyclopropyl, cyclobutyl, cyclopentyl, cyclohexyl, cycloheptyl, cyclooctyl, decahydronaphthalenyl, pyridinyl, pyrazinyl, pyrimidinyl, pyridazinyl, furanyl, thiophenyl, pyrrolyl, oxazolyl, thiazolyl, pyrazolyl, triazolyl, tetrazolyl, indolyl, indolizinyl, isoindolyl, purinyl, furazanyl, imidazolyl, indazolyl, isothiazolyl, isoxazolyl, oxadiazolyl, tetrazolyl, thiadiazolyl, benzofuranyl, isobenzofuranyl, benzothiophenyl, isobenzothiophenyl, benzimidazolyl, benzothiazolyl, benzoxazolyl, napthyridinyl, pteridinyl, pyrazinyl, quinolinyl, isoquinolinyl, cinnolinyl, phthalazinyl, quinazolinyl, imidazopyridinyl, pyrazolopyridinyl, thiazolopyridinyl, triazinyl, dihydropyridinyl, dihydropyrrolopyridinyl, quinoxalinyl, dihydrobenzoxazinyl, tetrahydropyrazinyl, azetidinyl, pyrrolidinyl, piperidinyl, azepanyl, diazepanyl, dihydrofuranyl (e.g. 2,3-dihydrofuranyl, 2,5-dihydrofuranyl), dioxolanyl, morpholinyl, oxazolidinyl, oxazinanyl, indolinyl, isoindolinyl, piperazinyl, tetrahydrofuranyl, thiomorpholinyl, dihydropyranyl (e.g. 3,4 dihydropyranyl, 3,6-dihydropyranyl), homopiperazinyl, dioxanyl, hexahydropyrimidinyl, pyrazolinyl, pyrazolidinyl, 4H-quinolizinyl, quinuclidinyl, tetrahydropyranyl, tetrahydropyridinyl, tetrahydropyrimidinyl, tetrahydrothiophenyl, thiazolidinyl, benzopyranyl, tetrahydroquinolinyl, dihydropyrrolopyridinyl, dihydrobenzoxazinyl, pyrrolopyridinyl, dihydronaphthyridinyl, dihydroisoquinolinyl and tetrahydroisoquinolinyl.

$R^1$ may represent an optionally substituted 5 or 6-membered heterocyclyl, cycloalkyl or aryl ring. Alternatively, $R^1$ may represent an optionally substituted 9 or 10-membered bicyclic heterocyclyl, cycloalkyl, heteroaryl or aryl ring.

In particular, $R^1$ is selected from substituted or unsubstituted phenyl.

In one embodiment, $R^1$ is not dihydropyrazoloxazinyl or pyrazolyl.

In all cases described herein, $R^1$ may be optionally substituted with one or more substituents independently selected from halo, cyano, oxo, nitro, hydroxyl, $SR^8$, optionally substituted $C_1$-$C_6$ alkyl, optionally substituted $C_1$-$C_6$ alkoxy, optionally substituted $C_2$-$C_6$ alkenyl, optionally substituted $C_2$-$C_6$ alkynyl, $Q^{2a}$-$R^{11}$, $Q^{2a}$-O-$Q^{2b}$-$R^{11}$, $Q^{2a}$-S-$Q^{2b}$-$R^{11}$, $Q^{2a}$-SO-$Q^{2b}$-$R^{11}$, $Q^{2a}$-$NR^8CONR^9R^{10}$, $Q^{2a}$-$NR^8CONR^9$-$Q^{2a}$-$R^{11}$, $Q^{2a}$-$NR^8R^9$, $Q^{2a}$-$NR^8$-$Q^{2b}$-$R^{11}$, $Q^{2a}$-$COR^8$, $Q^{2a}$-CO-$Q^{2b}$-$R^{11}$, $Q^{2a}$-$NR^8COR^9$, $Q^{2a}$-$NR^8CO$-$Q^{2b}$-$R^{11}$, $Q^{2a}$-$NR^8C(O)OR^9$, $Q^{2a}$-$NR^8C(O)O$-$Q^{2b}$-$R^{11}$, $Q^{2a}$-$SO_2R^8$, $Q^{2a}$-$SO_2$-$Q^{2b}$-$R^{11}$, $Q^{2a}$-$CONR^8R^9$, $Q^{2a}$-$CONR^8$-$Q^{2b}$-$R^{11}$, $Q^{2a}$-$CO_2R^8$, $Q^{2a}$-$CO_2$—$R^{11}$, $Q^{2a}$-$SO_2NR^8R^9$, $Q^{2a}$-$SO_2NR^8$-$Q^{2b}$-$R^{11}$, $Q^{2a}$-$NR^8SO_2R^9$, $Q^{2a}$-$NR^8SO_2$-$Q^{2b}$-$R^{11}$ and $Q^{2a}$-$NR^8SO_2NR^9R^9R^{10}$, $Q^{2a}$-$NR^8SO_2NR^9$-$Q^{2b}$-$R^{11}$;

wherein $Q^{2a}$ and $Q^{2b}$ each independently represent a covalent bond, optionally substituted $C_1$-$C_6$ alkylene or optionally substituted $C_2$-$C_6$ alkenylene;

$R^8$, $R^9$ and $R^{10}$ each independently represent hydrogen or optionally substituted $C_1$-$C_6$ alkyl;

and $R^{11}$ represents optionally substituted heterocyclyl, optionally substituted heteroaryl, optionally substituted aryl, or an optionally substituted cycloalkyl.

In particular, $R^1$ is unsubstituted or substituted with cyano, $Q^{2a}$-$R^{11}$ or $Q^{2a}$-O-$Q^{2b}$-$R^{11}$ wherein $Q^{2a}$ is a covalent bond, $Q^{2b}$ is a covalent bond and $R^{11}$ is phenyl, i.e. $R^1$ may be substituted with cyano, phenyl or O-phenyl.

$R^{11}$ may represent a $C_3$-$C_4$ cycloalkyl ring or a 5 or 6-membered aryl or heteroaryl ring which may be unsubstituted or substituted with a substituent selected from halo, cyano, oxo, nitro, amino, amido, hydroxyl, $C_1$-$C_6$ alkyl or $C_1$-$C_3$ alkyl, $C_1$-$C_6$ alkoxy or $C_1$-$C_3$ alkoxy, wherein the alkyl and alkoxy may be optionally substituted with halo.

In certain examples, $R^{11}$ is phenyl.

$R^1$ may be substituted with one or more (e.g. one, two, three or four), in particular one or two substituents independently selected from halo, cyano, oxo, nitro, hydroxyl, $SR^8$, optionally substituted $C_1$-$C_6$ alkyl, optionally substituted $C_1$-$C_6$ alkoxy, optionally substituted $C_2$-$C_6$ alkenyl, optionally substituted $C_2$-$C_6$ alkynyl, $Q^{2a}$-$NR^8CONR^9R^{10}$, $Q^{2a}$-$NR^8R^9$, $Q^{2a}$-$COR^8$, $Q^{2a}$-$NR^8COR^9$, $Q^{2a}$-$NR^8C(O)OR^9$, $Q^{2a}$-$SO_2R^8$, $Q^{2a}$-$CONR^8R^9$, $Q^{2a}$-$CO_2R^8$, $Q^{2a}$-$SO_2NR^8R^9$, $Q^{2a}$-$NR^8SO_2R^9$ and $Q^{2a}$-$NR^8SO_2NR^9R^{10}$;

wherein $Q^{2a}$ represents a covalent bond, optionally substituted $C_1$-$C_6$ alkylene or optionally substituted $C_2$-$C_6$ alkenylene;

$R^8$, $R^9$ and $R^{10}$ each independently represent hydrogen or optionally substituted $C_1$-$C_6$ alkyl.

$R^1$ may be unsubstituted, mono substituted or di-substituted.

In certain instances, $R^1$ represents a 3 to 10-membered heterocyclyl, cycloalkyl, heteroaryl or aryl ring selected from cyclopropyl, cyclobutyl, cyclopentyl, cyclohexyl, cycloheptyl, cyclooctyl, decahydronaphthalenyl, phenyl, naphthyl, naphthalenyl, pyridinyl, pyrazinyl, pyrimidinyl, pyridazinyl, furanyl, thiophenyl, pyrrolyl, oxazolyl, thiazolyl, pyrazolyl, triazolyl, tetrazolyl, indolyl, indolizinyl, isoindolyl, purinyl, furazanyl, imidazolyl, indazolyl, isothiazolyl, isoxazolyl, oxadiazolyl, tetrazolyl, thiadiazolyl, benzofuranyl, isobenzofuranyl, benzothiophenyl, isobenzothiophenyl, benzimidazolyl, benzothiazolyl, benzoxazolyl, napthyridinyl, pteridinyl, pyrazinyl, quinolinyl, isoquinolinyl, cinnolinyl, phthalazinyl, quinazolinyl, imidazopyridinyl, pyrazolopyridinyl, thiazolopyridinyl, triazinyl, dihydropyridinyl, dihydropyrrolopyridinyl, quinoxalinyl, dihydrobenzoxazinyl, azetidinyl, pyrrolidinyl, piperidinyl, azepanyl, diazepanyl, dihydrofuranyl (e.g. 2,3-dihydrofuranyl, 2,5-dihydrofuranyl), dioxolanyl, morpholinyl, oxazolidinyl, oxazinanyl, indolinyl, isoindolinyl, piperazinyl, tetrahydrofuranyl, thiomorpholinyl, dihydropyranyl (e.g. 3,4-dihydropyranyl, 3,6-dihydropyranyl), homopiperazinyl, dioxanyl, hexahydropyrimidinyl, pyrazolinyl, pyrazolidinyl, 4H-quinolizinyl, quinuclidinyl, tetrahydropyranyl, tetrahydropyridinyl, tetrahydropyrimidinyl, tetrahydrothiophenyl, thiazolidinyl, benzopyranyl, tetrahydroquinolinyl, dihydropyrrolopyridinyl, dihydrobenzoxazinyl, pyrrolopyridinyl, dihydronaphthyridinyl, dihydroisoquinolinyl and tetrahydroisoquinolinyl which is either unsubstituted or substituted with one or more (e.g. one, two or three) substituents selected from halo, cyano, oxo, nitro, hydroxyl, $SR^8$, optionally substituted $C_1$-$C_6$ alkyl, optionally substituted $C_1$-$C_6$ alkoxy, optionally substituted $C_2$-$C_6$ alkenyl, optionally substituted $C_2$-$C_6$ alkynyl, $Q^{2a}$-$R^{11}$, $Q^{2a}$-O-$Q^{2b}$-$R^{11}$, $Q^{2a}$-S-$Q^{2b}$-$R^{11}$, $Q^{2a}$-SO-$Q^{2b}$-$R^{11}$, $Q^{2a}$-$NR^8CONR^9R^{10}$, $Q^{2a}$-$NR^8CONR^9$-$Q^{2a}$-$R^{11}$, $Q^{2a}$-$NR^8R^9$, $Q^{2a}$-$NR^8$-$Q^{2b}$-$R^{11}$, $Q^{2a}$-$COR^8$, $Q^{2a}$-CO-$Q^{2b}$-$R^{11}$, $Q^{2a}$-$NR^8COR^9$, $Q^{2a}$-$NR^8CO$-$Q^{2b}$-$R^{11}$, $Q^{2a}$-$NR^8C(O)OR^9$, $Q^{2a}$-$NR^8C(O)O$-$Q^{2b}$-$R^{11}$, $Q^{2a}$-$SO_2R^8$, $Q^{2a}$-$SO_2$-$Q^{2b}$-$R^{11}$, $Q^{2a}$-$CONR^8R^9$, $Q^{2a}$-$CONR^8$-$Q^{2b}$-$R^{11}$, $Q^{2a}$-$CO_2R^8$, $Q^{2a}$-$CO_2$-$Q^{2b}$-$R^{11}$, $Q^{2a}$-$SO_2NR^8R^9$, $Q^{2a}$-$SO_2NR^8$-$Q^{2b}$-$R^{11}$, $Q^{2a}$-$NR^8SO_2R^9$, $Q^{2a}$-$NR^8SO_2$-$Q^{2b}$-$R^{11}$ and $Q^{2a}$-$NR^8SO_2NR^9R^{10}$, $Q^{2a}$-$NR^8SO_2NR^9$-$Q^{2b}$-$R^{11}$;

wherein $Q^{2a}$ and $Q^{2b}$ each independently represent a covalent bond, optionally substituted $C_1$-$C_6$ alkylene or optionally substituted $C_2$-$C_6$ alkenylene;

$R^8$, $R^9$ and $R^{10}$ each independently represent hydrogen or optionally substituted $C_1$-$C_6$ alkyl;

and $R^{11}$ represents optionally substituted heterocyclyl, optionally substituted heteroaryl, optionally substituted aryl, or an optionally substituted cycloalkyl.

$R^1$ may represent phenyl, wherein the phenyl ring is unsubstituted or substituted with one or more, in particular, one or two, substituents selected from halo, cyano, oxo, nitro, hydroxyl, $SR^8$, optionally substituted $C_1$-$C_6$ alkyl, optionally substituted $C_1$-$C_6$ alkoxy, optionally substituted $C_2$-$C_6$ alkenyl, optionally substituted $C_2$-$C_6$ alkynyl, $Q^{2a}$-$R^{11}$, $Q^{2a}$-O-$Q^{2b}$-$R^{11}$, $Q^{2a}$-S-$Q^{2b}$-$R^{11}$, $Q^{2a}$-SO-$Q^{2b}$-$R^{11}$, $Q^{2a}$-$NR^8CONR^9R^{10}$, $Q^{2a}$-$NR^8CONR^9$-$Q^{2a}$-$R^{11}$, $Q^{2a}$-$NR^8R^9$, $Q^{2a}$-$NR^8$-$Q^{2b}$-$R^{11}$, $Q^{2a}$-$COR^8$, $Q^{2a}$-CO-$Q^{2b}$-$R^{11}$, $Q^{2a}$-$NR^8COR^9$, $Q^{2a}$-$NR^8CO$-$Q^{2b}$-$R^{11}$, $Q^{2a}$-$NR^8C(O)OR^9$, $Q^{2a}$-$NR^8C(O)O$-$Q^{2b}$-$R^{11}$, $Q^{2a}$-$SO_2R^8$, $Q^{2a}$-$SO_2$-$Q^{2b}$-$R^{11}$, $Q^{2a}$-$CONR^8R^9$, $Q^{2a}$-$CONR^8$-$Q^{2b}$-$R^{11}$, $Q^{2a}$-$CO_2R^8$, $Q^{2a}$-$CO_2$-$Q^{2b}$-$R^{11}$, $Q^{2a}$-$SO_2NR^8R^9$, $Q^{2a}$-$SO_2NR^8$-$Q^{2b}$-$R^{11}$, $Q^{2a}$-$NR^8SO_2R^9$, $Q^{2a}$-$NR^8SO_2$-$Q^{2b}$-$R^{11}$ and $Q^{2a}$-$NR^8SO_2NR^9R^{10}$, $Q^{2a}$-$NR^8SO_2NR^9$-$Q^{2b}$-$R^{11}$;

wherein $Q^{2a}$ and $Q^{2b}$ each independently represent a covalent bond, optionally substituted $C_1$-$C_6$ alkylene or optionally substituted $C_2$-$C_6$ alkenylene;

$R^8$, $R^9$ and $R^{10}$ each independently represent hydrogen or optionally substituted $C_1$-$C_6$ alkyl;

and $R^{11}$ represents optionally substituted heterocyclyl, optionally substituted heteroaryl, optionally substituted aryl, or an optionally substituted cycloalkyl.

$R^1$ may represent phenyl, wherein the phenyl ring is unsubstituted or substituted with cyano, -$Q^{2a}$-$R^{11}$ or -$Q^{2a}$-O-$Q^{2b}R^{11}$, wherein $Q^{2a}$ and $Q^{2b}$ each represent a covalent bond and $R^{11}$ represents phenyl.

According to a second aspect of the compound of formula (I), for use in the present invention:

X is selected from O, N($R^h$), and C($R^i$)($R^j$);

$R^a$ is selected from hydrogen, fluoro, $C_1$-$C_3$ alkyl, and $C_1$-$C_3$ alkoxy; or $R^a$ is linked to $R^b$ or $R^i$ to form a $C_3$-$C_4$ cycloalkyl ring;

$R^b$, $R^c$, $R^d$ and $R^e$, are each independently selected from hydrogen and $C_1$-$C_3$ alkyl; or form one or more spirocyclic groups where $R^b$ is linked to $R^c$ or $R^d$ is linked to $R^e$, or $R^b$ is linked to $R^a$ to form a $C_3$-$C_4$ cycloalkyl ring;

$R^f$ and $R^g$, are each independently selected from hydrogen, fluoro, cyano, $C_1$-$C_3$ alkyl, and $C_1$-$C_3$ alkoxy; or form a spirocyclic group where $R^f$ is linked to $R^g$, or $R^g$ is linked to $R^i$ to form a $C_3$-$C_4$ cycloalkyl ring;

when X is O or N($R^h$), none of $R^a$, $R^f$ and $R^g$, are fluoro or $C_1$-$C_3$ alkoxy;

$R^h$ is selected from hydrogen, $C_1$-$C_3$ alkyl, C(O)$C_1$-$C_3$ alkyl, and S(O)$_2$$C_1$-$C_3$ alkyl;

$R^i$ and $R^j$ are each independently selected from hydrogen, fluoro, cyano, $C_1$-$C_3$ alkyl, and $C_1$-$C_3$ alkoxy; or form a spirocyclic group where $R^i$ is linked to $R^j$, or $R^i$ is linked to $R^a$ or $R^g$ to form a $C_3$-$C_4$ cycloalkyl ring;

ring A is a 5 to 10-membered monocyclic or bicyclic, heteroaryl or heterocyclyl ring, which is unsubstituted, or substituted with 1 to 6 $Q^1(R^1)_n$ groups, which may be the same or different;

n is 0 or 1;

$Q^1$ is selected from $Q^{1a}$ and $Q^{1b}$;

$Q^{1a}$ is selected from oxo, halo, cyano, nitro, hydroxyl, $SR^4$, $NR^2R^3$, $CONR^2R^3$, $C_0$-$C_3$-alkylene-$NR^4COR^5$, $NR^4CONR^5R^6$, $COR^4$, $C(O)OR^4$, $SO_2R^4$, $SO_2NR^4R^5$, $NR^4SO_2R^5$, $NR^4SO_2NR^5R^6$, $NR^4C(O)OR^5$, $C_1$-$C_6$ alkyl, $C_1$-$C_6$ alkoxy, and $C_2$-$C_6$ alkenyl;

$Q^{1b}$ is selected from a covalent bond, an oxygen atom, a sulfur atom, $OR^7$, SO, $SO_2$, CO, C(O)O, $C_0$-$C_3$-alkylene-C(O)$NR^4$—$C_0$-$C_3$ alkylene, $C_0$-$C_3$-alkylene-$NR^4$—$C_0$-$C_3$ alkylene, $C_0$-$C_3$ alkylene-$NR^4C(O)$—$C_0$-$C_3$ alkylene, $NR^4CONR^5$, $SO_2NR^4$, $NR^4SO_2$, $NR^4SO_2NR^5$, $NR^4C(O)O$, $NR^4C(O)OR^7$, $C_1$-$C_6$ alkylene, and $C_2$-$C_6$ alkenylene;

$R^1$ is a 3 to 10-membered monocyclic or bicyclic, heterocyclyl, heteroaryl, cycloalkyl, or aryl ring;

$R^2$, $R^3$, $R^4$, $R^5$ and $R^6$, are each independently selected from hydrogen and $C_1$-$C_6$ alkyl;

$R^7$ is $C_1$-$C_6$ alkylene;

$R^1$ is unsubstituted or substituted with 1 to 6 substituents, each independently selected from halo, cyano, oxo, nitro, hydroxyl, $C_1$-$C_6$ alkyl, $C_1$-$C_6$ alkoxy, $C_2$-$C_6$ alkenyl, $C_2$-$C_6$ alkynyl, $R^{11}$, and O—$R^{11}$; and $R^{11}$ is a 5 to 6-membered aryl or heteroaryl ring, which may be unsubstituted or substituted with 1 to 5 substituents each independently selected from halo, cyano, oxo, nitro, amino, amido, hydroxyl, $C_1$-$C_6$ alkyl, and $C_1$-$C_6$ alkoxy, wherein the alkyl and alkoxy may be optionally substituted with halo.

According to a third aspect, the present invention provides a compound of formula (I):

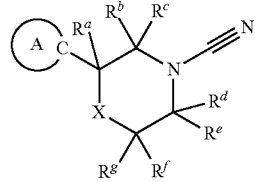

(I)

a tautomer thereof, or a pharmaceutically acceptable salt of said compound or tautomer, wherein:

X is selected from O, N($R^h$), and C($R^i$)($R^j$);

$R^a$ is selected from fluoro, $C_1$-$C_3$ alkyl, and $C_1$-$C_3$ alkoxy; or $R^a$ is linked to $R^b$ or $R^i$ to form a $C_3$-$C_4$ cycloalkyl ring;

X, $R^b$, $R^c$, $R^d$, $R^e$, $R^f$, $R^g$, $R^h$, $R^i$, $R^j$, and ring A, are as defined herein, in particular, in the first, second and third preferred embodiments of the second, third, fourth, fifth, and sixth, aspects of the invention; and when X is O or N($R^h$), none of $R^a$, $R^f$ and $R^g$, are fluoro or $C_1$-$C_3$ alkoxy.

In a preferred embodiment, X is C($R^i$)($R^j$), and most preferably, X is $CH_2$;

$R^a$ is selected from fluoro, $C_1$-$C_3$ alkyl, and $C_1$-$C_3$ alkoxy; and most preferably, $R^a$ is fluoro; and $R^i$ and $R^j$ are each independently selected from hydrogen and $C_1$-$C_3$ alkyl; and most preferably, each are hydrogen.

In another preferred embodiment, X is O; and $R^a$ is $C_1$-$C_3$ alkyl.

According to a fourth aspect, the present invention provides a compound of formula (I):

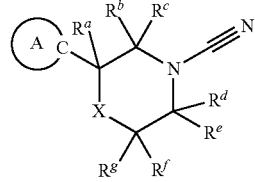

(I)

a tautomer thereof, or a pharmaceutically acceptable salt of said compound or tautomer, wherein:

ring A is a 5 to 7-membered monocyclic, heteroaryl or heterocyclyl ring, which comprises 1 to 4 heteroatoms independently selected from nitrogen, oxygen and sulfur, and is unsubstituted, or substituted with 1 to 6 $Q^1(R^1)_n$ groups, which may be the same or different; and X, $R^a$, $R^b$, $R^c$, $R^d$, $R^e$, $R^f$, $R^g$, $R^h$, $R^i$, $R^j$, $Q^1$, $R^1$, and n, are as defined herein, in particular, in the first, second and third preferred embodiments of the second, third, fourth, fifth, and sixth, aspects of the invention.

In a preferred embodiment, the heteroaryl or heterocyclyl ring is selected from pyrrolidinyl, piperidinyl, azepanyl, diazepanyl, dihydrofuranyl, 2,3-dihydrofuranyl, 2,5-dihydrofuranyl, dioxolanyl, morpholinyl, oxazolidinyl, oxazinanyl, piperazinyl, tetrahydrofuranyl, thiomorpholinyl, dihydropyranyl, 3,4-dihydropyranyl, 3,6-dihydropyranyl, homopiperazinyl, dioxanyl, hexahydropyrimidinyl, pyrazolinyl, pyrazolidinyl, tetrahydropyranyl, tetrahydropyridinyl, tetrahydropyrimidinyl, tetrahydrothiophenyl, thiazolidinyl, pyridinyl, pyrazinyl, pyrimidinyl, pyridazinyl, furanyl, thiophenyl, pyrrolyl, oxazolyl, thiazolyl, pyrazolyl, triazolyl, tetrazolyl, furazanyl, imidazolyl, isothiazolyl, isoxazolyl, oxadiazolyl, tetrazolyl, thiadiazolyl, pyrazinyl, triazinyl, dihydropyridinyl, and tetrahydropyrazinyl.

More preferably, the heteroaryl ring is selected from triazolyl, oxazolyl, and oxadiazolyl. Most preferably, the heteroaryl ring is selected from 1,3,4-triazolyl, oxazolyl, and 1-oxa-3,4-diazolyl.

According to a fifth aspect, the present invention provides a compound of formula (I):

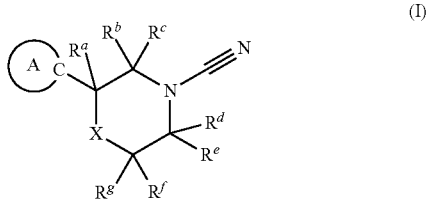

a tautomer thereof, or a pharmaceutically acceptable salt of said compound or tautomer, wherein:

ring A is a 9 to 10-membered bicyclic, heteroaryl or heterocyclyl ring, which comprises 1 to 4 heteroatoms independently selected from nitrogen, oxygen and sulfur;

when ring A is a 9-membered heteroaryl, at least one heteroatom is O or S; and ring A is unsubstituted, or substituted with 1 to 6 $Q^1(R^1)_n$ groups, which may be the same or different; and $X$, $R^a$, $R^b$, $R^c$, $R^d$, $R^e$, $R^f$, $R^g$, $R^h$, $R^i$, $R^j$, $Q^1$, $R^1$, and n, are as defined herein, in particular, in the first, second and third preferred embodiments of the second, third, fourth, fifth, and sixth, aspects of the invention.

In a preferred embodiment, the heteroaryl or heterocyclyl ring is selected from benzopyranyl, dihydrobenzoxazinyl, benzofuranyl, isobenzofuranyl, benzothiophenyl, isobenzothiophenyl, benzothiazolyl, benzoxazolyl, thiazolopyridinyl, dihydrobenzoxazinyl, oxazolopyridinyl, 4H-quinolizinyl, benzopyranyl, tetrahydroquinolinyl, dihydrobenzoxazinyl, dihydroisoquinolinyl, tetrahydroisoquinolinyl, napthyridinyl, pteridinyl, quinolinyl, isoquinolinyl, cinnolinyl, phthalazinyl, quinazolinyl, quinoxalinyl, and dihydrobenzoxazinyl.

More preferably, the heteroaryl ring is selected from oxazolopyridinyl, and benzoxazolyl. Most preferably, the heteroaryl ring is selected from oxazolo[4,5-b]pyridinyl, oxazolo[5,4-b]pyridinyl, and benzoxazolyl.

According to a sixth aspect, the present invention provides a compound of formula (I):

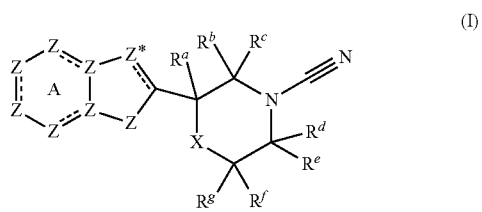

a tautomer thereof, or a pharmaceutically acceptable salt of said compound or tautomer, wherein:

ring A is a 9-membered bicyclic, heteroaryl or heterocyclyl ring, having 1 to 4 Z atoms each independently selected from nitrogen, oxygen and sulfur, and the remaining Z atoms are carbon; ring A is unsubstituted, or substituted with 1 to 6 $Q^1(R^1)_n$ groups, which may be the same or different; and $X$, $R^a$, $R^b$, $R^c$, $R^d$, $R^e$, $R^f$, $R^g$, $R^h$, $R^i$, $R^j$, $Q^1$, $R^1$, and n, are as defined herein, in particular, in the first, second and third preferred embodiments of the second, third, fourth, fifth, and sixth, aspects of the invention.

In a preferred embodiment, the heteroaryl ring is selected from indolinyl, dihydropyrrolopyridinyl, pyrrolopyridinyl, indolyl, indolizinyl, purinyl, benzofuranyl, benzothiophenyl, benzimidazolyl, benzothiazolyl, benzoxazolyl, imidazopyridinyl, thiazolopyridinyl, dihydropyrrolopyridinyl, and oxazolopyridinyl.

More preferably, the heteroaryl ring is selected from imidazopyridinyl, benzimidazolyl, oxazolopyridinyl, and benzoxazolyl. Most preferably, the heteroaryl ring is selected from imidazo[4,5-b]pyridinyl, imidazo[1,2-a]pyridinyl benzimidazolyl, oxazolo[4,5-b]pyridinyl, oxazolo[5,4-b]pyridinyl, and benzoxazolyl.

In a more preferred embodiment, Z* is nitrogen.

According to a first preferred embodiment of the second, third, fourth, fifth, and sixth, aspects of the compound of formula (I), for use in the present invention:

X is O; and $R^a$, $R^b$, $R^c$, $R^d$, $R^e$, $R^f$, and $R^g$, are each independently selected from hydrogen and $C_1$-$C_3$ alkyl. Preferably, each are independently selected from hydrogen, methyl, and ethyl. More preferably, 1, 2 or 3 are methyl, and the remainder hydrogen. Most preferably, each are hydrogen.

According to a second preferred embodiment of the second, third, fourth, fifth, and sixth, aspects of the compound of formula (I), for use in the present invention:

X is $N(R^h)$; and $R^a$, $R^b$, $R^c$, $R^d$, $R^e$, $R^f$, $R^g$, and $R^h$, are each independently selected from hydrogen and $C_1$-$C_3$ alkyl. Preferably, each are independently selected from hydrogen, methyl, and ethyl. More preferably, 1, 2, or 3 are methyl, and the remainder hydrogen. Most preferably, each are hydrogen.

According to a third preferred embodiment of the second, third, fourth, fifth, and sixth, aspects of the compound of formula (I), for use in the present invention:

X is $C(R^i)(R^j)$;

$R^a$ is selected from hydrogen, fluoro, $C_1$-$C_3$ alkyl, and $C_1$-$C_3$ alkoxy; and $R^b$, $R^c$, $R^d$, $R^e$, $R^f$, $R^g$, $R^h$, $R^i$ and $R^j$, are each independently selected from hydrogen and $C_1$-$C_3$ alkyl.

Preferably, $R^a$ is selected from hydrogen, fluoro, methyl, ethyl, methoxy, and ethoxy. More preferably, $R^a$ is selected from hydrogen and fluoro.

Preferably, $R^b$, $R^c$, $R^d$, $R^e$, $R^f$, $R^g$, $R^h$, $R^i$ and $R^j$, are each independently selected from hydrogen, methyl, and ethyl. More preferably, 1, 2 or 3 are methyl, and the remainder hydrogen. Most preferably, each are hydrogen.

In the preferred embodiments of the second, third, fourth, fifth, and sixth, aspects of the compound of formula (I), for use in the present invention:

Preferably, ring A is a 5 to 7-membered monocyclic, heteroaryl or heterocyclyl ring, or a 9 to 10-membered bicyclic, heteroaryl or heterocyclyl ring, which comprises 1 to 4 heteroatoms independently selected from nitrogen, oxygen and sulfur, and is unsubstituted, or substituted with 1 to 6 $Q^1(R^1)_n$ groups, which may be the same or different.

More preferably, ring A is selected from pyrrolidinyl, piperidinyl, azepanyl, diazepanyl, dihydrofuranyl, 2,3-dihydrofuranyl, 2,5-dihydrofuranyl, dioxolanyl, morpholinyl, oxazolidinyl, oxazinanyl, indolinyl, isoindolinyl, piperazinyl, tetrahydrofuranyl, thiomorpholinyl, dihydropyranyl, 3,4-dihydropyranyl, 3,6-dihydropyranyl, homopiperazinyl, dioxanyl, hexahydropyrimidinyl, pyrazolinyl, pyrazolidinyl, 4H-quinolizinyl, quinuclidinyl, tetrahydropyranyl, tetrahydropyridinyl, tetrahydropyrimidinyl, tetrahydrothiophenyl, thiazolidinyl, benzopyranyl, tetrahydroquinolinyl dihydropyrrolopyridinyl, dihydrobenzoxazinyl, pyrrolopyridinyl, dihydroisoquinolinyl, tetrahydroisoquinolinyl, pyridinyl, pyrazinyl, pyrimidinyl, pyridazinyl, furanyl, thiophenyl, pyrrolyl, oxazolyl, thiazolyl, pyrazolyl, triazolyl, tetrazolyl, indolyl, indolizinyl, isoindolyl, purinyl, furazanyl, imidazolyl, indazolyl, isothiazolyl, isoxazolyl, oxadiazolyl, tetrazolyl, thiadiazolyl, benzofuranyl, isobenzofuranyl, benzothiophenyl, isobenzothiophenyl, benzimidazolyl, benzothiazolyl, benzoxazolyl, napthyridinyl, pteridinyl, pyrazinyl, quinolinyl, isoquinolinyl, cinnolinyl, phthalazinyl, quinazolinyl, imidazopyridinyl, pyrazolopyridinyl, thiazolopyridinyl, triazinyl, dihydropyridinyl, dihydropyrrolopyridinyl, quinoxalinyl, dihydrobenzoxazinyl, oxazolopyridinyl, and tetrahydropyrazinyl; which is unsubstituted, or substituted with 1 to 4 $Q^1(R')_n$ groups, which may be the same or different.

Most preferably, ring A is selected from imidazopyridinyl, triazolyl, benzimidazolyl, oxazolyl, oxazolopyridinyl, benzoxazolyl, and oxadiazolyl, which is unsubstituted, or substituted with 1 to 4 $Q^1(R^1)_n$ groups, which may be the same or different.

In each of the preferred embodiments of the second, third, fourth, fifth, and sixth, aspects of the compound of formula (I), for use in the present invention:

Preferably, ring A is unsubstituted, or substituted with 1 to 6, more preferably 1 to 4, and most preferably, 1 or 2, $Q^1(R^1)_n$ groups, which may be the same or different; wherein (i) n is 0, and $Q^1$ is selected from halo, cyano, hydroxyl, methyl, ethyl, methoxy, and ethoxy; or (ii) n is 1; $Q^1$ is a covalent bond or oxygen; and $R^1$ is selected from phenyl and 5 to 6-membered monocyclic heteroaryl; wherein $R^1$ is unsubstituted, or substituted with 1 to 5 substituents, each independently selected from halo, cyano, hydroxyl, methyl, ethyl, methoxy, ethoxy, $R^{11}$, and O—$R^{11}$; and $R^{11}$ is selected from phenyl and 5 to 6-membered monocyclic heteroaryl, each of which may be unsubstituted, or substituted with 1 to 5 substituents each independently selected from halo, cyano, hydroxyl, methyl, ethyl, methoxy, and ethoxy.

In each of the preferred embodiments of the second, third, fourth, fifth, and sixth, aspects of the compound of formula (I), for use in the present invention:

More preferably, ring A is unsubstituted, or substituted with 1 to 6, more preferably 1 to 4, and most preferably, 1 or 2, $Q^1(R^1)_n$ groups, which may be the same or different; wherein (i) n is 0, and $Q^1$ is selected from fluoro, chloro, cyano, and methyl; or (ii) n is 1; $Q^1$ is a covalent bond or oxygen; and $R^1$ is selected from phenyl and 5 to 6-membered monocyclic heteroaryl, which comprises 1 to 4 heteroatoms independently selected from nitrogen, oxygen and sulfur; most preferably pyrazolyl and pyridyl; wherein $R^1$ is unsubstituted, or substituted with 1 to 5, preferably, 1, 2, or 3, substituents, each independently selected from fluoro, chloro, cyano, methyl, $R^{11}$, and O—$R^{11}$; most preferably selected from cyano, methyl, $R^{11}$, and O—$R^{11}$; and $R^{11}$ is selected from phenyl and 5 to 6-membered monocyclic heteroaryl, which comprises 1 to 4 heteroatoms independently selected from nitrogen, oxygen and sulfur; most preferably pyridyl; each of which may be unsubstituted, or substituted with 1 to 5, preferably, 1, 2, or 3, substituents, each independently selected from fluoro, chloro, cyano, and methyl, and most preferably cyano.

In an alternative aspect for all preferred embodiments of the invention, ring A is not substituted with $NH_2$ or $C(O)NH_2$, or where ring A is substituted with a nitrogen-containing heteroaryl ring, substitution is not via a NH linker; $R^2$ and $R^3$ cannot both be hydrogen; and $Q^{1b}$ is not NH when $R^1$ is a nitrogen-containing heteroaryl ring.

Preferred compounds of formula (I) according to all aspects of the present invention are selected from:

3-(6-phenyl-3H-imidazo[4,5-b]pyridin-2-yl)piperidine-1-carbonitrile;

2-(6-phenyl-3H-imidazo[4,5-b]pyridin-2-yl)morpholine-4-carbonitrile;

3-(4-(3-cyanophenyl)-1H-benzo[d]imidazol-2-yl)piperidine-1-carbonitrile;

2-(4-phenyl-1H-benzo[d]imidazol-2-yl)morpholine-4-carbonitrile;

2-(4-(3-cyanophenyl)-1H-benzo[d]imidazol-2-yl)morpholine-4-carbonitrile;

2-(3-([1,1'-biphenyl]-3-yl)-1H-1,2,4-triazol-5-yl)morpholine-4-carbonitrile;

3-(4-(2-phenoxyphenyl)oxazol-2-yl)piperidine-1-carbonitrile;

3-(4-([1,1'-biphenyl]-3-yl)oxazol-2-yl)piperidine-1-carbonitrile;

(R)-3-(5-([1,1'-biphenyl]-3-yl)-1,3,4-oxadiazol-2-yl)-3-fluoropiperidine-1-carbonitrile;

3-(5-([1,1'-biphenyl]-4-yl)-1,3,4-oxadiazol-2-yl)-3-fluoropiperidine-1-carbonitrile;

(R)-4-(5-(1-cyano-3-fluoropiperidin-3-yl)-1,3,4-oxadiazol-2-yl)-[2,4'-bipyridine]-2'-carbonitrile;

(R)-4-(5-(1-cyano-3-fluoropiperidin-3-yl)-1,3,4-oxadiazol-2-yl)picolinonitrile;

(R)-2'-(5-(1-cyano-3-fluoropiperidin-3-yl)-1,3,4-oxadiazol-2-yl)-[4,4'-bipyridine]-2-carbonitrile;

3-(6-(1H-pyrazol-5-yl)-1H-benzo[d]imidazol-2-yl)-3-fluoropiperidine-1-carbonitrile;

(R)-3-fluoro-3-(5-phenyl-3H-imidazo[4,5-b]pyridin-2-yl)piperidine-1-carbonitrile;

(S)-3-(5-(3-cyanophenyl)-3H-imidazo[4,5-b]pyridin-2-yl)-3-fluoropiperidine-1-carbonitrile;

3-(5-(1H-pyrazol-5-yl)-3H-imidazo[4,5-b]pyridin-2-yl)-3-fluoropiperidine-1-carbonitrile;

(R)-4-(2-(1-cyano-3-fluoropiperidin-3-yl)-3H-imidazo[4,5-b]pyridin-6-yl)picolinonitrile;

(R)-4-(2-(1-cyano-3-fluoropiperidin-3-yl)-1H-imidazo[4,5-b]pyridin-5-yl)picolinonitrile;

3-(6-(3-cyanophenyl)-1H-imidazo[4,5-b]pyridin-2-yl)-3-fluoropiperidine-1-carbonitrile;

(R)-6-(2-(1-cyano-3-fluoropiperidin-3-yl)-3H-imidazo[4,5-b]pyridin-5-yl)picolinonitrile;

(R)-3-(5-(3-cyanophenyl)benzo[d]oxazol-2-yl)-3-fluoropiperidine-1-carbonitrile;

(R)-6-(2-(1-cyano-3-fluoropiperidin-3-yl)benzo[d]oxazol-5-yl)pyrimidine-4-carbonitrile;

(R)-2-(2-(1-cyano-3-fluoropiperidin-3-yl)benzo[d]oxazol-5-yl)pyrimidine-4-carbonitrile;

(R)-4-(2-(1-cyano-3-fluoropiperidin-3-yl)benzo[d]oxazol-5-yl)picolinonitrile;

(R)-2-(2-(1-cyano-3-fluoropiperidin-3-yl)benzo[d]oxazol-5-yl)isonicotinonitrile;

(R)-4-(2-(1-cyano-3-fluoropiperidin-3-yl)benzo[d]oxazol-6-yl)picolinonitrile;

3-(6-(3-cyanophenyl)oxazolo[5,4-b]pyridin-2-yl)-3-fluoropiperidine-1-carbonitrile;

3-(6-(3-cyanophenyl)oxazolo[4,5-b]pyridin-2-yl)-3-fluoropiperidine-1-carbonitrile;

(R)-4-(2-(1-cyano-3-fluoropiperidin-3-yl)oxazolo[5,4-b]pyridin-6-yl)picolinonitrile; and (R)-4-(2-(1-cyano-3-fluoropiperidin-3-yl)imidazo[1,2-a]pyridin-7-yl)picolinonitrile;

or pharmaceutically acceptable salts thereof.

Pharmaceutical acceptable salts of the compounds of formula (I) include the acid addition and base salts (including di-salts) thereof.

Suitable acid addition salts are formed from acids which form non-toxic salts.

Examples include the acetate, aspartate, benzoate, besylate, bicarbonate/carbonate, bisulfate, camsylate, citrate, edisylate, esylate, fumarate, gluceptate, gluconate, glucuronate, hibenzate, hydrochloride/chloride, hydrobromide/bromide, hydroiodide/iodide, hydrogen phosphate, isethionate, D and L-lactate, malate, maleate, malonate, mesylate, methylsulfate, 2-napsylate, nicotinate, nitrate, orotate, palmate, phosphate, saccharate, stearate, succinate sulfate, D- and L-tartrate, and tosylate salts.

Suitable base salts are formed from bases which form non-toxic salts. Examples include the aluminium, ammonium, arginine, benzathine, calcium, choline, diethylamine, diolamine, glycine, lysine, magnesium, meglumine, olamine, potassium, sodium, tromethamine and zinc salts.

For a review on suitable salts, see Stahl and Wermuth, Handbook of Pharmaceutical Salts: Properties, Selection, and Use, Wiley-VCH, Weinheim, Germany (2002).

A pharmaceutical acceptable salt of a compound of formula (I) may be readily prepared by mixing together solutions of the compound of formula (I) and the desired acid or base, as appropriate. The salt may precipitate from solution and be collected by filtration or may be recovered by evaporation of the solvent.

Pharmaceutical acceptable solvates in accordance with the invention include hydrates and solvates wherein the solvent of crystallization may be isotopically substituted, e.g. D2O, acetone-d6, DMSO-d6.

Also within the scope of the invention are clathrates, drug-host inclusion complexes wherein, in contrast to the aforementioned solvates, the drug and host are present in non-stoichiometric amounts. For a review of such complexes, see J. Pharm Sci, 64 (8), 1269-1288 by Haleblian (August 1975).

Hereinafter all references to compounds of formula (I) include references to salts thereof and to solvates and clathrates of compounds of formula (I) and salts thereof.

The invention includes all polymorphs of the compounds of formula (I) as hereinbefore defined.

Also within the scope of the invention are so-called "prodrugs" of the compounds of formula (I). Thus, certain derivatives of compounds of formula (I) which have little or no pharmacological activity themselves can, when metabolised upon administration into or onto the body, give rise to compounds of formula (I) having the desired activity. Such derivatives are referred to as "prodrugs".

Prodrugs in accordance with the invention can, for example, be produced by replacing appropriate functionalities present in the compounds of formula (I) with certain moieties known to those skilled in the art as "pro-moieties" as described, for example, in "Design of Prodrugs" by H Bundgaard (Elsevier, 1985).

Finally, certain compounds of formula (I) may themselves act as prodrugs of other compounds of formula (I).

Certain derivatives of compounds of formula (I) which contain a nitrogen atom may also form the corresponding N-oxide, and such compounds are also within the scope of the present invention.

Compounds of formula (I) containing one or more asymmetric carbon atoms can exist as two or more optical isomers. Where a compound of formula (I) contains an alkenyl or alkenylene group, geometric cis/trans (or Z/E) isomers are possible, and where the compound contains, for example, a keto or oxime group, tautomeric isomerism ('tautomerism') may occur. It follows that a single compound may exhibit more than one type of isomerism.

Included within the scope of the present invention are all optical isomers, geometric isomers and tautomeric forms of the compounds of formula, including compounds exhibiting more than one type of isomerism, and mixtures of one or more thereof.

Cis/trans isomers may be separated by conventional techniques well known to those skilled in the art, for example, fractional crystallisation and chromatography.

Conventional techniques for the preparation/isolation of individual enantiomers include chiral synthesis from a suitable optically pure precursor or resolution of the racemate (or the racemate of a salt or derivative) using, for example, chiral high performance liquid chromatography (HPLC). Alternatively, the racemate (or a racemic precursor) may be reacted with a suitable optically active compound, for example, an alcohol, or, in the case where the compound of formula (I) contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person. Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture. The present invention includes all crystal forms of the compounds of formula (I) including racemates and racemic mixtures (conglomerates) thereof. Stereoisomeric conglomerates may be separated by conventional techniques known to those skilled in the art—see, for example, "Stereochemistry of Organic Compounds" by E. L. Eliel and S. H. Wilen (Wiley, New York, 1994).

In particular, the compounds of formula (I) contain a chiral centre at the carbon atom of the ring that is substituted by $R^a$, and said stereocentre can thus exist in either the (R) or (S) configuration. The designation of the absolute configuration (R) and (S) for stereoisomers in accordance with IUPAC nomenclature is dependent on the nature of the substituents and application of the sequence-rule procedure. The compounds of formula (I) may thus exist in either of the following enantiomeric configurations:

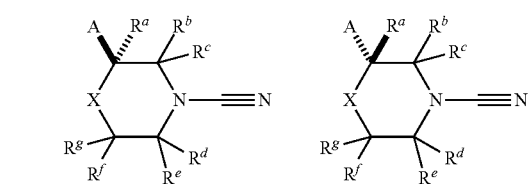

In a preferred aspect, the compounds of formula (I) possess the absolute stereochemical configuration:

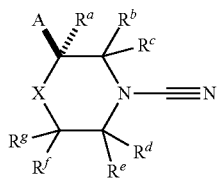

In another preferred aspect, the compounds of formula (I) possess the absolute stereochemical configuration:

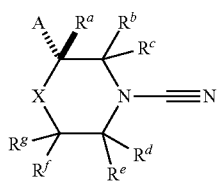

Included within the scope of the present invention are each of these (R) and (S) stereoisomers of the compounds of formula (I) in individual form, or mixtures thereof. When the compound of formula (I) is isolated as a single stereoisomer, the compound may exist with an enantiomeric excess of at least 80%, preferably at least 90%, more preferably at least 95%, for example 96%, 96%, 98%, 99%, or 100%.

According to a further aspect of the invention there is provided a process for the preparation of a compound of formula (I) or a pharmaceutically acceptable salt thereof comprising the steps of reacting an amine of formula II with cyanogen bromide to form N—CN compounds of formula (I):

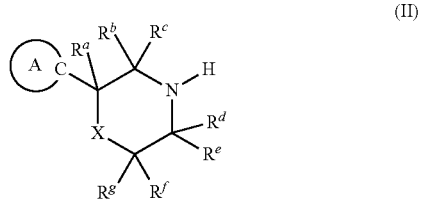

(II)

wherein $R^a$, $R^b$, $R^c$, $R^d$, $R^e$, $R^f$, $R^g$, X and ring A are as defined herein.

According to a further aspect of the invention there is provided a compound of formula (II) wherein $R^a$, $R^b$, $R^c$, $R^d$, $R^e$, $R^f$, $R^g$, X and ring A are as defined herein, and the individual isomers thereof.

The present invention also includes all pharmaceutically acceptable isotopic variations of a compound of formula (I). An isotopic variation is defined as one in which at least one atom is replaced by an atom having the same atomic number, but an atomic mass different from the atomic mass usually found in nature.

Examples of isotopes suitable for inclusion in the compounds of the invention include isotopes of hydrogen, such as $^2H$ and $^3H$, carbon, such as $^{13}C$ and $^{14}C$, nitrogen, such as $^{15}N$, oxygen, such as $^{17}O$ and $^{18}O$, phosphorus, such as $^{32}P$, sulfur, such as $^{35}S$, fluorine, such as $^{18}F$, and chlorine, such as $^{36}Cl$.

The isotopes may be radioactive or non-radioactive. In one embodiment, the compounds contain no radioactive isotopes. Such compounds are preferred for therapeutic use. In another embodiment, however, the compounds may contain one or more radioisotopes. Compounds containing such radioisotopes may be useful in a diagnostic context.

Certain isotopically labelled compounds of formula (I), for example, those incorporating a radioactive isotope, are useful in drug and/or substrate tissue distribution studies. The radioactive isotopes i.e. $^3H$ and $^{14}C$ are particularly useful for this purpose in view of their ease of incorporation and ready means of detection. Substitution with heavier isotopes i.e. $^2H$, may afford certain therapeutic advantages resulting from greater metabolic stability, for example, increased in vivo half-life or reduced dosage requirements, and hence may be preferred in some circumstances. Substitution with positron emitting isotopes, such as $^{11}C$, $^{18}F$, $^{15}O$ and $^{13}N$, can be useful in Positron Emission Topography (PET) studies for examining receptor occupancy. Isotopically labelled compounds of formula (I) can generally be prepared by conventional techniques known to those skilled in the art or by processes analogous to those described in the accompanying examples and preparations using an appropriate isotopically labelled reagent in place of the non-labelled reagent previously employed.

The compounds of formula (I) may exist in crystalline or amorphous form and some of the crystalline forms may exist as polymorphs, which are included within the scope of the present invention. Polymorphic forms of compounds of formula (I) may be characterised and differentiated using a number of conventional analytical techniques, including, but not limited to, infra-red spectra, Raman spectra, X-ray powder diffraction, differential scanning calorimetry, thermogravimetric analysis and solid state nuclear magnetic resonance.

Accordingly, in further embodiments, the invention provides a compound according to any described embodiments in a crystalline form. The compound may be from 50% to 100% crystalline, and more particularly is at least 50% crystalline, or at least 60% crystalline, or at least 70% crystalline, or at least 80% crystalline, or at least 90% crystalline, or at least 95% crystalline, or at least 98% crystalline, or at least 99% crystalline, or at least 99.5% crystalline, or at least 99.9% crystalline, for example 100% crystalline. The compound may alternatively be in an amorphous form.

The invention described herein relates to all crystal forms, solvates and hydrates of any of the disclosed compounds however so prepared. To the extent that any of the compounds disclosed herein have acid or basic centres such as carboxylates or amino groups, then all salt forms of said compounds are included herein. In the case of pharmaceutical uses, the salt should be seen as being a pharmaceutically acceptable salt.

The invention relates to any solvates of the compounds and their salts. Preferred solvates are solvates formed by the incorporation into the solid state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulfoxide. Solvates can be prepared by recrystallising the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGE), differential scanning calorimetry (DSC) and X-ray crystallography.

The solvates can be stoichiometric or non-stoichiometric solvates. Particular solvates may be hydrates, and examples of hydrates include hemihydrates, monohydrates and dihydrates. For a more detailed discussion of solvates and the methods used to make and characterise them, see Bryn et al., Solid-State Chemistry of Drugs, Second Edition, published by SSCI, Inc of West Lafayette, Ind., USA, 1999, ISBN 0-967-06710-3.

Compounds of the invention may be metabolised in vivo. Metabolites of compounds of formula (I) are also within the scope of the present invention. The term 'metabolites' refers to all molecules derived from any of the compounds according to the present invention in a cell or organism, preferably mammal. Preferably the term relates to molecules which differ from any molecule which is present in any such cell or organism under physiological conditions.

A treatment defined herein may be applied as a sole therapy of may involve, in addition to the compounds of the invention, conventional surgery or radiotherapy or chemotherapy. Furthermore, compounds of formula (I) can also be used in combination with existing therapeutic agents for the treatment of conditions associated with cancer, including small molecule therapeutics or antibody based therapeutics.

According to a further aspect, the present invention provides a pharmaceutical composition comprising a compound of formula (I) as defined herein, or a pharmaceutically acceptable salt of said compound or tautomer, together with a pharmaceutically acceptable diluent or carrier.

Pharmaceutical compositions of the invention comprise any of the compounds of the invention combined with any pharmaceutically acceptable carrier, adjuvant or vehicle. Examples of pharmaceutically acceptable carriers are known to those skilled in the art and include, but are not limited to, preserving agents, fillers, disintegrating agents, wetting agents, emulsifying agents, suspending agents, sweetening agents, flavouring agents, perfuming agents, antibacterial agents, antifungal agents, lubricating agents and dispersing agents, depending on the nature of the mode of administration and dosage forms. The compositions may be in the form of, for example, tablets, capsules, powders, granules, elixirs, lozenges, suppositories, syrups and liquid preparations including suspensions and solutions. The term "pharmaceutical composition" in the context of this invention means a composition comprising an active agent and comprising additionally one or more pharmaceutically acceptable carriers. The composition may further contain ingredients selected from, for example, diluents, adjuvants, excipients, vehicles, preserving agents, fillers, disintegrating agents, wetting agents, emulsifying agents, suspending agents, sweetening agents, flavouring agents, perfuming agents, antibacterial agents, antifungal agents, lubricating agents and dispersing agents, depending on the nature of the mode of administration and dosage forms.

The compounds of formula (I) are inhibitors of the deubiquitylating enzyme USP30.

According to a further aspect, the present invention provides a compound of formula (I) as defined herein, a tautomer thereof, or a pharmaceutically acceptable salt of said compound or tautomer for use as a medicament.

According to a further aspect, the present invention provides a method of treatment of a disorder or condition where inhibition of USP30 is known, or can be shown, to produce a beneficial effect, in a mammal, comprising administering to said mammal a therapeutically effective amount of a compound of formula (I) as defined herein, a tautomer thereof, or a pharmaceutically acceptable salt of said compound or tautomer.

According to a further aspect, the present invention provides the use of a compound of formula (I) as defined herein, a tautomer thereof, or a pharmaceutically acceptable salt of said compound or tautomer, in the preparation of a medicament for the treatment of a disorder or condition where inhibition of USP30 is known, or can be shown, to produce a beneficial effect.

The term "treat" or "treating" or "treatment" includes prophylaxis and means to ameliorate, alleviate symptoms, eliminate the causation of the symptoms either on a temporary or permanent basis, or to prevent or slow the appearance of symptoms of the named disorder or condition. The compounds of the invention are useful in the treatment of humans and non-human animals.

The dose of the compound is that amount effective to prevent occurrence of the symptoms of the disorder or to treat some symptoms of the disorder from which the patient suffers. By "effective amount" or "therapeutically effective amount" or "effective dose" is meant that amount sufficient to elicit the desired pharmacological or therapeutic effects, thus resulting in effective prevention or treatment of the disorder. Prevention of the disorder is manifested by delaying the onset of the symptoms of the disorder to a medically significant extent. Treatment of the disorder is manifested by a decrease in the symptoms associated with the disorder or an amelioration of the reoccurrence of the symptoms of the disorder.

The disorder or condition benefiting from USP30 activity is selected from a condition involving mitochondrial dysfunction, and cancer.

In one preferred embodiment of all aspects of the invention, the disorder or condition benefiting from USP30 activity is a condition involving mitochondrial dysfunction.

Mitochondrial dysfunctions result from defects of the mitochondria, which are specialized compartments present in every cell of the body except red blood cells. When mitochondria fail, less and less energy is generated within the cell and cell injury or even cell death will follow. If this process is repeated throughout the body the life of the subject in whom this is happening is severely compromised. Diseases of the mitochondria appear most often in organs that are very energy demanding such as the brain, heart, liver, skeletal muscles, kidney and the endocrine and respiratory system.

The condition involving mitochondrial dysfunction may be selected from a condition involving a mitophagy defect, a condition involving a mutation in mitochondrial DNA, a condition involving mitochondrial oxidative stress, a condition involving a defect in mitochondrial membrane potential, mitochondrial biogenesis, a condition involving a defect in mitochondrial shape or morphology, and a condition involving a lysosomal storage defect.

In particular, the condition involving mitochondrial dysfunction may be selected from a neurodegenerative disease; multiple sclerosis (MS); mitochondrial myopathy; encephalopathy; lactic acidosis; stroke-like episodes (MELAS) syndrome; Leber's hereditary optic neuropathy (LHON); cancer (including, for example, breast, ovarian, prostate, lung, kidney, gastric, colon, testicular, head and neck, pancreas, brain, melanoma, bone or other cancers of tissue organs and cancers of the blood cells, such as lymphoma and leukaemia; multiple myeloma, colorectal cancer, and non-small cell lung carcinoma); neuropathy, ataxia, retinitis pigmentosa, maternally inherited Leigh syndrome (NARP-MILS);

Danon disease; diabetes; diabetic nephropathy; metabolic disorders; heart failure; ischemic heart disease leading to myocardial infarction; psychiatric diseases, for example schizophrenia; multiple sulfatase deficiency (MSD); mucolipidosis II (ML II); mucolipidosis III (ML III); mucolipidosis IV (ML IV); GMl-gangliosidosis (GM1); neuronal ceroid-lipofuscinoses (NCL1); Alpers disease; Barth syndrome; Beta-oxidation defects; carnitine-acyl-carnitine deficiency; carnitine deficiency; creatine deficiency syndromes; co-enzyme Q10 deficiency; complex I deficiency; complex II deficiency; complex III deficiency; complex IV deficiency; complex V deficiency; COX deficiency; chronic progressive external ophthalmoplegia syndrome (CPEO); CPT I deficiency; CPT II deficiency; glutaric aciduria type II; Kearns-Sayre syndrome; lactic acidosis; long-chain acyl-CoA dehydrogenase deficiency (LCHAD); Leigh disease or syndrome; lethal infantile cardiomyopathy (LIC); Luft disease; glutaric aciduria type II; medium-chain acyl-CoA dehydrogenase deficiency (MCAD); myoclonic epilepsy and ragged-red fiber (MERRF) syndrome; mitochondrial cytopathy; mitochondrial recessive ataxia syndrome; mitochondrial DNA depletion syndrome; myoneurogastrointestinal disorder and encephalopathy; Pearson syndrome; pyruvate dehydrogenase deficiency; pyruvate carboxylase deficiency; POLG mutations; medium/short-chain 3-hydroxyacyl-CoA dehydrogenase (M/SCHAD) deficiency; very long-chain acyl-CoA dehydrogenase (VL-CAD) deficiency; and age-dependent decline in cognitive function and muscle strength.

The condition involving mitochondrial dysfunction may be a CNS disorder, for example a neurodegenerative disease.

Neurodegenerative diseases include, but are not limited to, Parkinson's disease, Alzheimer's disease, amyotrophic lateral sclerosis (ALS), Huntington's disease, ischemia, stroke, dementia with Lewy bodies, and frontotemporal dementia.

In particular, the compounds of the invention may be useful in the treatment of Parkinson's disease, including, but not limited to, PD related to mutations in α-synuclein, parkin and PINK1, autosomal recessive juvenile Parkinson's disease (AR-JP) where parkin is mutated.

The compounds of the invention or pharmaceutical compositions thereof as described herein may be combined with one or more additional agents when used for the treatment of conditions involving mitochondrial dysfunction. The compounds may be combined with one or more additional agents selected from levodopa, a dopamine agonist, a monoamino oxygenase (MAO) B inhibitor, a catechol O-methyltransferase (COMT) inhibitor, an anticholinergic, riluzole, amantadine, a cholinesterase inhibitor, memantine, tetrabenazine, an antipsychotic, diazepam, clonazepam, an antidepressant, and an anti-convulsant.

In another preferred embodiment of all aspects of the invention, the disorder or condition benefiting from USP30 activity is cancer. The cancer may be linked to mitochondrial dysfunction. Preferred cancers include, for example, breast, ovarian, prostate, lung, kidney, gastric, colon, testicular, head and neck, pancreas, brain, melanoma, bone or other cancers of tissue organs and cancers of the blood cells, such as lymphoma and leukaemia, multiple myeloma, colorectal cancer, and non-small cell lung carcinoma.

In particular, the compounds of the invention may be useful in the treatment of cancer where apoptotic pathways are dysregulated and more particularly where proteins of the BCL-2 family are mutated, or over or under expressed.

References to 'treatment' includes curative, palliative and prophylactic, and includes means to ameliorate, alleviate symptoms, eliminate the causation of the symptoms either on a temporary or permanent basis, or to prevent or slow the appearance of symptoms of the named disorder or condition. The compounds of the invention are useful in the treatment of humans and other mammals.

The compounds of the invention or pharmaceutical compositions thereof, as described herein, may be used alone or combined with one or more additional pharmaceutical agents. The compounds may be combined with an additional anti-tumour therapeutic agent, for example, chemotherapeutic drugs or inhibitors of other regulatory proteins. In one embodiment, the additional anti-tumour therapeutic agent is a BH-3 mimetic. In a further embodiment, BH-3 mimetics may be selected from but not limited to one or more of ABT-737, ABT-199, ABT-263, and Obatoclax. In a further embodiment, the additional anti-tumour agent is a chemotherapeutic agent. Chemotherapeutic agents may be selected from but not limited to, olaparib, mitomycin C, cisplatin, carboplatin, oxaliplatin, ionizing radiation (IR), camptothecin, irinotecan, topotecan, temozolomide, taxanes, 5-fluoropyrimidines, gemcitabine, and doxorubicin.

The pharmaceutical compositions of the invention may be administered in any suitably effective manner, such as oral, parenteral, topical, inhaled, intranasal, rectal, intravaginal, ocular, and andial. Pharmaceutical compositions suitable for the delivery of compounds of the present invention and methods for their preparation will be readily apparent to those skilled in the art. Such compositions and methods for their preparation may be found, for example, in "Remington's Pharmaceutical Sciences", 19th Edition (Mack Publishing Company, 1995).

Oral Administration

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, lozenges (including liquid-filled), chews, multi- and nano-particulates, gels, films (including muco-adhesive), ovules, sprays and liquid formulations.

Liquid formulations include suspensions, solutions, syrups and elixirs. Such formulations may be employed as fillers in soft or hard capsules and typically comprise a carrier, for example, water, ethanol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986 by Liang and Chen (2001).

A typical tablet may be prepared using standard processes known to a formulation chemist, for example, by direct compression, granulation (dry, wet, or melt), melt congealing, or extrusion. The tablet formulation may comprise one or more layers and may be coated or uncoated.

Examples of excipients suitable for oral administration include carriers, for example, cellulose, calcium carbonate, dibasic calcium phosphate, mannitol and sodium citrate, granulation binders, for example, polyvinylpyrrolidine, hydroxypropylcellulose, hydroxypropylmethylcellulose and gelatin, disintegrants, for example, sodium starch glycolat and silicates, lubricating agents, for example, magnesium stearate and stearic acid, wetting agents, for example, sodium lauryl sulphate, preservatives, anti-oxidants, flavours and colourants.

Solid formulations for oral administration may be formulated to be immediate and/or modified release. Modified release formulations include delayed-, sustained-, pulsed-, controlled dual-, targeted and programmed release. Details of suitable modified release technologies such as high energy dispersions, osmotic and coated particles are to be found in Verma et al, Pharmaceutical Technology On-line, 25 (2), 1-14 (2001). Other modified release formulations are described in U.S. Pat. No. 6,106,864.

Parenteral Administration

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (I) used in the preparation of parenteral solutions may be increased by suitable processing, for example, the use of high energy spray-dried dispersions (see WO 01/47495) and/or by the use of appropriate formulation techniques, such as the use of solubility-enhancing agents.

Formulations for parenteral administration may be formulated to be immediate and/or modified release. Modified release formulations include delayed-, sustained-, pulsed-, controlled dual-, targeted and programmed release.

Pharmaceutical compositions of the present invention also include compositions and methods known in the art for bypassing the blood brain barrier or can be injected directly into the brain. Suitable areas for injection include the cerebral cortex, cerebellum, midbrain, brainstem, hypothalamus, spinal cord and ventricular tissue, and areas of the PNS including the carotid body and the adrenal medulla.

Dosage

The magnitude of an effective dose of a compound will, of course, vary with the nature of the severity of the condition to be treated and the route of administration. The selection of appropriate dosages is within the remit of the physician. The daily dose range is about 10 µg to about 100 mg per kg body weight of a human and non-human animal and in general may be around 10 µg to 30 mg per kg body weight per dose. The above dose may be given from one to three times per day.

For example, oral administration may require a total daily dose of from 5 mg to 1000 mg, such as from 5 to 500 mg, while an intravenous dose may only require from 0.01 to 30 mg/kg body weight, such as from 0.1 to 10 mg/kg, more preferably from 0.1 to 1 mg/kg body weight. The total daily dose may be administered in single or divided doses.

The skilled person will also appreciate that, in the treatment of certain conditions, compounds of the invention may be taken as a single dose on an "as required" basis (i.e. as needed or desired).

Synthetic Methodologies

Compounds of formula (I) may be prepared using methods as described below in the general reaction schemes and the representative examples. Where appropriate, the individual transformations within a scheme may be completed in a different order.

All of the compounds were characterised by liquid chromatography-mass spectroscopy (LCMS) or $^1$H NMR or both.

ABBREVIATIONS

CDI Carbonyldiimidazole
d Doublet (NMR signal)
DCM Dichloromethane
DIAD Diisopropyl azodicarboxylate
DIPEA Diisopropylethylamine
DMA Dimethylacetamide
DME 1,2-Dimethoxyethane
DMF N,N-Dimethylformamide
DMSO Dimethylsulphoxide
dppf 1,1'-Bis(diphenylphosphino)ferrocene
EDC 1-Ethyl-3-(3-dimethylaminopropyl)carbodiimide
ES Electrospray
EtOAc Ethyl acetate
EtOH Ethanol
h Hour(s)
m Multiplet (NMR signal)
MeCN Acetonitrile
MeOH Methanol
min Minute(s)
NaOEt Sodium ethoxide
psi Pounds per square inch
PTS Para toluene sulfonyl
rt Room temperature
s Singlet (NMR signal)
TBTU O-(Benzotriazol-1-yl)-N,N,N',N'-tetramethyluronium tetrafluoroborate
T3P 2,4,6-Tripropyl-1,3,5,2,4,6-trioxatriphosphorinane-2,4,6-trioxide
TEA Triethylamine
TFA Trifluoroacetic acid
THF Tetrahydrofuran
TMS Trimethylsilyl Analytical Methods:

| Method A | |
|---|---|
| Column | X-bridge C18, 50 × 4.6 mm, 3.5 µm or equivalent |
| Mobile Phase | (A) 0.1% Ammonia in water; (B) 0.1% Ammonia in MeCN |
| Flow Rate | 1.0 ml/min |

| | Time | % B |
|---|---|---|
| Gradient | 0.01 | 5 |
| | 5.00 | 90 |
| | 5.80 | 95 |
| | 7.20 | 95 |

| Method B | |
|---|---|
| Column | BEH C18, 50 × 2.1 mm, 1.7 μm or equivalent |
| Mobile Phase | (A) 5 mM Ammonium acetate + 0.1% formic acid in water<br>(B) 0.1% Formic acid in MeCN |
| Flow Rate | 0.45 ml/min |
| Gradient | Time | % B |
| | 0.01 | 2 |
| | 0.50 | 2 |
| | 5.00 | 90 |
| | 6.00 | 95 |
| | 7.00 | 95 |

| Method C | |
|---|---|
| Column | BEH C18, 50 × 2.1 mm, 1.7 μm or equivalent |
| Mobile Phase | (A) 5 mM Ammonium acetate + 0.1% formic acid in water<br>(B) 0.1% Formic acid in MeCN |
| Flow Rate | 0.55 ml/min |
| Gradient | Time | % B |
| | 0.01 | 5 |
| | 0.40 | 5 |
| | 0.80 | 35 |
| | 1.20 | 55 |
| | 2.50 | 100 |
| | 3.30 | 100 |

EXAMPLE 1

3-(6-Phenyl-3H-imidazo[4,5-b]pyridin-2-yl)piperidine-1-carbonitrile

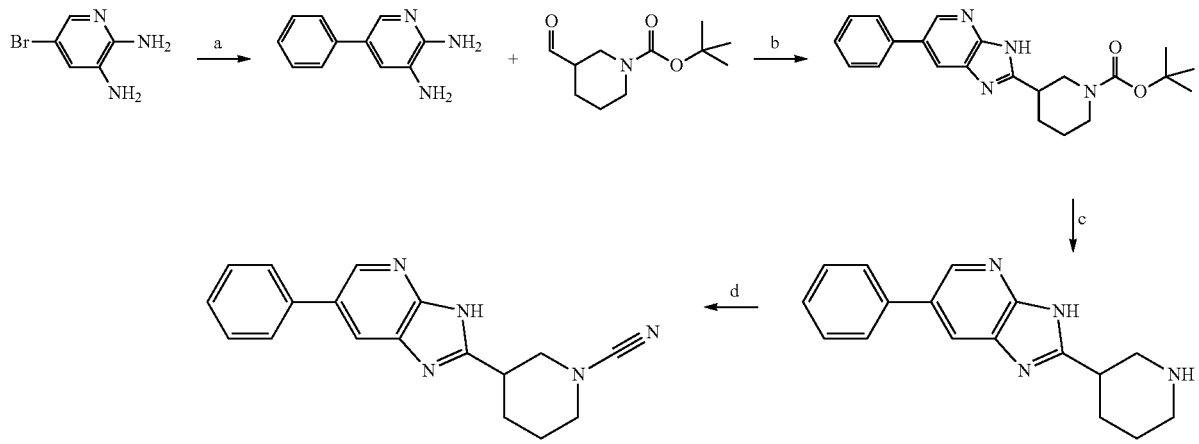

Step a.

To a solution of 5-bromopyridine-2,3-diamine (CAS Number 38875-53-5; 1.000 g, 5.32 mmol) in 1,4-dioxane:water (7:3, 13 ml) were added $Na_2CO_3$ (1.691 g, 15.957 mmol) and phenylboronic acid (1.297 g, 10.64 mmol) at rt. The reaction mixture was degassed for 10 min before addition of Pd(Ph$_3$)$_4$ (0.307 g, 0.265 mmol). The reaction mixture was heated at 90° C. for 16 h. The resulting mixture was cooled to rt and diluted with water (50 ml). The resulting mixture was extracted with EtOAc (3×50 ml). The combined organic phase was dried over anhydrous $Na_2SO_4$, filtered and concentrated under reduced pressure. The resulting residue was purified by flash column chromatography (4% MeOH in DCM) yielding 5-phenylpyridine-2,3-diamine (1.3 g, quantitative). LCMS: Method C, 1.474 min, MS: ES+ 186.2.

Step b.

To a solution of 5-phenylpyridine-2,3-diamine (0.208 g, 1.125 mmol) in dry DMF (5 ml) were added tert-butyl 3-formylpiperidine-1-carboxylate (CAS Number 118156-93-7; 0.300 g, 1.406 mmol) and sodium metabisulphite (0.267 g, 1.406 mmol) at rt. The reaction mixture was heated at 120° C. for 16 h. The resulting mixture was cooled to rt and diluted with water (25 ml) and extracted with EtOAc (3×25 ml). The combined organic phase was dried over anhydrous $Na_2SO_4$, filtered and concentrated under reduced pressure. The resulting residue was purified by flash column chromatography (36% EtOAc in hexane) yielding tert-butyl 3-(6-phenyl-3H-imidazo[4,5-b]pyridin-2-yl)piperidine-1-carboxylate (0.100 g, 0.264 mmol), LCMS: Method A, 4.405 min, MS: ES+ 379.13.

Step c.

To a solution of tert-butyl 3-(6-phenyl-3H-imidazo[4,5-b]pyridin-2-yl)piperidine-1-carboxylate (0.100 g, 0.264 mmol) in DCM (5 ml) was added TFA (0.5 ml) at 0° C. The reaction mixture was stirred at rt for 1.5 h. The resulting reaction mixture was concentrated under reduced pressure and azeotropically distilled using DCM (20 ml). The obtained material was dried under vacuum yielding 6-phenyl-2-(piperidin-3-yl)-3H-imidazo[4,5-b]pyridine TFA salt (0.1 g, quantitative). LCMS: Method A, 3.389 min, MS: ES+ 279.13.

Step d.

To a solution of 6-phenyl-2-(piperidin-3-yl)-3H-imidazo[4,5-b]pyridine TFA salt (0.100 g, 0.254 mmol) in THF (5 ml) was added $K_2CO_3$ (0.073 g, 0.508 mmol) at rt. Cyanogen bromide (0.033 g, 0.305 mmol) was added to the reaction mixture at rt. The reaction mixture was stirred at rt for 30 min. The resulting mixture was poured into water (20 ml) and extracted with EtOAc (3×20 ml). The combined organic phase was dried over $Na_2SO_4$, filtered and concentrated under reduced pressure. The residue was purified by flash column chromatography (95% EtOAc in hexane) yielding the title compound. LCMS: Method A, 3.469 min, MS: ES+ 304.1; $^1$H NMR (400 MHz, DMSO-d6) δ ppm: 12.63-12.95 (m, 1H), 8.56-8.64 (m, 1H), 8.06-8.21 (m, 1H), 7.72-7.74 (m, 2H), 7.48-7.52 (m, 2H), 7.37-7.42 (m, 1H), 3.71-3.75 (m, 1H), 3.33-3.45 (m, 2H), 3.28-3.32 (m, 1H), 3.09-3.18 (m, 1H), 2.16-2.20 (m, 1H), 1.81-1.90 (m, 2H), 1.70-1.75 (m, 1H).

EXAMPLE 2

2-(6-Phenyl-3H-imidazo[4,5-b]pyridin-2-yl)morpholine-4-carbonitrile

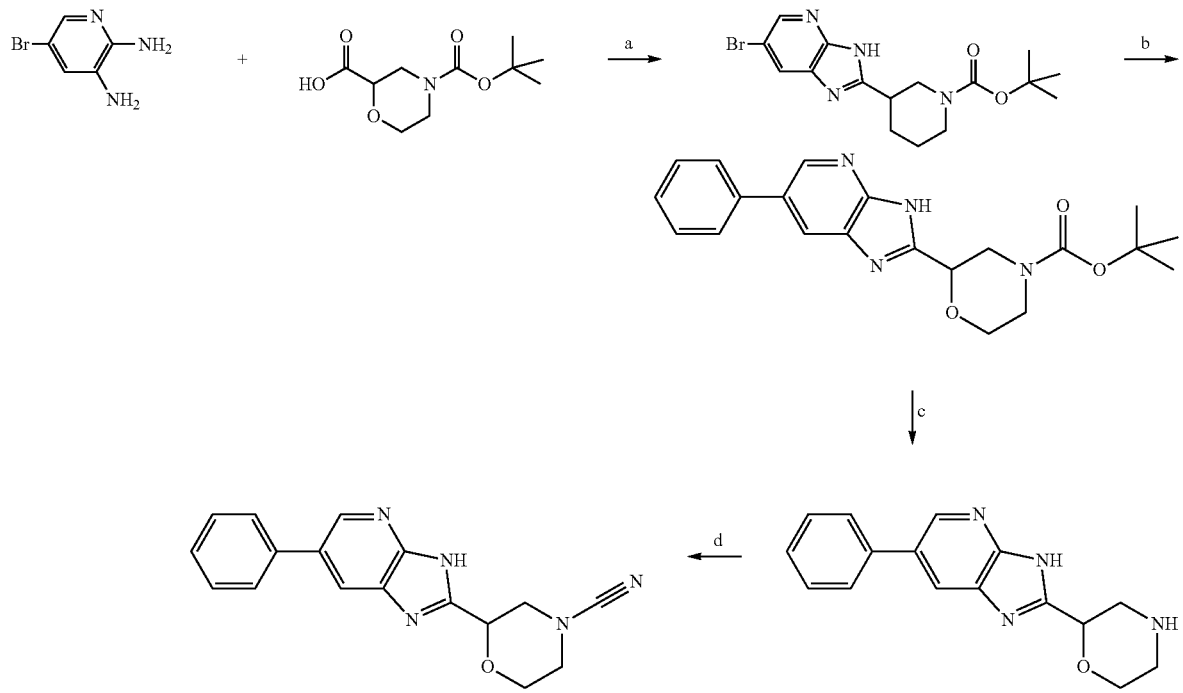

Step a.

To a solution of 5-bromopyridine-2,3-diamine (CAS Number 38875-53-5; 0.100 g, 0.539 mmol) in 1,4-dioxane (5 ml) were added 4-(tert-butoxycarbonyl)morpholine-2-carboxylic acid (CAS Number 189321-66-2; 0.120 g, 0.539 mmol) and DIPEA (0.3 ml, 1.595 mmol) at rt. T3P (50% in EtOAc; 0.676 g, 1.063 mmol) was added and the reaction mixture was heated at 120° C. for 16 h. The resulting mixture was cooled to rt and combined with three other batches prepared on the same scale by an identical method. The mixture was poured into water (150 ml) and extracted with EtOAc (2×100 ml). The combined organic layer was dried over $Na_2SO_4$, filtered and concentrated under reduced pressure. The resulting residue was purified by flash column chromatography (2% MeOH in DCM) yielding tert-butyl 2-(6-bromo-3H-imidazo[4,5-b]pyridin-2-yl)morpholine-4-carboxylate (0.654 g, 1.707 mmol). LCMS: Method C, 2.038 min, MS: ES+ 383.3, 385.

Step b.

To a solution of tert-butyl 2-(6-bromo-3H-imidazo[4,5-b]pyridin-2-yl)morpholine-4-carboxylate (0.350 g, 0.913 mmol) in DMF:water (1:1, 8 ml) were added $K_3PO_4$ (0.582 g, 2.748 mmol) and phenylboronic acid (0.168 g, 1.374 mmol) at rt. The reaction mixture was degassed for 10 min before addition of $PdCl_2(dppf)$ (0.067 g, 0.091 mmol). The reaction mixture was heated at 120° C. for 16 h then cooled to rt and filtered. The filtrate was evaporated under reduced pressure, with heating at 60° C. The obtained residue was dissolved in 10% MeOH in DCM (3×20 ml) and filtered. The combined filtrate was dried over $Na_2SO_4$, filtered and concentrated under reduced pressure to yielding tert-butyl 2-(6-phenyl-3H-imidazo[4,5-b]pyridin-2-yl)morpholine-4-carboxylate (0.965 g, quantitative). This material was used for next step without further purification. LCMS: Method C, 2.039 min, MS: ES+ 381.41.

Steps c, d.

The title compound was synthesised from the intermediate above using a procedure similar to that described for Example 1, steps c, d. LCMS: Method B, 3.364 min, MS: ES+ 306.32; $^1$H NMR (400 MHz, DMSO-d6) δ ppm: 12.98-13.34 (m, 1H), 8.63-8.69 (m, 1H), 8.05-8.29 (m, 1H), 7.73-7.74 (m, 2H), 7.49-7.52 (m, 2H), 7.38-7.42 (m, 1H), 4.99-5.09 (m, 1H), 3.99-4.01 (m, 1H), 3.76-3.88 (m, 2H), 3.51-3.62 (m, 1H), 3.40-3.42 (m, 2H).

EXAMPLE 3

3-(4-(3-Cyanophenyl)-1H-benzo[d]imidazol-2-yl)piperidine-1-carbonitrile

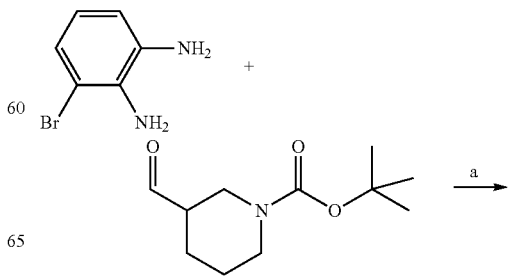

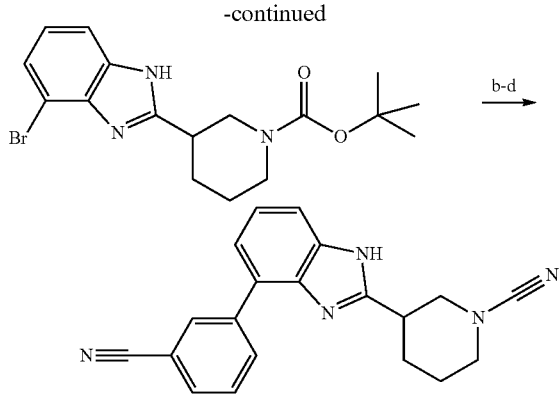

Step a.

To a stirred solution of tert-butyl 3-formylpiperidine-1-carboxylate (CAS Number 118156-93-7; 0.300 g, 1.407 mmol) and 3-bromobenzene-1,2-diamine (CAS Number 1575-36-6; 0.264 g, 1.407 mmol) in dry DMF (5.0 ml) was added sodium metabisulphite (0.267 g, 1.407 mmol) at rt. The reaction mixture was heated at 125° C. for 1.5 h. The resulting mixture was cooled to rt and poured into water (50 ml) and extracted with EtOAc (2×50 ml). The combined organic phase was dried over $Na_2SO_4$, filtered and concentrated under reduced pressure. The residue was purified by flash column chromatography (2% MeOH in DCM) yielding tert-butyl 3-(4-bromo-1H-benzo[d]imidazol-2-yl)-piperidine-1-carboxylate (0.325 g, 0.854 mmol). LCMS: Method C, 2.266 min, MS: ES+ 380.00, 382.00.

Steps b-d.

The title compound was synthesised from the intermediate above using a procedure similar to that described for Example 2, steps b-d. LCMS: Method B, 3.539 min, MS: ES+ 328.5; $^1$H NMR (400 MHz, DMSO-d6, drop of TFA) δ ppm: 8.23 (s, 1H), 8.09 (d, J=8.0 Hz, 1H), 8.00 (d, J=8.0 Hz, 1H), 7.79-7.85 (m, 2H), 7.59-7.65 (m, 2H), 3.78-3.81 (m, 1H), 3.37-3.55 (m, 3H), 3.09-3.16 (m, 1H), 2.21-2.23 (m, 1H), 1.84-1.99 (m, 2H), 1.70-1.73 (m, 1H).

EXAMPLE 4

2-(4-Phenyl-1H-benzo[d]imidazol-2-yl)morpholine-4-carbonitrile

Step a.

To a stirred solution of 3-bromo-2-nitroaniline (0.500 g, 2.303 mmol) and 4-(tert-butoxycarbonyl)morpholine-2-carboxylic acid (CAS Number 189321-66-2; 0.692 g, 2.995 mmol) in DCM (5 ml) was added pyridine (0.911 g, 11.519 mmol) followed by $POCl_3$ (1.06 g, 6.911 mmol) dropwise at 0° C. The resulting reaction mixture was slowly warmed to rt and stirred for 45 min then quenched with sat. $NaHCO_3$ solution (30 ml) and extracted with DCM (3×50 ml). The combined organic layer was washed with brine solution (50 ml), dried over $Na_2SO_4$, filtered and concentrated under reduced pressure yielding tert-butyl 2-((3-bromo-2-nitrophenyl)carbamoyl)-morpholine-4-carboxylate (0.910 g, 2.115 mmol). This material was used for next step without any further purification. LCMS: Method C, 2.275 min, MS: ES+ 430.60, 432.60.

Step b.

To a stirred solution of tert-butyl 2-((3-bromo-2-nitrophenyl)carbamoyl)-morpholine-4-carboxylate (0.900 g, 2.091 mmol) in THF: water (1:1, 14 ml) was added iron powder (0.584 g, 10.46 mmol) followed by $NH_4Cl$ (0.559 g, 10.456 mmol) at rt. The resulting reaction mixture was heated at 60° C. for 18 h then cooled to rt, filtered through a celite bed and washed with EtOAc (100 ml). The filtrate was extracted with EtOAc (3×100 ml). The combined organic layer was washed with brine solution (50 ml), dried over $Na_2SO_4$, filtered and concentrated under reduced pressure. The resulting residue was washed with n-pentane and concentrated under reduced pressure yielding tert-butyl 2-((2-amino-3-bromophenyl)carbamoyl)morpholine-4-carboxylate (0.830 g, 2.075 mmol). This material was used for next step without any further purification. LCMS: Method C, 1.943 min, MS: ES+ 400.50, 402.50.

Step c.

A stirred solution of tert-butyl 2-((2-amino-3-bromophenyl)carbamoyl)morpholine-4-carboxylate (0.800 g, 1.998 mmol) in acetic acid (8 ml) was heated at 40° C. for 3 h. The resulting reaction mixture was concentrated under reduced pressure. The obtained residue was purified by flash column chromatography (25% EtOAc in hexane) yielding tert-butyl 2-(4-bromo-1H-benzo[d]imidazol-2-yl)-morpholine-4-carboxylate (0.650 g, 1.701 mmol). LCMS: Method C, 1.892 min, MS: ES+ 382.50, 384.40.

Steps d-f.

The title compound was synthesised from the intermediate above using a procedure similar to that described for

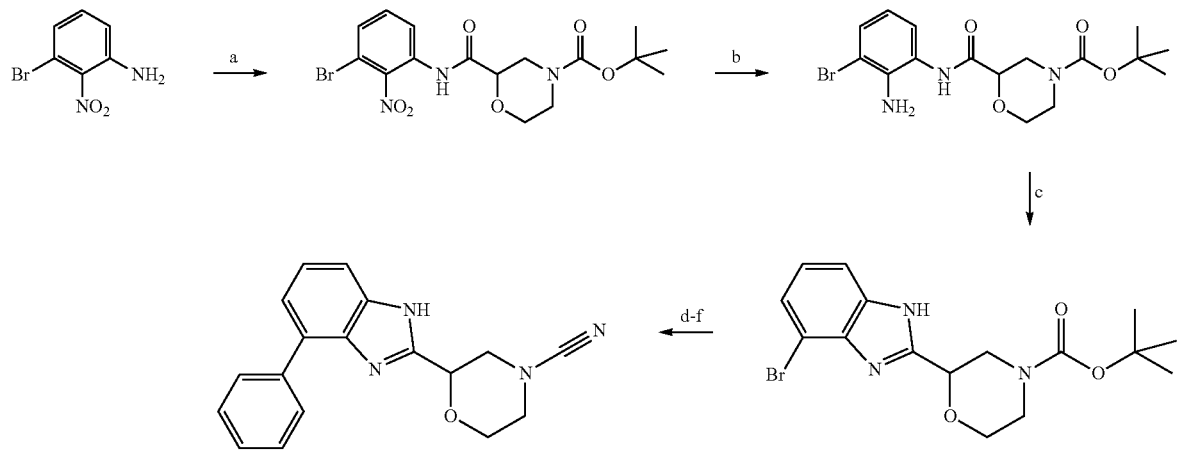

Example 2, steps b-d. LCMS: Method B, 3.722 min, MS: ES+ 305.5; ¹H NMR (400 MHz, DMSO-d6) δ ppm: 12.53-12.75 (m, 1H), 8.07 (d, J=7.6 Hz, 2H), 7.46-7.57 (m, 3H), 7.34-7.41 (m, 2H), 7.28-7.32 (m, 1H), 4.89-5.01 (m, 1H), 4.00-4.03 (m, 1H), 3.84-3.90 (m, 1H), 3.66-3.79 (m, 1H), 3.49-3.54 (m, 1H), 3.38-3.43 (m, 2H).

EXAMPLE 5

2-(4-(3-Cyanophenyl)-1H-benzo[d]imidazol-2-yl)morpholine-4-carbonitrile

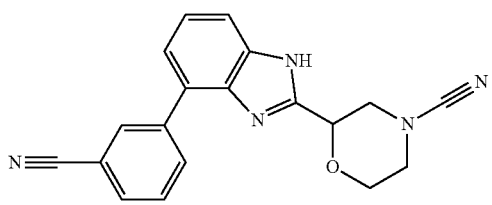 [SMILES: N#Cc1cccc(-c2cccc3[nH]c(C4CN(C#N)CCO4)nc23)c1]

Synthesised using a procedure similar to that described for Example 4. LCMS: Method A, 4.014 min, MS: ES+ 330.02; ¹H NMR (400 MHz, DMSO-d6) δ ppm: 12.85 (s, 1H), 8.52 (s, 1H), 8.46 (d, J=7.6 Hz, 1H), 7.81 (d, J=7.6 Hz, 1H), 7.68 (t, J=7.6 Hz, 1H), 7.50-7.52 (m, 2H), 7.31 (t, J=7.6 Hz, 1H), 4.98-5.00 (m, 1H), 3.97-3.99 (m, 1H), 3.82-3.87 (m, 1H), 3.72-3.76 (m, 1H), 3.46-3.52 (m, 1H), 3.32-3.40 (m, 2H).

Intermediate A [1,1'-Biphenyl]-3-carboximidamide

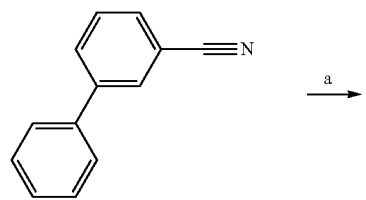

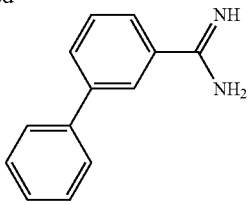

Step a.

To a solution of [1,1'-biphenyl]-3-carbonitrile (CAS Number 24973-50-0; 2.000 g, 11.17 mmol) in MeOH (15 ml) was added SOCl₂ (2.4 ml, 33.51 mmol) at 0° C. The reaction mixture was stirred at rt for 24 h. Ammonia gas was purged into the reaction mixture for 1 h and the resulting mixture was stirred at rt for 48 h. The obtained yellow precipitates were collected by filtration and washed with MeOH (20 ml). The crude product was purified by flash column chromatography (10% MeOH in DCM) yielding [1,1'-biphenyl]-3-carboximidamide (2.000 g, 10.20 mmol). LCMS: Method C, 1.479 min, MS: ES+ 197.23.

EXAMPLE 6

2-(3-([1,1'-Biphenyl]-3-yl)-H-1,2,4-triazol-5-yl)morpholine-4-carbonitrile

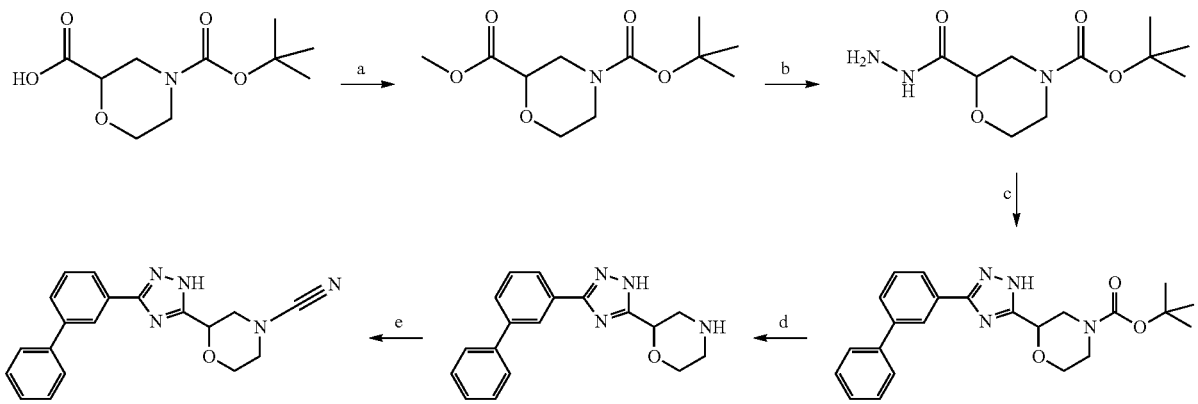 [SMILES: CC(C)(C)OC(=O)N1CCOC(C(=O)O)C1 ; COC(=O)C1CN(C(=O)OC(C)(C)C)CCO1 ; CC(C)(C)OC(=O)N1CCOC(C(=O)NN)C1 ; N#CN1CCOC(c2nc(-c3cccc(-c4ccccc4)c3)n[nH]2)C1 ; c1ccc(-c2cccc(-c3n[nH]c(C4CNCCO4)n3)c2)cc1 ; CC(C)(C)OC(=O)N1CCOC(c2nc(-c3cccc(-c4ccccc4)c3)n[nH]2)C1]

Step a.

To a solution of 4-(tert-butoxycarbonyl)morpholine-2-carboxylic acid (CAS Number 189321-66-2; 0.500 g, 2.164 mmol) in dry DMF (3 ml) was added K₂CO₃ (1.190 g, 8.66 mmol) and methyl iodide (0.922 g, 6.49 mmol) at rt. The reaction mixture was stirred at rt for 36 h then poured into 1M HCl (20 ml) and extracted with EtOAc (3×50 ml). The combined organic phase was washed with water (50 ml), dried over Na₂SO₄, filtered and concentrated under reduced pressure to yield 4-(tert-butyl) 2-methyl morpholine-2,4-dicarboxylate (0.624 g, quantitative). This material was used for next step without further purification. LCMS: Method C, 1.756 min, MS: ES+ 246.48.

Step b.

To a solution of 4-(tert-butyl) 2-methyl morpholine-2,4-dicarboxylate (0.624 g, 2.54 mmol) in MeOH (1 ml) was added hydrazine monohydrate (3.72 ml) at rt. The reaction mixture was heated at 50° C. for 5 h. The resulting mixture was cooled to rt and poured into water (50 ml) then extracted with EtOAc (3×25 ml). The combined organic phase was washed with water (50 ml), dried over Na₂SO₄, filtered and concentrated under reduced pressure to yield tert-butyl 2-(hydrazinecarbonyl)morpholine-4-carboxylate (0.539 g, 2.200 mmol). LCMS: Method C, 1.426 min, MS: ES+ 246.48.

Step c.

To a solution of tert-butyl 2-(hydrazinecarbonyl)morpholine-4-carboxylate (0.399 g, 1.628 mmol) and [1,1'-biphenyl]-3-carboximidamide (Intermediate A; 0.351 g, 1.790 mmol) in EtOH (6 ml) was added NaOEt (0.332 g, 4.885 mmol) at rt. The reaction mixture was heated at 80° C. for 40 h. The resulting mixture was cooled to rt, poured into brine solution (100 ml) and extracted with EtOAc (3×50 ml). The combined organic phase was washed with water (50 ml), dried over Na$_2$SO$_4$, filtered and concentrated under reduced pressure. The resulting residue was purified by flash column chromatography (60% EtOAc in hexane) yielding tert-butyl 2-(3-([1,1'-biphenyl]-3-yl)-1H-1,2,4-triazol-5-yl)morpholine-4-carboxylate (0.225 g, 0.554 mmol). LCMS: Method C, 2.203 min, MS: ES+ 407.60.

Steps d, e.

The title compound was synthesised from the intermediate above using a procedure similar to that described for Example 1, steps c, d. LCMS: Method B, 3.934 min, MS: ES+ 332.43; $^1$H NMR (400 MHz, DMSO-d6) δ ppm: 14.33-14.40 (m, 1H), 8.25-8.29 (m, 1H), 7.97-8.0 (m, 1H), 7.81-7.83 (m, 1H), 7.70-7.77 (m, 2H), 7.62-7.66 (m, 1H), 7.49-7.59 (m, 2H), 7.41-7.45 (m, 1H), 4.73-4.98 (m, 1H), 3.91-4.04 (m, 1H), 3.73-3.87 (m, 2H), 3.58-3.60 (m, 1H), 3.35-3.50 (m, 2H).

Intermediate B Benzyl 3-carbamoylpiperidine-1-carboxylate

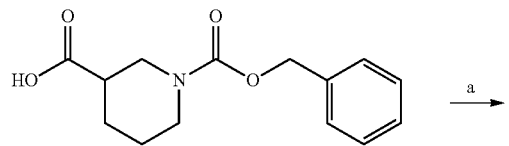

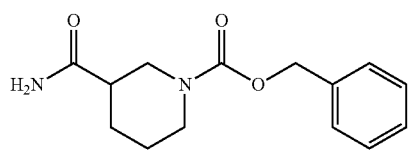

Step a.

To a stirred solution of 1-((benzyloxy)carbonyl)piperidine-3-carboxylic acid (CAS Number 78190-11-1; 3.000 g, 11.390 mmol) in MeCN (20 ml) was added CDI (2.210 g, 13.670 mmol) at 0° C. The reaction mixture was stirred at rt for 1 h. Ammonia solution (30% in water; 40 ml) was slowly added to the reaction mixture at rt and stirred for 16 h. The resulting mixture was diluted with water (50 ml), basified with saturated NaHCO$_3$ solution and extracted with EtOAc (3×50 ml). The combined organic phase was washed with aqueous citric acid solution (50 ml), dried over Na$_2$SO$_4$, filtered and concentrated on reduced pressure. The resulting residue was purified by flash column chromatography (4% MeOH in DCM) yielding benzyl 3-carbamoylpiperidine-1-carboxylate (2.700 g, 10.30 mmol). LCMS: Method C, 1.585 min, MS: ES+ 263.39.

EXAMPLE 7

3-(4-(2-Phenoxyphenyl)oxazol-2-yl)piperidine-1-carbonitrile

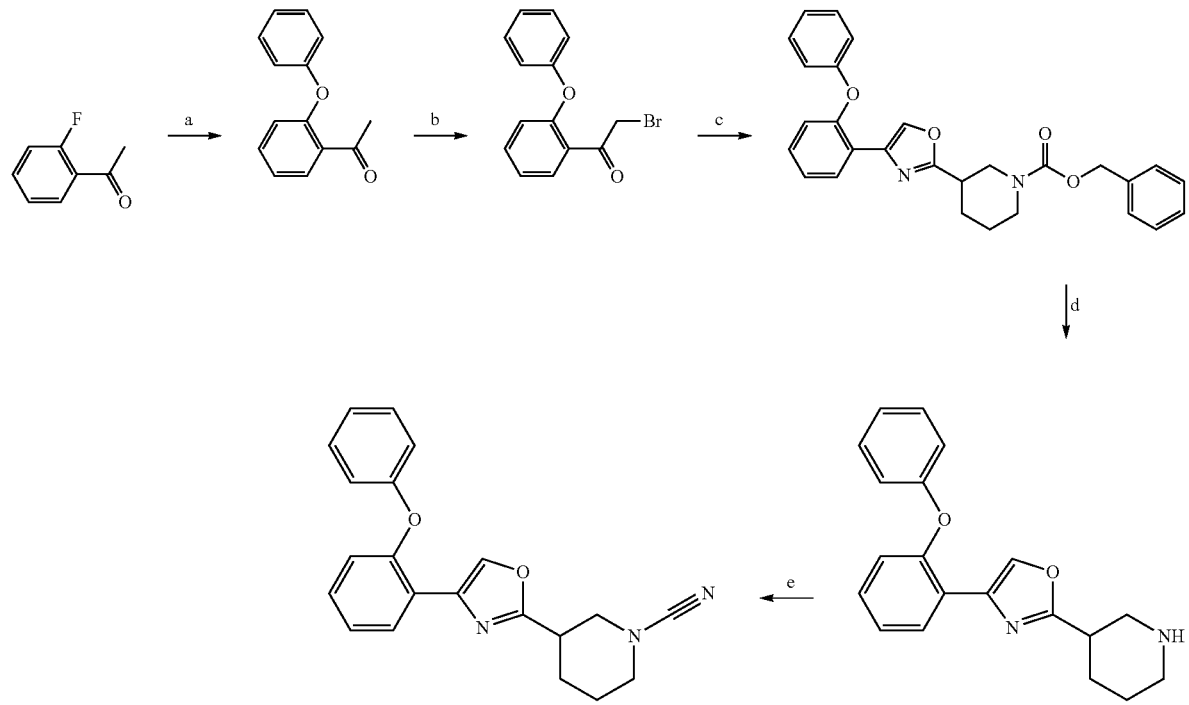

Step a.

To a solution of 1-(2-fluorophenyl)ethan-1-one (CAS Number 445-27-2; 0.500 g, 3.620 mmol) and phenol (0.374 g, 3.981 mmol) in DMA (5 ml) was added $K_2CO_3$ (0.450 g, 3.258 mmol) at rt. The reaction mixture was heated at 155° C. for 4 h. The resulting mixture was cooled to rt and combined with one other batch prepared on the same scale by an identical method. The reaction mixture was poured into water (50 ml) and extracted with EtOAc (3×50 ml). The combined organic layer was washed with brine solution (50 ml), dried over $Na_2SO_4$, filtered and concentrated under reduced pressure. The resulting residue was purified by flash column chromatography (1% EtOAc in hexane) yielding 1-(2-phenoxyphenyl)ethan-1-one (0.850 g, 4.01 mmol). LCMS: Method C, 2.275 min, MS: ES+ 213.33; $^1$H NMR (400 MHz, CDCl$_3$) δ ppm: 7.87 (dd, J=7.6, 1.6 Hz, 1H), 7.37-7.47 (m, 3H), 7.15-7.21 (m, 2H), 7.03-7.05 (m, 2H), 6.92-6.94 (m, 1H), 2.66 (s, 3H).

Step b.

To a stirred solution of 1-(2-phenoxyphenyl)ethan-1-one (0.750 g, 3.53 mmol) in THF (10 ml) was added phenyltrimethylammonium tribromide (1.460 g, 3.887 mmol) portion-wise at 0° C. The reaction mixture was stirred at rt for 16 h. The resulting mixture was diluted with water (30 ml) and extracted with EtOAc (3×50 ml). The combined organic phase was washed with brine solution (30 ml), dried over $Na_2SO_4$, filtered and concentrated under reduced pressure. The residue was purified by flash column chromatography (3% EtOAc in hexane) to afford 2-bromo-1-(2-phenoxyphenyl)ethan-1-one (0.900 g, 3.10 mmol). LCMS: Method C, 2.417 min, MS: ES+ 291.00, 293.00; $^1$H NMR (400 MHz, CDCl$_3$) δ ppm: 7.93-7.98 (m, 1H), 7.42-7.49 (m, 3H), 7.16-7.24 (m, 2H), 7.10-7.24 (m, 2H), 6.83-6.89 (m, 1H), 4.67 (s, 2H).

Step c.

To a stirred solution of 2-bromo-1-(2-phenoxyphenyl)ethan-1-one (0.500 g, 1.72 mmol) and benzyl 3-carbamoylpiperidine-1-carboxylate (Intermediate B, 0.540 g, 2.06 mmol) in EtOAc (10 ml) was added silver triflate (0.515 g, 2.060 mmol) portion-wise at rt. The reaction mixture was heated at 80° C. for 24 h. The resulting mixture was cooled to rt, diluted with water (50 ml) and extracted with EtOAc (3×50 ml). The combined organic phase was washed with brine solution (50 ml), dried over anhydrous $Na_2SO_4$, filtered and concentrated under reduced pressure. The residue was purified by flash column chromatography (5% EtOAc in hexane) yielding benzyl 3-(4-(2-phenoxyphenyl)oxazol-2-yl)-piperidine-1-carboxylate (0.405 g, 0.890 mmol). LCMS: Method C, 2.849 min, MS: ES+455.75.

Step d.

To a stirred solution of benzyl 3-(4-(2-phenoxyphenyl)oxazol-2-yl)piperidine-1-carboxylate (0.380 g, 0.830 mmol) in EtOH (10 ml) was added 10% Pd/C (50% moisture; 0.076 g) at rt. The reaction mixture was purged with $H_2$ gas at rt for 5 h. The resulting reaction mixture was carefully filtered through celite hyflow, washing with EtOAc (100 ml). The combined filtrate was acidified using 4M HCl in 1,4-dioxane (1 ml). The resulting organic phase was concentrated under reduced pressure yielding 4-(2-phenoxyphenyl)-2-(piperidin-3-yl)oxazole HCl salt (0.220 g, 0.617 mmol). This material was used for the next step without further purification. LCMS: Method C, 1.725 min, MS: ES+ 321.48.

Step e.

To a solution of 4-(2-phenoxyphenyl)-2-(piperidin-3-yl) oxazole HCl salt (0.210 g, 0.588 mmol) in THF:DMF (5:1, 10 ml) was added $K_2CO_3$ (0.406 g, 2.940 mmol) at 0° C. The reaction mixture was stirred at 0° C. for 5 min before the addition of cyanogen bromide (0.074 g, 0.708 mmol). The reaction mixture was warmed to rt, stirred for 2 h and then poured into water (50 ml) and extracted with EtOAc (3×50 ml). The combined organic phase was washed with brine (30 ml), dried over $Na_2SO_4$, filtered and concentrated under reduced pressure. The resulting residue was purified by flash column chromatography (20% EtOAc in hexane) to afford the title compound (0.120 g, 0.347 mmol). LCMS: Method A, 5.469 min, MS: ES+ 346.00; $^1$H NMR (400 MHz, DMSO-d6) δ ppm: 8.25 (s, 1H), 8.11 (dd, J=8.0, 2.0 Hz, 1H), 7.36-7.42 (m, 2H), 7.32-7.34 (m, 1H), 7.25-7.29 (m, 1H), 7.13-7.17 (m, 1H), 7.02-7.05 (m, 2H), 6.94-6.96 (m, 1H), 3.63-3.67 (m, 1H), 3.35-3.42 (m, 1H), 3.30-3.32 (m, 1H), 3.19-3.24 (m, 1H), 3.12-3.16 (m, 1H), 2.06-2.07 (m, 1H), 1.66-1.79 (m, 3H).

EXAMPLE 8

3-(4-([1,1'-Biphenyl]-3-yl)oxazol-2-yl)piperidine-1-carbonitrile

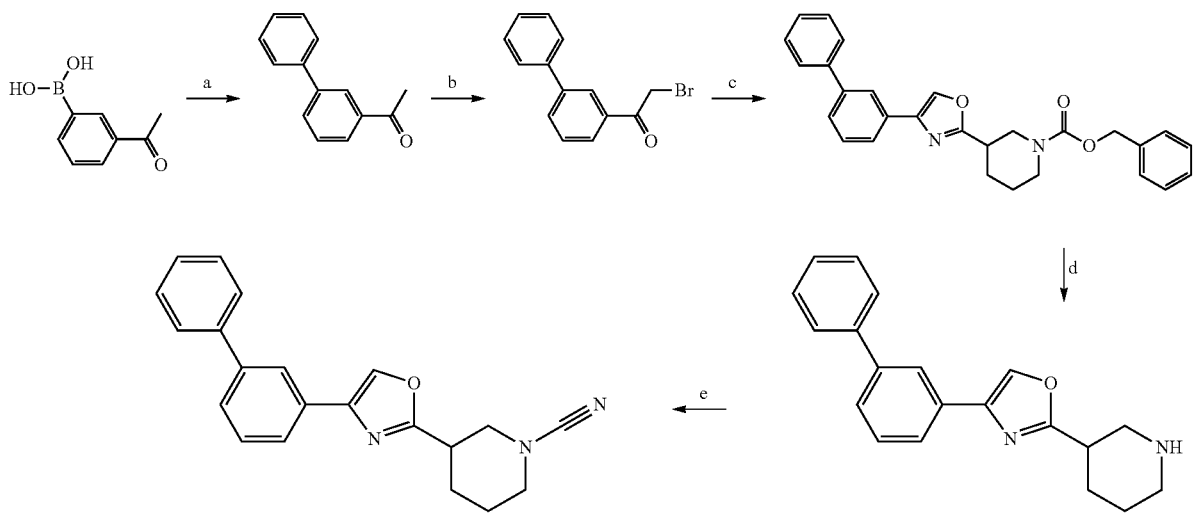

Step a.

To a solution of (3-acetylphenyl)boronic acid (CAS Number 204841-19-0; 1.253 g, 7.64 mmol) and bromobenzene (1.00 g, 6.37 mmol) in 1,4-dioxane:water (8:2, 10 ml) was added $Na_2CO_3$ (2.006 g, 19.1 mmol) at rt. The reaction mixture was degassed for 30 min before addition of $Pd(PPh_3)_4$ (0.367 g, 0.318 mmol). The reaction mixture was heated at 90° C. for 1.5 h. The resulting reaction mixture was cooled to rt, poured into water (50 ml) and extracted with EtOAc (4×30 ml). The combined organic layer was washed with brine solution (50 ml), dried over $Na_2SO_4$, filtered and concentrated under reduced pressure. The resulting residue was purified by flash column chromatography (9% EtOAc in hexane) to afford 1-([1,1'-biphenyl]-3-yl)ethan-1-one (0.850 g, 4.336 mmol). LCMS: Method C, 2.599 min, MS: ES+ 197.20; $^1$H NMR (400 MHz, CDCl3) δ ppm: 8.21 (s, 1H), 7.95-7.97 (m, 1H), 7.80-7.83 (m, 1H), 7.64-7.66 (m, 2H), 7.55-7.58 (m, 1H), 7.48-7.51 (m, 2H), 7.39-7.43 (m, 1H), 2.68 (s, 3H).

Step b.

To a stirred solution of 1-([1,1'-biphenyl]-3-yl)ethan-1-one (0.790 g, 4.030 mmol) in THF (5 ml) was added phenyltrimethylammonium tribromide (1.662 g, 4.433 mmol) at rt. The reaction mixture was stirred at rt for 1 h. The resulting mixture was diluted with water (25 ml) and extracted with EtOAc (3×30 ml). The combined organic phase was dried over $Na_2SO_4$, filtered and concentrated under reduced pressure to afford 1-([1,1'-biphenyl]-3-yl)-2-bromoethan-1-one (1.1 g, quantitative). This material was used for next step without further purification. MS: ES+ 275.0, 277.0.

EtOAc in hexane) yielding benzyl 3-(4-([1,1'-biphenyl]-3-yl)oxazol-2-yl)piperidine-1-carboxylate (0.160 g, 0.365 mmol). LCMS: Method C, 3.312 min, MS: ES+ 439.20.

Step d.

To a stirred solution of benzyl 3-(4-([1,1'-biphenyl]-3-yl)oxazol-2-yl)piperidine-1-carboxylate (0.180 g, 0.410 mmol) in EtOH (10 ml) was added a catalytic amount of concentrated HCl followed by 10% Pd/C (50% moisture; 0.036 g) at rt. The reaction mixture was stirred under 100 psi $H_2$ gas pressure at rt for 16 h. The resulting reaction mixture was carefully filtered through celite hyflow and the filtrate was concentrated under reduced pressure yielding 4-([1,1'-biphenyl]-3-yl)-2-(piperidin-3-yl)oxazole (0.200 g, quantitative). This material was used for the next step without further purification. LCMS: Method C, 2.085 min, MS: ES+ 305.20.

Step e.

The title compound was synthesised from the intermediate above using a procedure similar to that described for Example 1, step d. LCMS: Method B, 4.594 min, MS: ES+ 330.68; $^1$H NMR (400 MHz, DMSO-d6) δ ppm: 8.69 (s, 1H), 8.05 (s, 1H), 7.77 (d, J=7.2 Hz, 1H), 7.70-7.78 (m, 2H), 7.62 (d, J=7.6 Hz, 1H), 7.48-7.54 (m, 3H), 7.38-7.42 (m, 1H), 3.65-3.69 (m, 1H), 3.38-3.44 (m, 1H), 3.30-3.33 (m, 1H), 3.21-3.26 (m, 1H), 3.12-3.17 (m, 1H), 2.05-2.10 (m, 1H), 1.65-1.82 (m, 3H).

EXAMPLE 9

(R)-3-(5-([1,1'-biphenyl]-3-yl)-1,3,4-oxadiazol-2-yl)-3-fluoropiperidine-1-carbonitrile

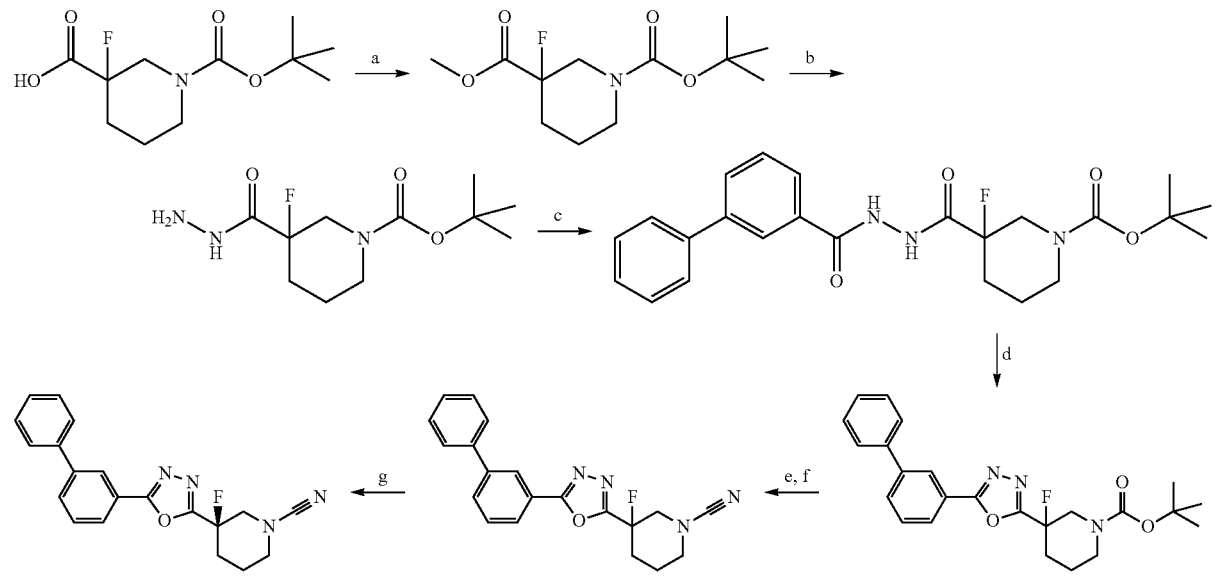

Step c.

A mixture of 1-([1,1'-biphenyl]-3-yl)-2-bromoethan-1-one (0.650 g, 2.37 mmol) and benzyl 3-carbamoylpiperidine-1-carboxylate (Intermediate B, 0.621 g, 2.37 mmol) was heated at 150° C. for 5 h. The resulting mixture was cooled to rt and diluted with EtOAc (20 ml), diluted with saturated $NaHCO_3$ solution (20 ml) and extracted with EtOAc (3×20 ml). The combined organic phase was washed with water (20 ml), dried over anhydrous $Na_2SO_4$, filtered and concentrated under reduced pressure. The resulting residue was purified by flash column chromatography (10%

Step a.

To a stirred solution of 1-(tert-butoxycarbonyl)-3-fluoropiperidine-3-carboxylic acid (0.400 g, 1.62 mmol) in acetone (4 ml) was added $K_2CO_3$ (0.670 g, 4.86 mmol) followed by the addition of methyl iodide (0.689 g, 4.86 mmol) at 0° C. under nitrogen and the resulting mixture was stirred at rt for 12 h. The resulting reaction mixture was concentrated under reduced pressure and crude was diluted with water (50 ml) and extracted with EtOAc (3×50 ml). Combined organic extracts were dried over anhydrous $Na_2SO_4$, filtered and concentrated under reduced pressure to yield 1-(tert-butyl) 3-methyl 3-fluoropiperidine-1,3-dicarboxylate (0.400 g, 1.53 mmol; Crude). LCMS: Method C, 1.933 min, MS: ES+ 262.58.

Step b.

To a stirred solution of 1-(tert-butyl) 3-methyl 3-fluoropiperidine-1,3-dicarboxylate (0.800 g, 3.07 mmol; crude) in MeOH (10 ml) was added hydrazine hydrate (0.383 g, 7.66 mmol) drop-wise at 0° C. and the resulting mixture was stirred at rt for 16 h. Reaction mixture was concentrated under reduced pressure, crude was diluted with water (50 ml) and extracted with DCM (2×150 ml). Combined organic extracts were dried over anhydrous $Na_2SO_4$, filtered and concentrated under reduced pressure to yield tert-butyl 3-fluoro-3-(hydrazinecarbonyl)piperidine-1-carboxylate (0.825 g, 3.16 mmol; Crude). Crude material was carried to next step without any further purification. LCMS: Method C, 1.503 min, MS: ES+ 262.43.

Step c.

To a stirred solution of [1,1'-biphenyl]-3-carboxylic acid (0.285 g, 1.44 mmol; crude) in THF (3 ml) was added DIPEA (0.70 ml, 3.85 mmol) followed by the addition of HATU (0.730 g, 1.92 mmol) at 0° C. After 15 min of stirring at the same temperature, was added a solution of tert-butyl 3-fluoro-3-(hydrazinecarbonyl)piperidine-1-carboxylate (0.25 g, 0.96 mmol) in THF (2 ml) at 0° C. and stirring was continued at rt for 3 h. The resulting reaction mixture was diluted with water (50 ml) and was extracted with EtOAc (3×50 ml). Combined organic extracts were washed with an aqueous solution of saturated sodium bicarbonate (4×50 ml), dried over anhydrous $Na_2SO_4$, filtered and concentrated under reduced pressure to yield tert-butyl 3-(2-([1,1'-biphenyl]-3-carbonyl)hydrazine-1-carbonyl)-3-fluoropiperidine-1-carboxylate (0.62 g, 1.41 mmol; Crude). Crude material was carried to next step without any further purification. LCMS: Method C, 2.285 min, MS: ES-440.48

Step d.

To a stirred solution of tert-butyl 3-(2-([1,1'-biphenyl]-3-carbonyl)hydrazine-1-carbonyl)-3-fluoropiperidine-1-carboxylate (0.600 g, 1.36 mmol) in DCM (5 ml) was added triethylamine (0.413 g, 0.57 ml, 4.09 mmol) followed by addition of tosyl chloride (0.388 g, 2.05 mmol) at 0° C. Resulting mixture was stirred at rt for 2 h. The resulting reaction mixture was diluted with water (50 ml) and was extracted with DCM (2×50 ml). Combined organic extracts were dried over anhydrous $Na_2SO_4$, filtered and concentrated under reduced pressure to give a crude mass, which was purified by column chromatography (silica, 25% EtOAc in hexane) to yield tert-butyl 3-(5-([1,1'-biphenyl]-3-yl)-1,3,4-oxadiazol-2-yl)-3-fluoropiperidine-1-carboxylate (0.420 g, 0.99 mmol). LCMS: Method C, 2.609 min, MS: ES+ 424.48.

Steps e, f.

The title compound was synthesised from the intermediate above using a procedure similar to that described for Example 1, steps c, d.

Step g.

Separation of the racemate by chiral SFC provided the title compound as the second eluting isomer under the following conditions: Waters SFC 200 and UV detector, using a Chiralpak IC 250×21 mm, 5 µM, column flow was 75.0 ml/min, mobile phase: (A) liquid carbon dioxide and (B) IPA, isocratic gradient of 25% B over 11 minutes. LCMS: Method A, 4.402 min, MS: ES+ 349.1; $^1$H NMR (400 MHz, DMSO-d6) δ ppm: 8.31 (s, 1H), 8.09 (d, J=7.6 Hz, 1H), 7.98 (d, J=7.6 Hz, 1H), 7.78 (d, J=7.6 Hz, 2H), 7.73 (t, J=7.6 Hz, 1H), 7.53 (t, J=7.6 Hz, 2H), 7.45 (t, J=7.6 Hz, 1H), 4.04-3.99 (m, 1H), 3.85 (dd, J=29.6 Hz, 14.4 Hz, 1H), 3.46-3.43 (m, 1H), 3.27-3.22 (m, 1H), 2.38-2.25 (m, 1H), 2.01-1.92 (m, 1H), 1.79-1.76 (m, 1H).

EXAMPLE 10

3-(5-([1,1'-biphenyl]-4-yl)-1,3,4-oxadiazol-2-yl)-3-fluoropiperidine-1-carbonitrile

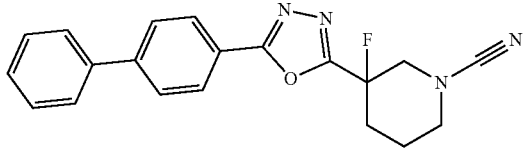 [SMILES: N#CN1CCCC(F)(c2nnc(-c3ccc(-c4ccccc4)cc3)o2)C1]

The title compound was synthesised using a procedure similar to that described for Example 9, steps a-f. LCMS: Method A, 4.510 min, MS: ES+ 349.1; $^1$H NMR (400 MHz, DMSO-d6) δ ppm: 8.17 (d, J=8.0 Hz, 2H), 7.95 (d, J=8.4 Hz, 2H), 7.79 (d, J=7.6 Hz, 2H), 7.53 (t, J=8.0 Hz, 2H), 7.46 (t, J=7.2 Hz, 1H), 3.98-3.94 (m, 1H), 3.85 (dd, J=29.2 Hz, 14.0 Hz, 1H), 3.46-3.43 (m, 1H), 3.28-3.25 (m, 1H), 2.38-2.25 (m, 1H), 1.99-1.95 (m, 1H), 1.79-1.76 (m, 1H).

Intermediate (R)-1-(Tert-butoxycarbonyl)-3-fluoropiperidine-3-carboxylic Acid

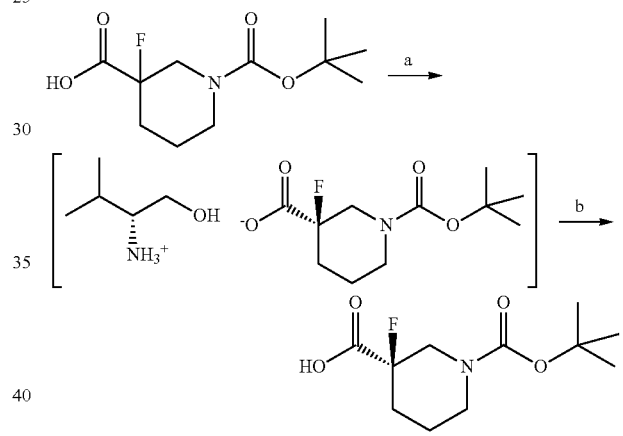

Step a.

To a solution of 1-(tert-butoxycarbonyl)-3-fluoropiperidine-3-carboxylic acid (CAS Number 934342-39-9; 285.3 g, 1.15 mol) in MeCN (1.4 L containing 1.5% of water) was added a solution of D-valinol (107.1 g, 1.04 mol) in MeCN (1.4 L containing 1.5% of water). A solid precipitated and the mixture was stirred at reflux until complete dissolution of the solids and then stirring continued at rt for 16 h. The solids obtained were filtered off and washed with MeCN (500 ml). The absolute stereochemistry of a sample of the crystalline material was determined as the (R)-2-amino-3-methylbutan-1-ol (D-valinol) salt of (R)-1-(tert-butoxycarbonyl)-3-fluoropiperidine-3-carboxylic acid by single crystal X-ray diffraction.

Step b.

The collected solids were suspended in DCM and treated with a 0.5 M solution of hydrochloric acid. The organic phase was washed two times with a 0.5 M solution of hydrochloric acid, dried over magnesium sulfate, filtered and concentrated under vacuum to give 110 g of the title product (37% yield) in 98% ee (the enantiomeric excess of this material was checked by derivatization of a sample with aniline). $^1$H NMR (300 MHz, CD$_3$OD) δ ppm: 4.14 (bs, 1H), 3.98-4.02 (d, 1H), 3.30-3.50 (m, 1H), 2.91 (bs, 1H), 1.95-2.08 (m, 2H), 1.59-1.80 (m, 2H), 1.45 (s, 9H).

The opposite enantiomer may be prepared using L-valinol.

EXAMPLE 11

(R)-4-(5-(1-cyano-3-fluoropiperidin-3-yl)-1,3,4-oxadiazol-2-yl)-[2,4'-bipyridine]-2'-carbonitrile

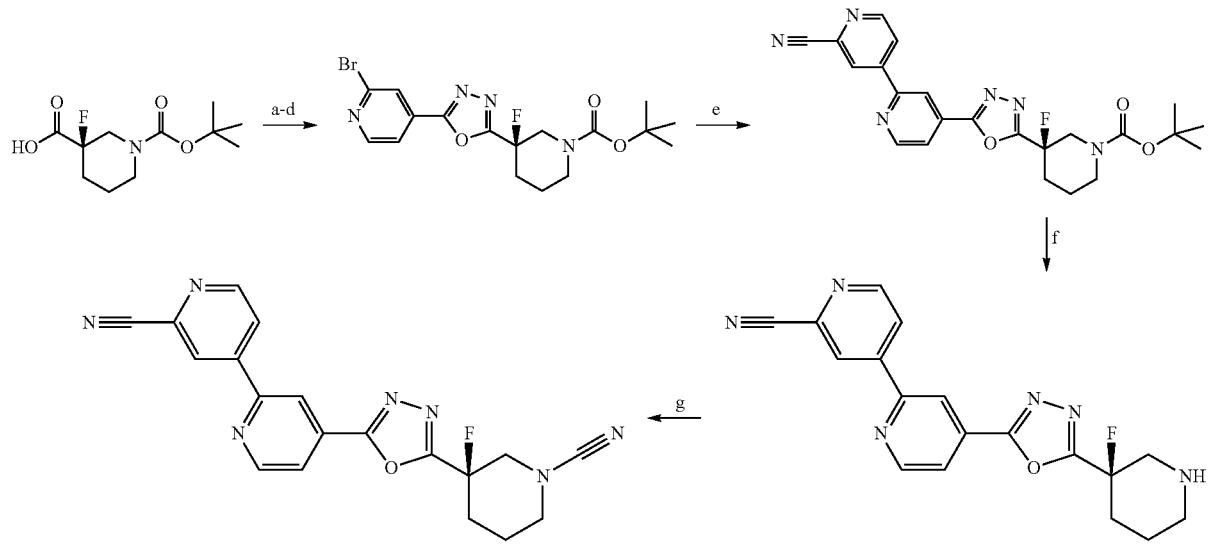

Steps a-d.

The first 4 steps followed a procedure similar to that described for Example 9, steps a-d, using (R)-1-(tert-butoxycarbonyl)-3-fluoropiperidine-3-carboxylic acid in step a and methyl 2-bromoisonicotinate (CAS Number 26156-48-9) in step c.

Step e.

To a stirred solution of tert-butyl (R)-3-(5-(2-bromopyridin-4-yl)-1,3,4-oxadiazol-2-yl)-3-fluoropiperidine-1-carboxylate (0.160 g, 0.38 mmol) and 4-(4,4,5,5-tetramethyl-1,3,2-dioxaborolan-2-yl)-picolinonitrile (0.129 g, 0.56 mmol) in DMF-water (5:1; 6 ml) was added NaHCO$_3$ (0.094 g, 1.13 mmol) at rt. The reaction mixture was degassed with nitrogen for 15 min and PdCl$_2$(dppf) (0.027, 0.04 mmol) was added into the reaction mixture. The resulting reaction mixture was heated at 90° C. for 1 h. After cooling to rt, the reaction mixture was poured into ice-water (100 ml) and extracted with EtOAc (2×100 ml). The combined organic extracts were dried over anhydrous Na$_2$SO$_4$, filtered and concentrated under reduced pressure. The resulting residue was purified by flash column chromatography (40% EtOAc in hexane) to give tert-butyl (R)-3-(5-(2'-cyano-[2,4'-bipyridin]-4-yl)-1,3,4-oxadiazol-2-yl)-3-fluoropiperidine-1-carboxylate (0.160 g, 0.36 mmol). LCMS: Method C, 1.763 min, MS: ES+ 451.66.

Steps f, g.

The title compound was synthesised from the intermediate above using a procedure similar to that described for Example 1, steps c, d. LCMS: Method A, 3.510 min, MS: ES+ 376; $^1$H NMR (400 MHz, DMSO-d6) δ ppm: 9.07 (d, J=5.2 Hz, 1H), 8.95 (d, J=5.2 Hz, 1H), 8.88 (s, 1H), 8.82 (s, 1H), 8.55 (dd, J=4.8 Hz, 1.6 Hz, 1H), 8.21 (dd, J=5.2 Hz, 1.2 Hz, 1H), 4.08-4.02 (m, 1H), 3.87 (dd, J=29.6 Hz, 14.0 Hz, 1H), 3.49-3.46 (m, 1H), 3.30-3.24 (m, 1H), 2.50-2.26 (m, 2H), 2.04-1.95 (m, 1H), 1.82-1.79 (m, 1H).

EXAMPLE 12

(R)-4-(5-(1-cyano-3-fluoropiperidin-3-yl)-1,3,4-oxadiazol-2-yl)picolinonitrile

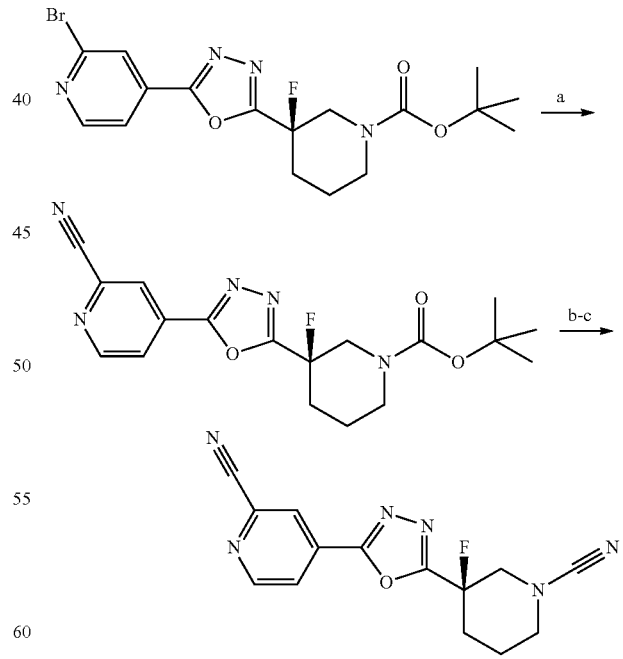

Step a.

To a stirred solution of tert-butyl (R)-3-(5-(2-bromopyridin-4-yl)-1,3,4-oxadiazol-2-yl)-3-fluoropiperidine-1-carboxylate (synthesis described in example 11, steps a-d; 0.200 g, 0.47 mmol) in DMF (5 ml) was added Zn(CN)$_2$ (0.110 g, 0.94 mmol) at rt. The reaction mixture was degassed with nitrogen for 10 min and Pd(PPh₃)₄ (0.054 g, 0.05 mmol) was added into the reaction mass and the resulting reaction mixture was heated at 90° C. for 4 h. The reaction mixture was cooled to rt, poured into ice cold water (100 ml) and extracted with EtOAc (2×100 ml). The combined organic phase was dried over anhydrous Na₂SO₄, filtered and concentrated under reduced pressure. The resulting crude residue was purified by flash column chromatography (20% EtOAc in n-hexane) to give tert-butyl (R)-3-(5-(2-cyanopyridin-4-yl)-1,3,4-oxadiazol-2-yl)-3-fluoropiperidine-1-carboxylate (0.110 g, 0.29 mmol). LCMS: Method C, 1.729 min, MS: ES (MH-56) 318.3.

Steps b, c.

The title compound was synthesised from the intermediate above using a procedure similar to that described for Example 1, steps c, d. LCMS: Method A, 3.075 min, MS: ES+ 316.1 (MH+18); ¹H NMR (400 MHz, DMSO-d6) δ ppm: 9.03 (d, J=4.8 Hz, 1H), 8.73 (s, 1H), 8.37 (dd, J=5.2 Hz, 1.6 Hz, 1H), 4.04-3.98 (m, 1H), 3.83 (dd, J=30.0 Hz, 14.4 Hz, 1H), 3.48-3.44 (m, 1H), 3.28-3.23 (m, 1H), 2.50-2.27 (m, 2H), 1.99-1.93 (m, 1H), 1.80-1.77 (m, 1H).

EXAMPLE 13

(R)-2'-(5-(1-cyano-3-fluoropiperidin-3-yl)-1,3,4-oxadiazol-2-yl)-[4,4'-bipyridine]-2-carbonitrile

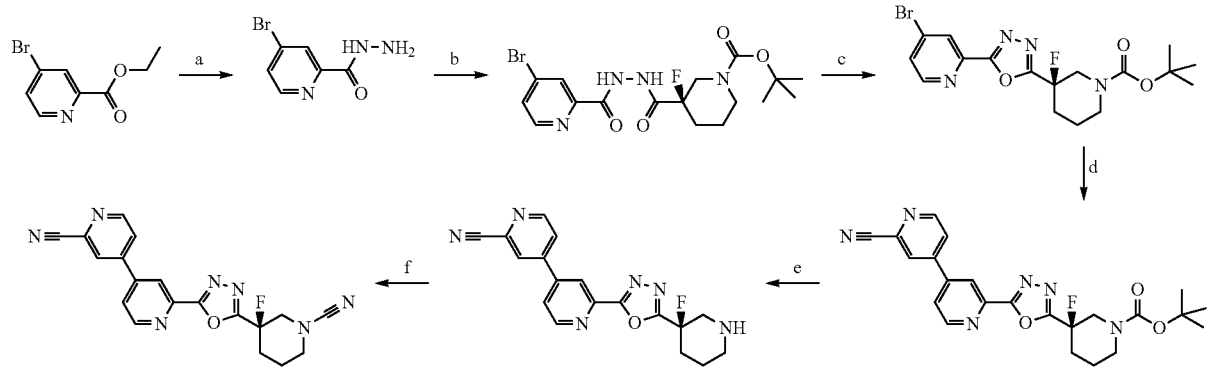

Step a.

To a stirred solution of ethyl 4-bromopicolinate (CAS Number 62150-47-4; 0.700 g, 3.04 mmol) in ethanol (7 ml) was added hydrazine hydrate (0.456 g, 9.12 mmol) dropwise at 0° C. The reaction temperature was raised from 0° C. to rt and stirred for an additional 30 min. Ethanol was removed under reduced pressure. To the crude reaction, was added water (50 ml) and the product was extracted in EtOAc (2×50 ml). Combined organic extracts were dried over anhydrous Na₂SO₄, filtered and concentrated under reduced pressure to give 4-bromopicolinohydrazide (0.620 g, 2.88 mmol, Crude). The crude solid was directly used for next step without purification. LCMS: Method C, 1.291 min, MS: ES+ 216.13.

Step b.

To a stirred solution of (R)-1-(tert-butoxycarbonyl)-3-fluoropiperidine-3-carboxylic acid (0.686 g, 2.78 mmol) in THF were added DIPEA (1.00 g, 7.75 mmol) and TBTU (1.300 g, 4.05 mmol) at 0° C. and stirred for 1 h at the same temperature. 4-Bromopicolinohydrazide (0.600 g, 2.78 mmol) was added to the reaction mixture. Reaction temperature was brought to rt and was stirred for 5 h. Water (50 ml) was added and the mixture was extracted with EtOAc (2×50 ml). The combined organic phase was dried over Na₂SO₄, filtered and concentrated under reduced pressure. The resulting residue was purified by Flash column chromatography (silica; 40% EtOAc in n-hexane) to give tert-butyl (R)-3-(2-(4-bromopicolinoyl)hydrazine-1-carbonyl)-3-fluoropiperidine-1-carboxylate (0.900 g, 2.02 mmol). LCMS: Method C, 1.624 min, MS: ES+ 447.30.

Step c.

To a stirred solution of tert-butyl (R)-3-(2-(4-bromopicolinoyl)hydrazine-1-carbonyl)-3-fluoropiperidine-1-carboxylate (0.870 g, 1.96 mmol) in DCM (9 ml) was added DIPEA (0.156 g, 1.21 mmol) followed by PTS-Cl (0.557 g, 2.93 mmol) portionwise and sodium sulfate (0.555 g, 3.91 mmol) at 0° C. The reaction temperature was brought to rt and stirring continued for 1 h. Water (100 ml) was added into the reaction mass and was extracted with EtOAc (2×100 ml). Combined organic extracts were dried over anhydrous Na₂SO₄, filtered and concentrated under reduced pressure. The resulting residue was purified by flash column chromatography (20% EtOAc in n-hexane) to give tert-butyl (R)-3-(5-(4-bromopyridin-2-yl)-1,3,4-oxadiazol-2-yl)-3-fluoropiperidine-1-carboxylate (0.750 g, 1.76 mmol). LCMS: Method C, 1.748 min, MS: ES+ 427.45.

Step d.

To a stirred solution of tert-butyl (R)-3-(5-(4-bromopyridin-2-yl)-1,3,4-oxadiazol-2-yl)-3-fluoropiperidine-1-carboxylate (0.300 g, 0.70 mmol) in DMF:water (30:1, 3.1 ml) was added NaHCO₃ (0.177 g, 2.11 mmol) and 4-(4,4,5,5-tetramethyl-1,3,2-dioxaborolan-2-yl)picolinonitrile (0.323 g, 1.40 mmol). Reaction mixture was de-gassed with nitrogen for 15 min before addition of PdCl₂(dppf) (0.051 g, 0.07 mmol) and the resulting mixture was heated to 100° C. for 2 h. Water (50 ml) was added into the reaction mass and extracted with EtOAc (2×50 ml). The combined organic extracts were further washed with water (3×50 ml), dried over anhydrous Na₂SO₄, filtered and concentrated under reduced pressure. The resulting residue was purified by flash column chromatography (30% EtOAc in n-hexane) to give tert-butyl (R)-3-(5-(2'-cyano-[4,4'-bipyridin]-2-yl)-1,3,4-oxadiazol-2-yl)-3-fluoropiperidine-1-carboxylate (0.310 g, 0.69 mmol). LCMS: Method C, 1.801 min, MS: ES+ (MH-56) 395.4.

Steps e, f.

The title compound was synthesised from the intermediate above using a procedure similar to that described for Example 1, steps c, d. LCMS: Method A, 3.195 min, MS: ES+ 376.2; ¹H NMR (400 MHz, DMSO-d6) δ ppm: 9.02 (d, J=5.2 Hz, 1H), 8.96 (d, J=5.2 Hz, 1H), 8.74 (d, J=5.6 Hz, 2H), 8.35 (dd, J=4.8 Hz, 1.6 Hz, 1H), 8.23 (dd, J=5.2 Hz, 1.6 Hz, 1H), 4.12-3.82 (m, 2H), 3.49-3.45 (m, 1H), 3.30-3.25 (m, 1H), 2.50-2.25 (m, 2H), 2.00-1.95 (m, 1H), 1.81-1.78 (m, 1H).

EXAMPLE 14

3-(6-(H-pyrazol-5-yl)-1H-benzo[d]imidazol-2-yl)-3-fluoropiperidine-1-carbonitrile

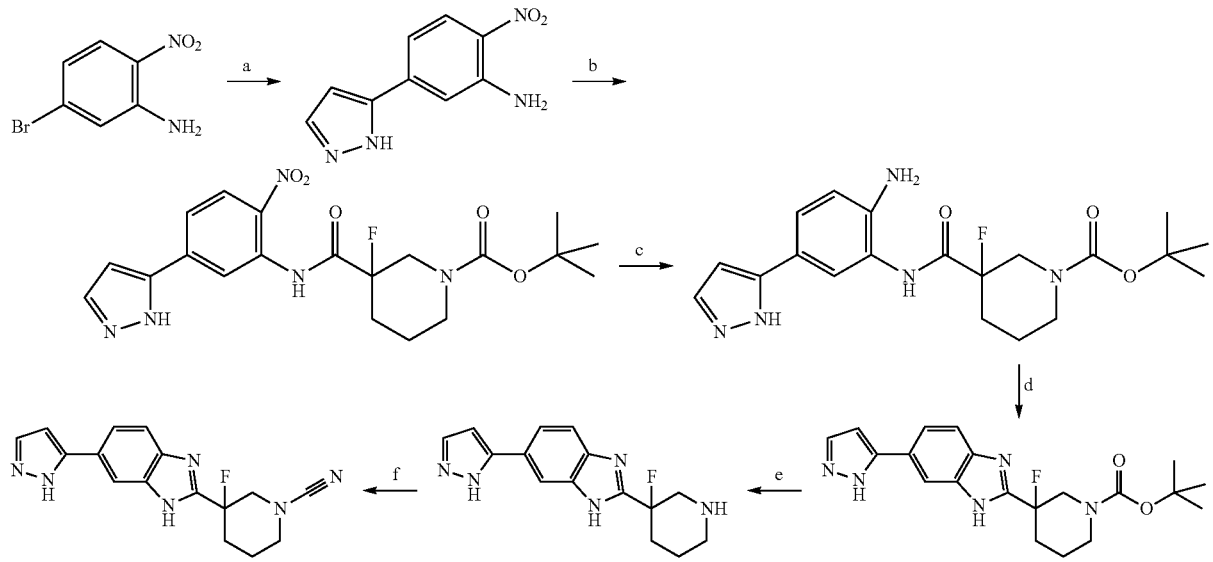

Step a.

To a stirred solution of 5-bromo-2-nitroaniline (CAS Number 5228-61-5; 0.700 g, 3.23 mmol) and 1H-pyrazol-5-ylboronic acid (CAS Number 376584-63-3; 0.720 g, 6.45 mmol) in DMF:water (2:1; 9 ml) was added Na₂CO₃ (1.03 g, 9.68 mmol) at rt. The reaction mixture was degassed with nitrogen for 20 min and PdCl₂(dppf) (0.166 g, 0.23 mmol) was added. The mixture was heated at 130° C. for 1 h under microwave irradiation. The reaction mixture was cooled to rt, poured into water (40 ml) and was extracted with EtOAc (2×40 ml). Combined organic extracts were dried over anhydrous Na₂SO₄, filtered and concentrated under reduced pressure. The resulting residue was purified by flash column chromatography (60% EtOAc in hexane) to give 2-nitro-5-(1H-pyrazol-5-yl) aniline (0.69 g, Quantitative). LCMS: Method C, 1.568 min, MS: ES+ 205.38.

Step b.

To a stirred solution of 2-nitro-5-(1H-pyrazol-5-yl)aniline (0.522 g, 2.56 mmol) and 1-(tert-butoxycarbonyl)-3-fluoropiperidine-3-carboxylic acid (CAS Number 934342-39-9; 0.758 g, 3.07 mmol) in DCM (20 ml) was added pyridine (1.03 ml, 12.79 mmol). The reaction mixture was cooled to 0° C. and POCl₃ (0.74 ml, 7.68 mmol) was added drop-wise into the reaction mixture. The reaction mixture was stirred at 0° C. for 1 h. The reaction mixture was poured into an aqueous solution of saturated NaHCO₃ solution (40 ml) and extracted with DCM (2×40 ml). The combined organic extracts were dried over anhydrous Na₂SO₄, filtered and concentrated under reduced pressure to yield tert-butyl 3-fluoro-3-((2-nitro-5-(1H-pyrazol-5-yl)phenyl)carbamoyl)-piperidine-1-carboxylate (1.27 g, 2.93 mmol; Crude). This crude material directly used to the next step without further purification. LCMS: Method C, 2.162 min, MS: ES+ 434.63.

Step c.

Hydrazine hydrate (6.3 ml, 5 vol) was added dropwise to formic acid (12.15 g, 263.97 mmol) at 0° C. and stirred at rt for 20 min. The above solution (6 ml) was added dropwise to a suspension of tert-butyl 3-fluoro-3-((2-nitro-5-(1H-pyrazol-5-yl)phenyl)carbamoyl)piperidine-1-carboxylate (1.27 g, 2.93 mmol) and zinc dust (1.92 g, 29.33 mmol) in MeOH:THF mixture (1:1, 60 ml) at 0° C. and stirred for 16 h at rt. The reaction mixture was poured into water:EtOAc mixture (1:1, 100 ml) and basified with solid NaHCO₃. The organic layer was separated and aqueous layer was extracted with EtOAc (50 ml). Combined organic extracts were dried over anhydrous Na₂SO₄, filtered and concentrated under reduced pressure to obtain tert-butyl 3-((2-amino-5-(1H-pyrazol-5-yl)phenyl)carbamoyl)-3-fluoropiperidine-1-carboxylate (1.0 g, Crude), which was taken to next step without further purification. LCMS: Method C, 1.707 min, MS: ES+ 404.51.

Step d.

A stirred solution of tert-butyl 3-((2-amino-5-(1H-pyrazol-5-yl)phenyl)carbamoyl)-3-fluoropiperidine-1-carboxylate (0.970 g, 2.40 mmol) in acetic acid (9.7 ml, 10 vol) was heated at 60° C. for 45 min. The reaction mixture was cooled to rt, poured into an aqueous solution of saturated NaHCO₃ (100 ml) and extracted with EtOAc (2×50 ml). The combined organic extracts were dried over anhydrous Na₂SO₄, filtered and concentrated under reduced pressure. The resulting residue was purified by flash column chromatography (70% EtOAc in hexane) to yield tert-butyl 3-(6-(1H-pyrazol-5-yl)-1H-benzo[d]imidazol-2-yl)-3-fluoropiperidine-1-carboxylate (0.346 g, 0.90 mmol). LCMS: Method C, 1.752 min, MS: ES+ 386.53.

Steps e, f.

The title compound was synthesised from the intermediate above using a procedure similar to that described for Example 1, steps c, d. LCMS: Method B, 2.958 min, MS: ES+ 311.4; ¹H NMR (400 MHz, DMSO-d6+drop TFA) δ ppm: 8.14 (s, 1H), 7.96 (d, J=8.4 Hz, 1H), 7.88 (s, 1H), 7.80 (d, J=8.4 Hz, 1H), 6.91 (s, 1H), 3.98-3.92 (m, 1H), 3.76 (dd, J=34.0 Hz, 14.4 Hz, 1H), 3.53-3.50 (m, 1H), 3.25-3.22 (m, 1H), 2.35-2.33 (m, 1H), 2.28-2.22 (m, 1H), 2.05-2.98 (m, 1H), 1.82-1.79 (m, 1H).

EXAMPLE 15

(R)-3-fluoro-3-(5-phenyl-3H-imidazo[4,5-b]pyridin-2-yl)piperidine-1-carbonitrile

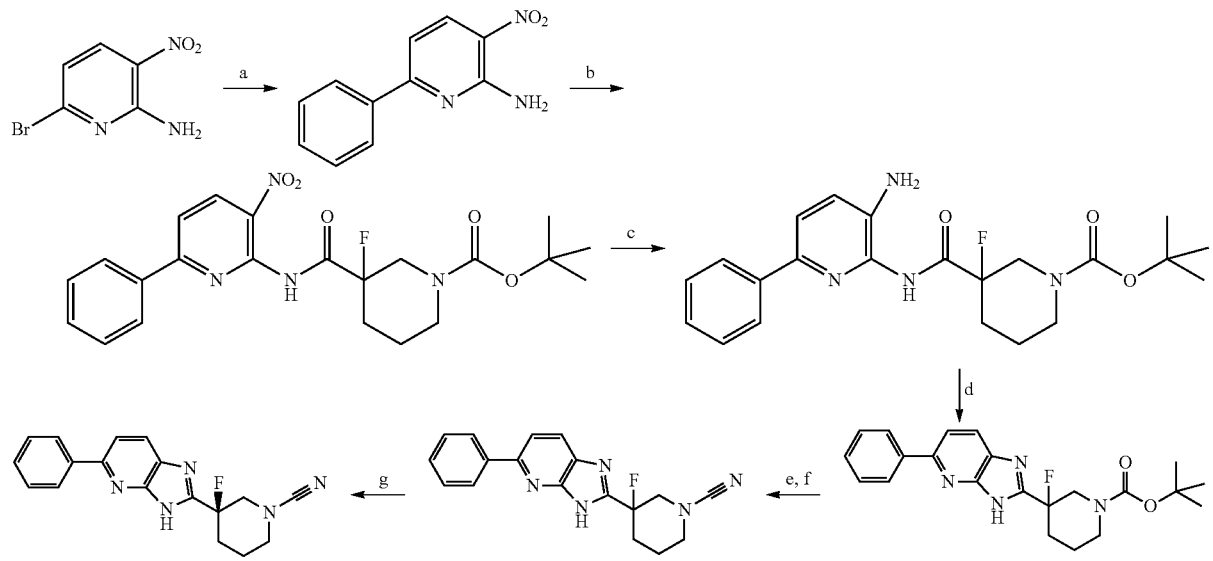

Step a.
To a stirred solution of 6-bromo-3-nitropyridin-2-amine (CAS Number 84487-04-7; 0.500 g, 2.29 mmol) in DME-water-EtOH mixture (5:0.25:0.25; 5.5 ml) was added Na$_2$CO$_3$ (0.360 g, 3.44 mmol) and phenylboronic acid (0.550 g, 4.59 mmol) at rt. The reaction mixture was degassed with nitrogen gas for 15 min and Pd(PPh$_3$)$_4$ (0.053 g, 0.05 mmol) was added into the reaction mixture at the same temperature. The resulting reaction mixture was heated at 100° C. for 30 min under microwave irradiation then cooled to rt. Two parallel reactions with 500 mg (each) of 6-bromo-3-nitropyridin-2-amine were carried out under similar reaction conditions and all three batches were combined prior to work-up. The combined mixtures were poured into water (50 ml) and were extracted with EtOAc (2×50 ml). Combined organic extracts were dried over anhydrous Na$_2$SO$_4$, filtered and concentrated under reduced pressure. The resulting residue was purified by flash column chromatography (3% EtOAc in hexane) yielding 3-nitro-6-phenylpyridin-2-amine (0.280 g, 1.34 mmol). LCMS: Method C, 1.979 min, MS: ES+ 216.28.
Step b.
To a stirred solution of 3-nitro-6-phenylpyridin-2-amine (0.800 g, 3.72 mmol), 1-(tert-butoxycarbonyl)-3-fluoropiperidine-3-carboxylic acid (CAS Number 934342-39-9; 1.10 g, 4.47 mmol) and pyridine (1.49 ml, 18.6 mmol) in DCM (8 ml) was added POCl$_3$ (1.06 ml, 11.16 mmol) dropwise at 0° C. The reaction mixture was slowly warmed to rt and stirred for 16 h. The reaction mixture was poured into water (50 ml) and extracted with DCM (2×50 ml). Combined organic extracts were dried over anhydrous Na$_2$SO$_4$, filtered and concentrated under reduced pressure. The residue was purified by flash column chromatography (24% EtOAc in Hexane) yielding tert-butyl 3-fluoro-3-((3-nitro-6-phenylpyridin-2-yl) carbamoyl) piperidine-1-carboxylate (0.600 g, 1.35 mmol). LCMS: Method C, 2.424 min, MS: ES+ 445.58.
Step c.
To a stirred solution of tert-butyl 3-fluoro-3-((3-nitro-6-phenylpyridin-2-yl) carbamoyl) piperidine-1-carboxylate (0.510 g, 1.15 mmol) in EtOH: water mixture (5:1; 6 ml) was added NH$_4$Cl (0.904 g, 17.22 mmol) at rt and the resulting mixture was refluxed for 15 min. Iron powder (0.224 g, 4.02 mmol) was added at rt and heated to reflux for an additional 2 h. After cooling to rt, the mixture was poured into water (50 ml) and was extracted with EtOAc (2×50 ml). Combined organic extracts were dried over anhydrous Na$_2$SO$_4$, filtered and concentrated under reduced pressure. The residue was purified by flash column chromatography (26.5% EtOAc in hexane) yielding tert-butyl 3-((3-amino-6-phenylpyridin-2-yl)carbamoyl)-3-fluoro-piperidine-1-carboxylate (0.245 g, 0.59 mmol). LCMS: Method C, 2.121 min, MS: ES+ 415.57.
Step d.
A stirred solution of tert-butyl 3-((3-amino-6-phenylpyridin-2-yl)carbamoyl)-3-fluoro-piperidine-1-carboxylate (0.220 g, 0.53 mmol) in acetic acid (0.3 ml) was heated at 60° C. for 1 h. After cooling to rt, the reaction mixture was poured into an aqueous solution of saturated NaHCO$_3$ (30 ml) and was extracted with EtOAc (3×30 ml). Combined organic extracts were dried over anhydrous Na$_2$SO$_4$, filtered and concentrated under reduced pressure to give tert-butyl 3-fluoro-3-(5-phenyl-3H-imidazo[4,5-b]pyridin-2-yl)piperidine-1-carboxylate (0.145 g, 0.366 mmol; Crude). This crude was taken to next step without further purification. LCMS: Method C, 2.173 min, MS: ES+ 397.43.
Steps e, f.
The title compound was synthesised from the intermediate above using a procedure similar to that described for Example 1, steps c, d.
Step g.
Separation of the racemate by chiral SFC provided the title compound as the second eluting isomer under the following conditions: Waters SFC 200 and UV detector, using a Chiralpak IC 250×21 mm, 5 μM, column flow was 75.0 ml/min, mobile phase: (A) liquid carbon dioxide and (B) IPA, isocratic gradient of 25% B over 11 minutes. LCMS: Method B, 3.543 min, MS: ES+ 340.2; $^1$H NMR (400 MHz, DMSO-d6) δ ppm: 8.11 (d, J=7.6 Hz, 3H), 7.88 (d, J=8.4 Hz, 1H), 7.51 (t, J=7.6 Hz, 2H), 7.44 (d, J=7.2 Hz, 1H), 3.8-3.73 (m, 2H), 3.84-3.45 (m, 2H), 3.33-3.24 (m, 2H), 1.99-1.96 (m, 1H), 1.78-1.75 (m, 1H).

EXAMPLE 16

(S)-3-(5-(3-cyanophenyl)-3H-imidazo[4,5-b]pyridin-2-yl)-3-fluoropiperidine-1-carbonitrile

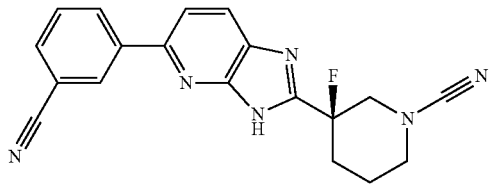

The title compound was synthesised as a racemate using a procedure similar to that described for Example 15, steps a-f, using 3-cyanophenylboronic acid (CAS Number 150255-96-2) in step a. Separation of the racemate by chiral SFC provided the title compound as the first eluting isomer under the following conditions: Waters SFC 200 and UV detector, using a Chiralpak IC 250×21 mm, 5 μM, column flow was 75.0 ml/min, mobile phase: (A) liquid carbon dioxide and (B) IPA, isocratic gradient of 25% B over 11 minutes. LCMS: Method A, 3.316 min, MS: ES+ 347.1; $^1$H NMR (400 MHz, DMSO-d6) δ ppm: 13.50 (br, 1H), 8.55 (s, 1H), 8.48 (d, J=8.0 Hz, 1H), 8.14 (d, J=8.0 Hz, 1H), 8.00 (d, J=8.4 Hz, 1H), 7.90 (d, J=7.6 Hz, 1H), 7.73 (t, J=8.0 Hz, 1H), 3.92-3.74 (m, 2H), 3.49-3.46 (m, 1H), 3.30-3.23 (m, 1H), 2.42-2.19 (m, 2H), 2.01-1.92 (m, 1H), 1.79-1.75 (m, 1H).

EXAMPLE 17

3-(5-(1H-pyrazol-5-yl)-3H-imidazo[4,5-b]pyridin-2-yl)-3-fluoropiperidine-1-carbonitrile

The title compound was synthesised as a racemate using a procedure similar to that described for Example 15, steps a-f, using (1-(tert-butoxycarbonyl)-1H-pyrazol-3-yl)boronic acid (CAS Number 1162261-97-3) in step a. LCMS: Method A, 2.298 min, MS: ES+ 348; $^1$H NMR (400 MHz, DMSO-d6) δ ppm: 8.89 (d, J=2.0 Hz, 1H), 8.79 (d, J=2.0 Hz, 1H), 8.36 (s, 1H), 8.19 (d, J=8.0 Hz, 1H), 7.94 (d, J=8.0 Hz, 1H), 7.76 (t, J=8.4 Hz, 1H), 4.04-3.82 (m, 2H), 3.49-3.46 (m, 1H), 3.35-3.25 (m, 1H), 2.50-2.19 (m, 2H), 2.04-1.95 (m, 1H), 1.81-1.78 (m, 1H).

EXAMPLE 18

(R)-4-(2-(1-cyano-3-fluoropiperidin-3-yl)-3H-imidazo[4,5-b]pyridin-6-yl)picolinonitrile

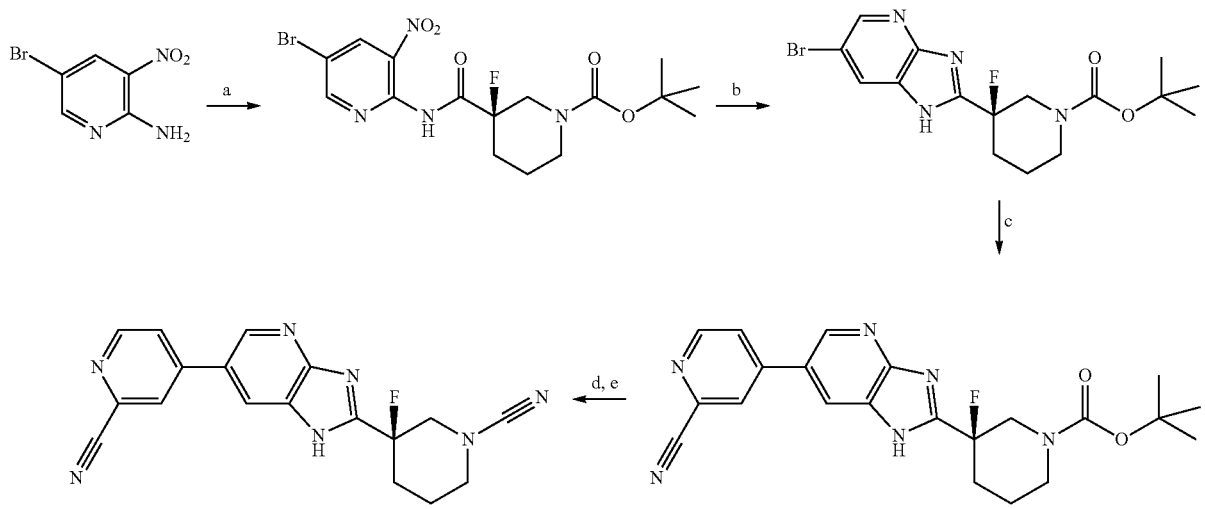

Step a.

To a stirred solution of 1-(tert-butoxycarbonyl)-3-fluoropiperidine-3-carboxylic acid (0.200 g, 0.81 mmol) and 5-bromo-3-nitropyridin-2-amine (CAS Number 6945-68-2; 0.264 g, 1.21 mmol) in pyridine (5 ml) was added POCl$_3$ (0.7 ml, 8.09 mmol) at 0° C. and stirred at rt for 40 min. The resulting reaction mixture was poured into water (100 ml) and was extracted with EtOAc (2×100 ml). Combined organic extracts were dried over anhydrous Na$_2$SO$_4$, filtered and concentrated under reduced pressure to give crude residue, which was purified by column chromatography (15% EtOAc in hexane) to obtain tert-butyl 3-((5-bromo-3-nitropyridin-2-yl)carbamoyl)-3-fluoropiperidine-1-carboxylate (0.180 g, 0.40 mmol). LCMS: Method C, 1.745 min, MS: ES+ 447.5.

Step b.

To a stirred solution of tert-butyl 3-((5-bromo-3-nitropyridin-2-yl)carbamoyl)-3-fluoropiperidine-1-carboxylate (0.160 g, 0.36 mmol) in THF:water (1:1; 3 ml) was added iron powder (0.100 g, 1.79 mmol) followed by acetic acid (1.6 ml, 10 vol.) at rt. The resulting reaction mixture was heated at 130° C. for 5 h. Reaction mixture was poured in to water (100 ml), basified (pH ~10) by solid $NaHCO_3$ and extracted with EtOAc (2×100 ml). Combined organic extracts were dried over anhydrous $Na_2SO_4$, filtered and concentrated under reduced pressure to give tert-butyl 3-(6-bromo-3H-imidazo[4,5-b]pyridin-2-yl)-3-fluoropiperidine-1-carboxylate (0.14 g, 0.35 mmol; Crude), which was taken to the next step without further purification. LCMS: Method C, 1.660 min, MS: ES+399.3.

Step c.

To a stirred solution tert-butyl 3-(6-bromo-3H-imidazo[4,5-b]pyridin-2-yl)-3-fluoropiperidine-1-carboxylate (0.110 g, 0.28 mmol) and 4-(4,4,5,5-tetramethyl-1,3,2-dioxaborolan-2-yl)picolinonitrile (CAS Number 741709-62-6; 0.095 g, 0.41 mmol) in MeCN:water (5:4; 9 ml) was added KOAc (0.108 g, 1.11 mmol) at rt. The reaction mixture was degassed with nitrogen for 20 min and $PdCl_2(dppf)$ (0.020 g, 0.03 mmol) was added into the reaction mixture. The resulting reaction mixture was heated at 80° C. for 5 h. The mixture was cooled to rt, poured into water (100 ml) and extracted with EtOAc (2×100 ml). The combined organic extracts were dried over anhydrous $Na_2SO_4$, filtered and concentrated under reduced pressure to give crude residue. The crude residue was purified by column chromatography (70% EtOAc in n-hexane) to give tert-butyl 3-(6-(2-cyano-pyridin-4-yl)-3H-imidazo[4,5-b]pyridin-2-yl)-3-fluoropiperidine-1-carboxylate (0.046 g, 0.11 mmol). LCMS: Method C, 1.570 min, MS: ES+ 423.42.

Steps d, e.

The title compound was synthesised from the intermediate above using a procedure similar to that described for Example 1, steps c, d. LCMS: Method A, 2.730 min, MS: ES+ 348.0; $^1$H NMR (400 MHz, DMSO-d6) δ ppm: 13.86 (brs, ½H; tautomer), 13.62 (brs, ½H; tautomer), 8.96 (s, 1H), 8.84 (d, J=5.2 Hz, 1H), 8.69 (s, 1H), 8.60 (s, 1H), 8.24 (dd, J=5.2 Hz, 1.2 Hz, 1H), 3.92-3.75 (m, 2H), 3.50-3.47 (m, 1H), 3.31-3.27 (m, 1H), 2.50-2.19 (m, 2H), 2.01-1.92 (m, 1H), 1.80-1.76 (m, 1H).

EXAMPLE 19

(R)-4-(2-(1-cyano-3-fluoropiperidin-3-yl)-1H-imidazo[4,5-b]pyridin-5-yl)picolinonitrile

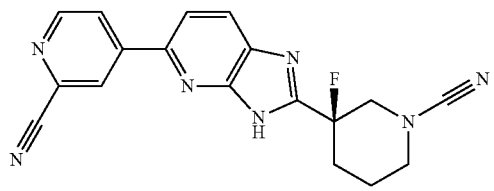 [SMILES: N#Cc1cc(-c2ccc3nc([C@@]4(F)CCCN(C#N)C4)[nH]c3n2)ccn1]

The title compound was synthesised using a procedure similar to that described for Example 18, using 2-amino-6-bromo-3-nitropyridine (CAS Number 84487-04-7) in step a. LCMS: Method A, 3.316 min, MS: ES+ 347.1; $^1$H NMR (400 MHz, DMSO-d6) δ ppm: 13.50 (br, 1H), 8.55 (s, 1H), 8.48 (d, J=8.0 Hz, 1H), 8.14 (d, J=8.0 Hz, 1H), 8.00 (d, J=8.4 Hz, 1H), 7.90 (d, J=7.6 Hz, 1H), 7.73 (t, J=8.0 Hz, 1H), 3.92-3.74 (m, 2H), 3.49-3.46 (m, 1H), 3.30-3.23 (m, 1H), 2.42-2.19 (m, 2H), 2.01-1.92 (m, 1H), 1.79-1.75 (m, 1H).

EXAMPLE 20

3-(6-(3-cyanophenyl)-1H-imidazo[4,5-b]pyridin-2-yl)-3-fluoropiperidine-1-carbonitrile

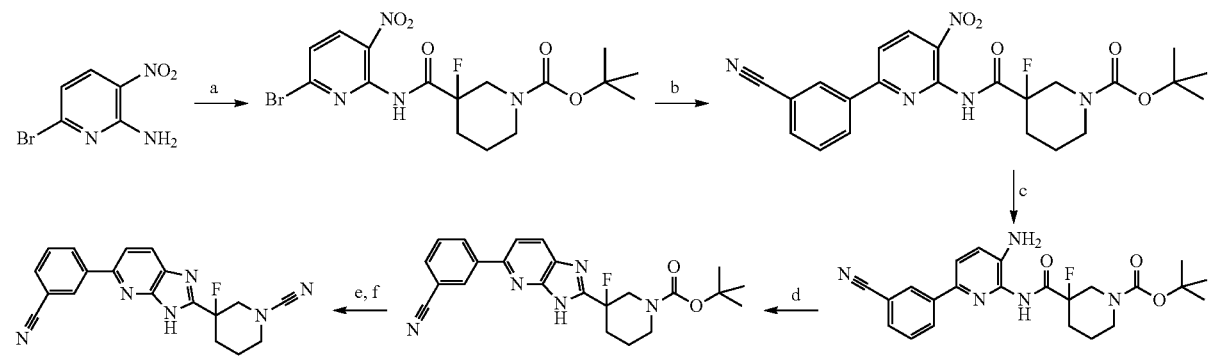

Step a.

To a stirred solution of 1-(tert-butoxycarbonyl)-3-fluoropiperidine-3-carboxylic acid (1.0 g, 4.05 mmol) and 5-bromo-3-nitropyridin-2-amine (1.3 g, 6.07 mmol) in pyridine (15 ml) was added $POCl_3$ (1.85 g, 12.15 mmol) drop-wise at 0° C. and the resulting mixture was stirred at rt for 1 h. The reaction mixture was diluted with water (50 ml) and was extracted with EtOAc (3×50 ml). The combined organic extracts were washed with brine (30 ml), dried over anhydrous $Na_2SO_4$, filtered and concentrated under reduced pressure. The resulting residue was purified by column chromatography (12% EtOAc in Hexane) to yield tert-butyl 3-((5-bromo-3-nitropyridin-2-yl)carbamoyl)-3-fluoropiperidine-1-carboxylate (1.1 g, 2.47 mmol). LCMS: Method C, 1.816 min, MS: ES+ 447.3, 449.3.

Step b.

To a stirred solution of tert-butyl 3-((5-bromo-3-nitropyridin-2-yl)carbamoyl)-3-fluoropiperidine-1-carboxylate (0.400 g, 0.90 mmol) and (3-cyanophenyl)boronic acid (CAS Number 150255-96-2; 0.197 g, 1.35 mmol) in MeCN:water mixture (1:1; 8 ml) was added KOAc (0.351 g, 3.583 mmol). The resulting mixture was degassed with nitrogen for 15 min before addition of PdCl$_2$(dppf) (0.065 g, 0.09 mmol) and the resulting mixture was heated at 80° C. for 12 h. The reaction mixture was cooled to rt, diluted with water (30 ml) and extracted with EtOAc (2×30 ml). The combined organic extracts were washed with brine (20 ml), dried over anhydrous Na$_2$SO$_4$, filtered and concentrated under reduced pressure to give a crude mass, which was purified by flash column chromatography (SiO$_2$; 30% EtOAc in hexane) to provide tert-butyl 3-((5-(3-cyanophenyl)-3-nitropyridin-2-yl)carbamoyl)-3-fluoropiperidine-1-carboxylate (0.200 g, 0.43 mmol). LCMS: Method C, 1.836 min, MS: ES+ 470.35.

Step c.

To a stirred solution of tert-butyl 3-((5-(3-cyanophenyl)-3-nitropyridin-2-yl)carbamoyl)-3-fluoropiperidine-1-carboxylate (0.190 g, 0.40 mmol) in THF:water (1:1; 4 ml) was added NH$_4$Cl (0.226 mg, 4.05 mmol) and iron powder (0.218 g, 4.051 mmol) at rt and the resulting mixture was heated at 60° C. for 4 h, cooled to rt, diluted with water (30 ml) and extracted with EtOAc (3×30 ml). The combined organic extracts were washed with brine (20 ml), dried over anhydrous Na$_2$SO$_4$, filtered and concentrated under reduced pressure to give tert-butyl 3-((3-amino-5-(3-cyanophenyl)pyridin-2-yl)carbamoyl)-3-fluoropiperidine-1-carboxylate (0.180 g, 0.41 mmol; Crude). The crude material was carried to the next step without further purification. LCMS: Method C, 1.591 min, MS: ES+ 440.50.

Steps d-f.

The title compound was synthesised from the intermediate above using a procedure similar to that described for Example 15, steps d-f. LCMS: Method B, 3.279 min, MS: ES+ 347.2; $^1$H NMR (400 MHz, DMSO-d6+drop TFA) δ ppm: 8.89 (s, 1H), 8.55 (s, 1H), 8.32 (s, 1H), 8.15 (d, J=8.0 Hz, 1H), 7.89 (d, J=7.6 Hz, 1H), 7.73 (t, J=8.0 Hz, 1H), 3.89-3.78 (m, 2H), 3.51-3.45 (m, 1H), 3.25-3.22 (m, 1H), 2.50-2.33 (m, 2H), 2.05-1.95 (m, 1H), 1.85-1.75 (m, 1H).

EXAMPLE 21

(R)-6-(2-(1-cyano-3-fluoropiperidin-3-yl)-3H-imidazo[4,5-b]pyridin-5-yl)picolinonitrile

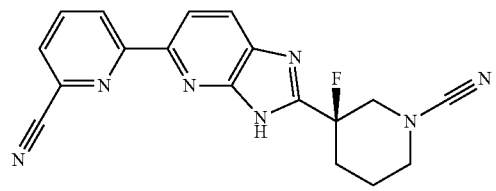 [SMILES: N#Cc1cccc(-c2ccc3nc([C@@]4(F)CCCN(C#N)C4)[nH]c3n2)n1]

To a stirred solution of 6-bromopicolinonitrile (CAS Number 122918-25-6; 0.400 g, 2.19 mmol) in 1,2-DME-DMF mixture (8:1, 9 ml) was added hexabutylditin (1.900 g, 3.28 mmol) at rt. The reaction mixture was degassed with nitrogen for 30 min before addition of Pd(PPh$_3$)$_4$ (0.224 g, 0.19 mmol) and the resulting mixture was heated at 100° C. for 8 h. The reaction mixture was cooled to rt, diluted with ice water (100 ml) and extracted with EtOAc (2×100 ml). The combined organic extracts were dried over anhydrous Na$_2$SO$_4$, filtered and concentrated under reduced pressure. The obtained residue was purified by flash column chromatography (10% EtOAc in hexane) to give 6-(tributylstannyl)-picolinonitrile (0.350 g, 0.89 mmol). LCMS: Method C, 3.515 min, MS: ES+ 395.58.

The title compound was synthesised using a procedure similar to that described for Example 18, using 2-amino-6-bromo-3-nitropyridine (CAS Number 84487-04-7) in step a and 6-(tributylstannyl)-picolinonitrile (as described above) in step c. LCMS: Method A, 3.264 min, MS: ES+ 348; $^1$H NMR (400 MHz, DMSO-d6) δ ppm: 13.85 (brs, ½H; tautomer), 13.45 (brs, ½H; tautomer), 8.72-8.67 (m, 1H), 8.37 (br, 1H), 8.26-8.22 (m, 2H), 8.11-8.09 (m, 1H), 3.92-3.75 (m, 2H), 3.50-3.47 (m, 1H), 3.31-3.30 (m, 1H), 2.50-2.22 (m, 2H), 2.01-1.98 (m, 1H), 1.80-1.77 (m, 1H).

EXAMPLE 22

(R)-3-(5-(3-cyanophenyl)benzo[d]oxazol-2-yl)-3-fluoropiperidine-1-carbonitrile

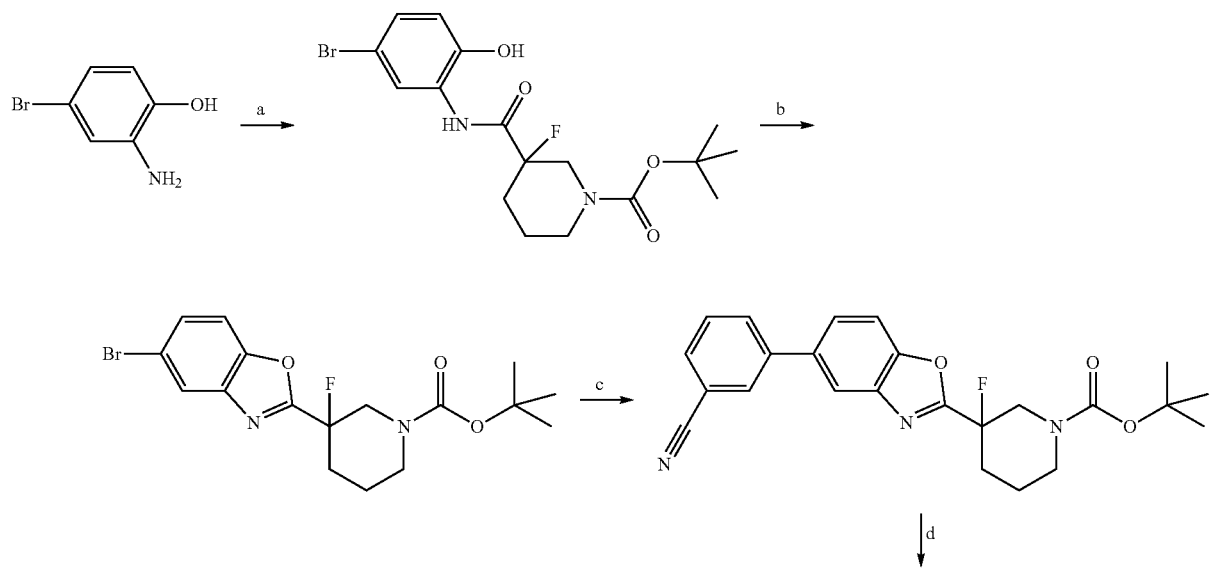

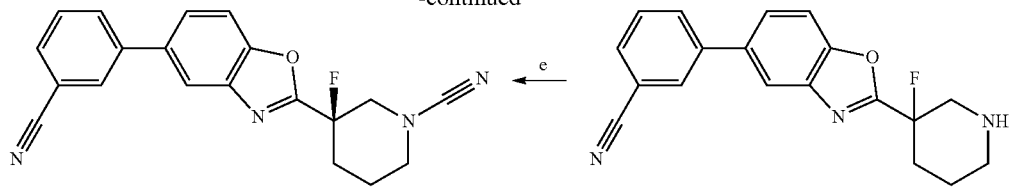

Step a.

To a stirred solution of 2-amino-4-bromophenol (0.400 g, 2.13 mmol) in DCM (10.0 ml) was added EDC.HCl (0.611 g, 3.19 mmol) and HOBt (0.430 g, 3.19 mmol) at rt. The reaction mixture was stirred for 1 h before addition of 1-(tert-butoxycarbonyl)-3-fluoropiperidine-3-carboxylic acid (CAS Number 934342-39-9; 0.525 g, 2.13 mmol). The reaction was stirred at rt for 16 h then poured into water (50 ml) and extracted with DCM (2×100 ml). The combined organic extracts were dried over anhydrous $Na_2SO_4$, filtered and concentrated under reduced pressure to yield tert-butyl 3-((5-bromo-2-hydroxyphenyl)carbamoyl)-3-fluoropiperidine-1-carboxylate (0.43 g, 1.03 mmol; crude). This was taken to next step without further purification. LCMS: Method C, 2.236 min, MS: ES+ 417.19;

Step b.

To a stirred solution of tert-butyl 3-((5-bromo-2-hydroxyphenyl)carbamoyl)-3-fluoro-piperidine-1-carboxylate (0.430 g, 1.03 mmol; crude) in THF (5 ml) was added triphenylphosphine (0.541 g, 2.06 mmol) at rt. After stirring for 20 min, DIAD (0.42 g, 2.06 mmol) was added into the reaction mixture and the resulting mixture was stirred at 70° C. for 4 h. The reaction was poured into water (50 ml) and extracted with EtOAc (2×50 ml). The combined organic extracts were dried over anhydrous $Na_2SO_4$, filtered and concentrated under reduced pressure to give crude residue, which was purified by combi-flash chromatography (15% EtOAc in n-hexane) to obtain tert-butyl 3-(5-bromobenzo[d]oxazol-2-yl)-3-fluoropiperidine-1-carboxylate (0.25 g, 0.62 mmol). LCMS: Method C, 2.493 min, MS: ES+ 399.32; $^1$H NMR (400 MHz, $CDCl_3$) δ ppm: 7.89 (s, 1H), 7.52 (d, J=8 Hz 1H), 7.46 (d, J=8.8 Hz 1H), 4.26-4.39 (m, 1H), 3.87-3.91 (m, 1H), 3.70-3.86 (m, 1H), 3.10-3.16 (m, 1H), 2.25-2.39 (m, 2H), 1.94-2.00 (m, 1H), 1.76-1.79 (m, 1H), 1.42 (s, 9H).

Steps c-e.

The title compound was synthesised as a racemate from the intermediate above using a procedure similar to that described for Example 18, steps c-e. The enantiomers were separated by preparative chiral SFC and the first eluting isomer was assigned as the title compound. LCMS: Method A, 4.173 min, MS: ES+ 347.2; $^1$H NMR (400 MHz, DMSO-d6) δ ppm: 8.27 (s, 2H), 8.12 (d, J=8.0 Hz, 1H), 7.97 (d, J=8.4 Hz, 1H), 7.92-7.87 (m, 2H), 7.72 (t, J=8.0 Hz, 1H), 3.99-3.83 (m, 2H), 3.48-3.45 (m, 1H), 3.29-3.24 (m, 1H), 2.50-2.24 (m, 2H), 2.04-1.95 (m, 1H), 1.81-1.77 (m, 1H).

EXAMPLE 23

(R)-6-(2-(1-cyano-3-fluoropiperidin-3-yl)benzo[d]oxazol-5-yl)pyrimidine-4-carbonitrile

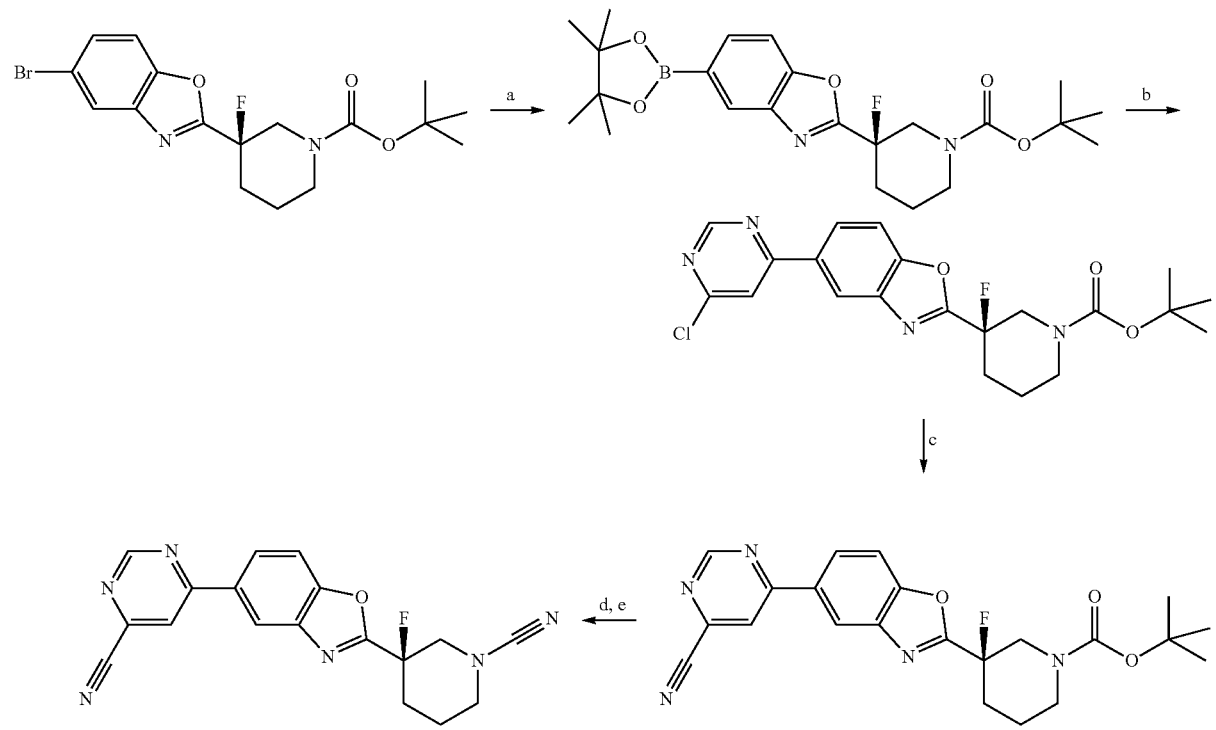

Step a.

To a stirred solution of tert-butyl (R)-3-(5-bromobenzo[d]oxazol-2-yl)-3-fluoropiperidine-1-carboxylate (made according to Example 22, steps a and b, using (R)-1-(tert-butoxycarbonyl)-3-fluoropiperidine-3-carboxylic acid in step a; 0.700 g, 1.75 mmol) in DMF (10 ml) was added KOAc (0.343 g, 3.50 mmol) and bis(pinacolato)diboron (0.668 g, 2.63 mmol) followed by the addition of $PdCl_2$(dppf).DCM complex (0.143 g, 0.18 mmol) and the resulting mixture was heated at 80° C. for 4 h. After cooling to rt, the mixture was poured into water (10 ml) and extracted with EtOAc (3×10 ml). The combined organic extracts were dried over anhydrous $Na_2SO_4$, filtered and concentrated under reduced pressure. The residue was purified by washing with n-hexanes (3×10 ml) and the combined organic extracts were concentrated under reduced pressure to obtain tert-butyl (R)-3-fluoro-3-(5-(4,4,5,5-tetramethyl-1,3,2-dioxaborolan-2-yl)benzo[d]oxazol-2-yl)piperidine-1-carboxylate (0.900 g, crude), which was taken to next step without further purification. LCMS: Method C, 2.196 min, MS: ES+ 447.52.

Step b.

To a stirred solution of tert-butyl (R)-3-fluoro-3-(5-(4,4,5,5-tetramethyl-1,3,2-dioxaborolan-2-yl)benzo[d]oxazol-2-yl)piperidine-1-carboxylate (0.400 g, 0.90 mmol; crude) in 1,4-dioxane:water mixture (8:1, 10 ml) were added $Cs_2CO_3$ (0.584 g, 1.79 mmol) and 4,6-dichloropyrimidine (CAS Number 1193-21-1; 0.200 g, 1.34 mmol) at rt. The reaction was degassed by purging with nitrogen for 5 min before addition of $PdCl_2$(dppf) (0.032 g, 0.044 mmol) and the resulting mixture was heated at 100° C. for 5 h. After cooling to rt, the mixture was poured into water (10 ml) and extracted with EtOAc (3×15 ml). The combined organic extracts were dried over anhydrous $Na_2SO_4$, filtered and concentrated under reduced pressure. The resulting residue was purified by column chromatography (20% EtOAc in Hexane) to give tert-butyl (R)-3-(5-(6-chloropyrimidin-4-yl)benzo[d]oxazol-2-yl)-3-fluoropiperidine-1-carboxylate (0.200 g, 0.46 mmol). LCMS: Method C, 2.044 min, MS: ES+ 433.39.

Step c.

To a stirred solution of tert-butyl (R)-3-(5-(6-chloropyrimidin-4-yl)benzo[d]oxazol-2-yl)-3-fluoropiperidine-1-carboxylate (0.200 g; 0.42 mmol) in DMF (5 ml) was added $Zn(CN)_2$ (0.065 g, 0.56 mmol), $Pd_2(dba)_3$ (0.042 g, 0.05 mmol) and dppf (0.051 g, 0.09 mmol) and the resulting mixture was heated at 130° C. under microwave irradiation for 1 h. After cooling to rt, the mixture was poured into water (5 ml) and extracted with EtOAc (3×5 ml). The combined organic extracts were dried over anhydrous $Na_2SO_4$, filtered and concentrated under reduced pressure to give tert-butyl (R)-3-(5-(6-cyanopyrimidin-4-yl)benzo[d]oxazol-2-yl)-3-fluoropiperidine-1-carboxylate (0.200 g, crude), which was taken to next step without purification. LCMS: Method C, 1.943 min, MS: ES+ 424.4.

Steps d, e.

The title compound was synthesised from the intermediate above using a procedure similar to that described for Example 1, steps c, d. LCMS: Method B, 3.827 min, MS: ES+ 349.5 (M+H+); $^1$H NMR (400 MHz, DMSO-d6) δ ppm: 9.48 (s, 1H), 8.95 (s, 1H), 8.80 (s, 1H), 8.49 (d, J=8.8 Hz, 1H), 8.07 (d, J=8.8 Hz, 1H), 4.00-3.83 (m, 2H), 3.48-3.45 (m, 1H), 3.30-3.24 (m, 1H), 2.50-2.25 (m, 2H), 2.04-1.95 (m, 1H), 1.81-1.77 (m, 1H)

EXAMPLE 24

(R)-2-(2-(1-cyano-3-fluoropiperidin-3-yl)benzo[d]oxazol-5-yl)pyrimidine-4-carbonitrile

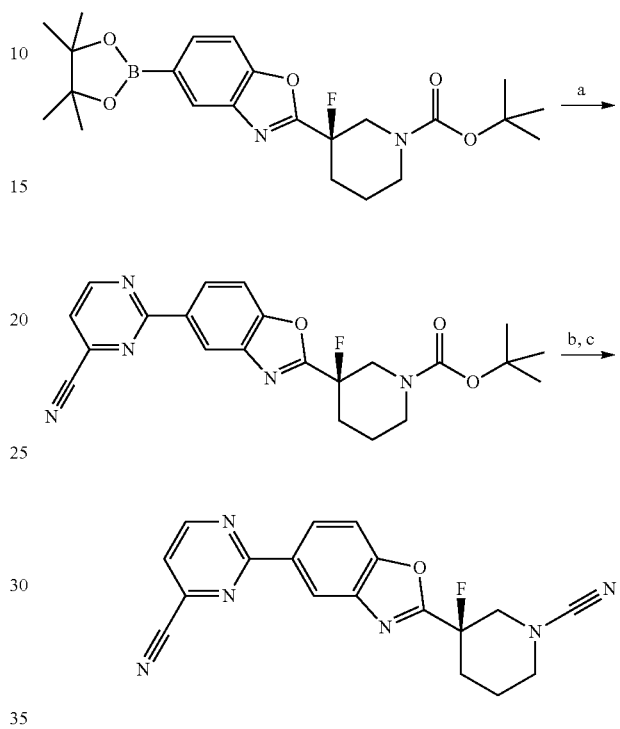

Step a.

To a stirred solution of tert-butyl (R)-3-fluoro-3-(5-(4,4,5,5-tetramethyl-1,3,2-dioxaborolan-2-yl)benzo[d]oxazol-2-yl)piperidine-1-carboxylate (made according to Example 23, step a; 0.08 g, 0.18 mmol) in 1,4-dioxane:water mixture (4:1; 5 ml) was added 2-chloro-pyrimidine-4-carbonitrile (0.025 mg, 0.18 mmol) followed by addition of $Cs_2CO_3$ (0.116 g, 0.39 mmol) at rt. The resulting reaction mixture was degassed (by purging nitrogen through the mixture) for 10 min before addition of $PdCl_2$(dppf) (0.007 g, 0.01 mmol) and resulting mixture was heated at 80° C. for 4 h. The reaction mixture was cooled to rt, diluted with water (5 ml) and extracted with EtOAc (3×5 ml). The combined organic extracts were dried over anhydrous $Na_2SO_4$, filtered and concentrated under reduced pressure. The residue was purified by column chromatography (30% EtOAc in hexane) to yield tert-butyl (R)-3-(5-(4-cyanopyrimidin-2-yl)benzo[d]oxazol-2-yl)-3-fluoro-piperidine-1-carboxylate. (0.07 g, 0.17 mmol). LCMS: Method C, 1.902 min, MS: ES+ 424.37.

Steps b, c.

The title compound was synthesised from the intermediate above using a procedure similar to that described for Example 1, steps c, d. LCMS: Method B, 3.930 min, MS: ES+ 349.4 (M–H+); $^1$H NMR (400 MHz, DMSO-d6) δ ppm: 9.29 (d, J=5.2 Hz, 1H), 8.76 (d, J=1.2 Hz, 1H), 8.56 (dd, J=8.8 Hz, 1.6 Hz, 1H), 8.12 (d, J=4.8 Hz, 1H), 8.03 (d, J=8.8 Hz, 1H), 3.95-3.82 (m, 2H), 3.48-3.44 (m, 1H), 3.29-3.24 (m, 1H), 2.50-2.27 (m, 2H), 2.00-1.97 (m, 1H), 1.80-1.76 (m, 1H)

EXAMPLE 25

(R)-4-(2-(1-cyano-3-fluoropiperidin-3-yl)benzo[d]oxazol-5-yl)picolinonitrile

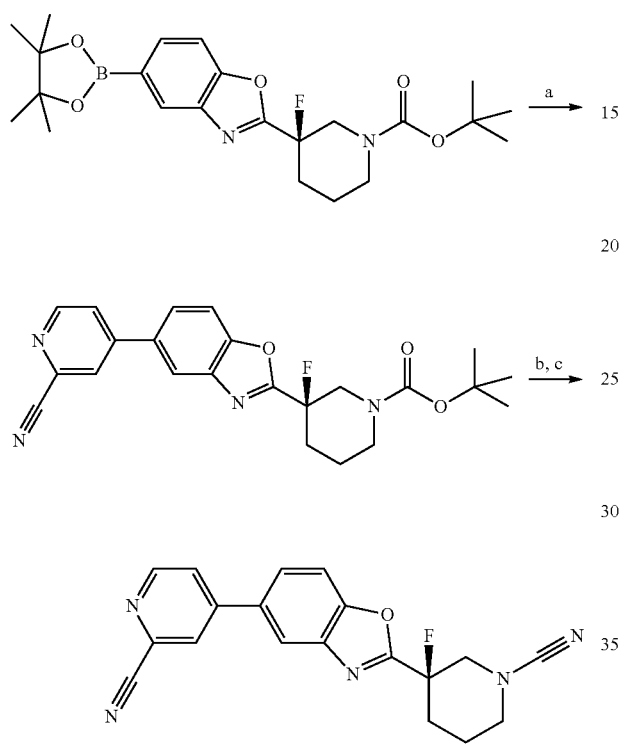

Step a.

To a stirred solution of tert-butyl (R)-3-fluoro-3-(5-(4,4,5,5-tetramethyl-1,3,2-dioxaborolan-2-yl)benzo[d]oxazol-2-yl)piperidine-1-carboxylate (made according to Example 23, step a; 0.200 g, 0.45 mmol) in 1,4-dioxane:water (4:1, 10 ml) was added $Cs_2CO_3$ (0.292 g, 0.90 mmol) and 4-bromopicolinonitrile (0.123 g, 0.67 mmol). The reaction mixture was degassed with nitrogen for 10 min before addition of $PdCl_2$(dppf) and the reaction was heated to 80° C. for 4 h. The reaction mixture was cooled to rt, poured into water (5 ml) and extracted with EtOAc (3×5 ml). The combined organic extracts were dried over anhydrous $Na_2SO_4$, filtered and concentrated under reduced pressure to give a crude mass, which was purified by column chromatography (20% EtOAc in n-hexane) to obtain tert-butyl (R)-3-(5-(2-cyanopyridin-4-yl)benzo[d]oxazol-2-yl)-3-fluoropiperidine-1-carboxylate (0.110 g, 0.261 mmol). LCMS: Method C, 1.914 min, MS: ES+ 423.5.

Steps b, c.

The title compound was synthesised from the intermediate above using a procedure similar to that described for Example 1, steps c, d. LCMS: Method B, 3.965 min, MS: ES+ 348.3 (M−H$^+$); $^1$H NMR (400 MHz, DMSO-d6) δ ppm: 8.84 (d, J=4.0 Hz, 1H), 8.56 (s, 1H), 8.49 (s, 1H), 8.20 (dd, J=4.0 Hz, 1.2 Hz, 1H), 8.10-8.03 (m, 2H), 4.00-3.84 (m, 2H), 3.49-3.46 (m, 1H), 3.30-3.25 (m, 1H), 2.50-2.25 (m, 2H), 2.04-1.95 (m, 1H), 1.81-1.78 (m, 1H).

EXAMPLE 26

(R)-2-(2-(1-cyano-3-fluoropiperidin-3-yl)benzo[d]oxazol-5-yl)isonicotinonitrile

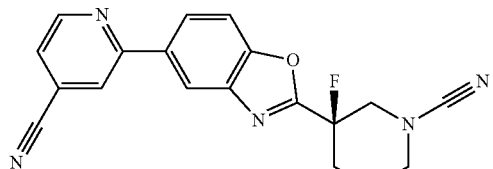

The title compound was synthesised using a procedure similar to that described for Example 25, using 2-bromo-4-cyanopyridine in step a. LCMS: Method B, 3.983 min, MS: ES+ 348.4; $^1$H NMR (400 MHz, DMSO-d6) δ ppm: 8.96 (d, J=5.2 Hz, 1H), 8.65 (s, 2H), 8.36 (d, J=8.8 Hz, 1H), 8.00 (d, J=8.8 Hz, 1H), 7.88 (d, J=4.8 Hz, 1H), 3.96-3.83 (m, 2H), 3.48-3.45 (m, 1H), 3.30-3.24 (m, 1H), 2.50-2.26 (m, 2H), 2.04-1.98 (m, 1H), 1.81-1.77 (m, 1H).

EXAMPLE 27

(R)-4-(2-(1-cyano-3-fluoropiperidin-3-yl)benzo[d]oxazol-6-yl)picolinonitrile

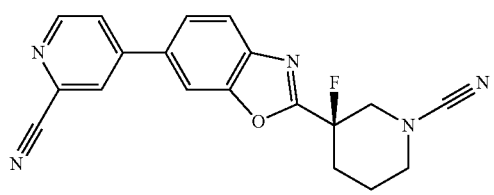 [SMILES: N#Cc1cc(-c2ccc3nc([C@@]4(F)CCCN(C#N)C4)oc3c2)ccn1]

The title compound was synthesised using a procedure similar to that described for Example 25, using 2-amino-5-bromophenol in step a. LCMS: Method A, 3.705 min, MS: ES+ 348; $^1$H NMR (400 MHz, DMSO-d6) δ ppm: 8.86 (d, J=5.2 Hz, 1H), 8.57 (s, 1H), 8.48 (s, 1H), 8.21 (dd, J=5.2 Hz, 1.6 Hz, 1H), 8.04 (s, 1H), 3.95-3.82 (m, 2H), 3.48-3.45 (m, 1H), 3.29-3.23 (m, 1H), 2.50-2.34 (m, 2H), 2.01-1.98 (m, 1H), 1.80-1.77 (m, 1H).

EXAMPLE 28

3-(6-(3-cyanophenyl)oxazolo[5,4-b]pyridin-2-yl)-3-fluoropiperidine-1-carbonitrile

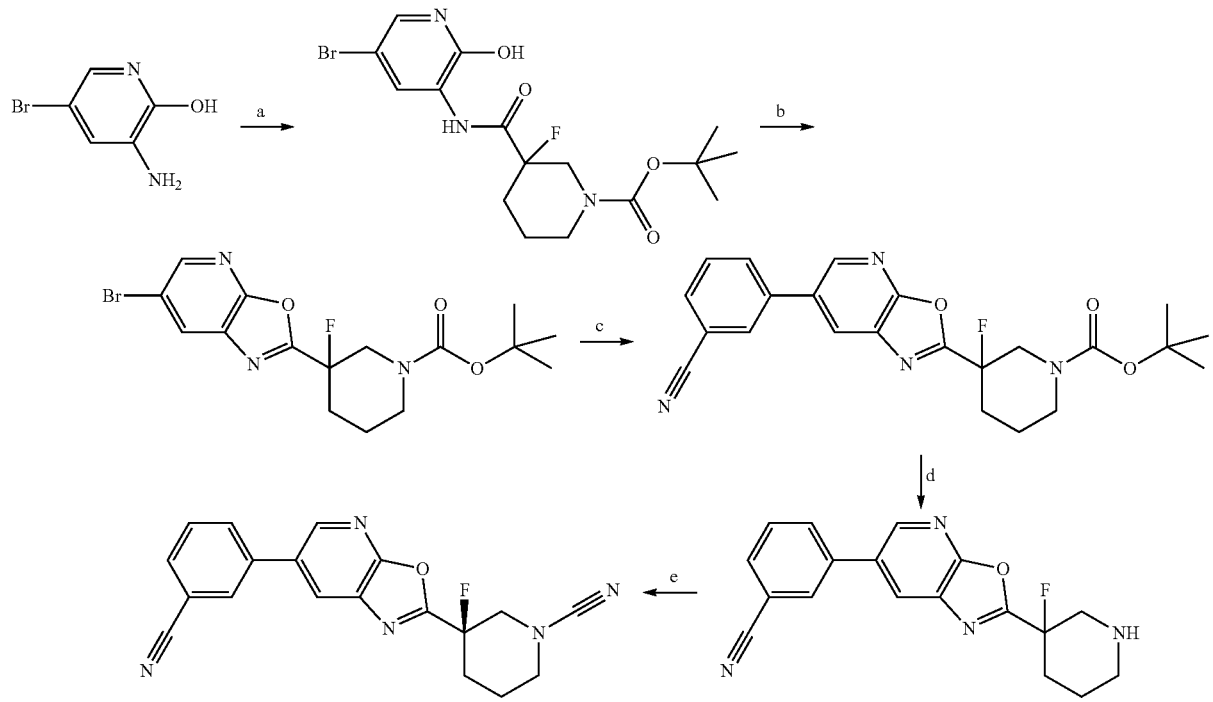

Step a.

To a stirred solution of 1-(tert-butoxycarbonyl)-3-fluoropiperidine-3-carboxylic acid (0.500 g, 2.02 mmol) in THF (8 ml) was added DIPEA (0.523 g, 4.05 mmol) followed by TBTU (0.975 g, 3.04 mmol) at 0° C. After stirring at rt for 1 h, 3-amino-5-bromopyridin-2-ol (0.383 g, 2.02 mmol) was added and stirring was continued for 16 h at rt. The reaction mixture was poured into water (50 ml) and extracted with EtOAc (3×50 ml). The combined organic extracts were dried over anhydrous $Na_2SO_4$, filtered and concentrated under reduced pressure. The residue was purified by column chromatography (30% EtOAc in hexane) to give tert-butyl 3-((5-bromo-2-hydroxypyridin-3-yl)carbamoyl)-3-fluoropiperidine-1-carboxylate (0.466 g, 1.12 mmol). LCMS: Method C, 1.944 min, MS: [M-56]: 362.2

Step b.

To a stirred solution of tert-butyl 3-((5-bromo-2-hydroxypyridin-3-yl)carbamoyl)-3-fluoro-piperidine-1-carboxylate (0.450 g, 1.08 mmol) in $CHCl_3$ (12 ml) was added TEA (0.87 g, 8.61 mmol), triphenylphosphine (0.85 g 3.23 mmol) and hexachloroethane (0.625 g 2.64 mmol) at rt under nitrogen and stirred for 18 h. The resulting mixture was poured into water (100 ml) and extracted with DCM (2×100 ml). The combined organic extracts were dried over anhydrous $Na_2SO_4$, filtered and concentrated under reduced pressure. The resulting residue was purified by column chromatography (15% EtOAc in hexane) yielding tert-butyl 3-(6-bromooxazolo [5,4-b] pyridin-2-yl)-3-fluoropiperidine-1-carboxylate (0.240 g, 0.60 mmol). LCMS: Method C, 2.341 min, MS: [M-56]: 344.02

Step c.

To a stirred solution of tert-butyl 3-(6-bromooxazolo [5,4-b] pyridin-2-yl)-3-fluoropiperidine-1-carboxylate (0.200 g, 0.50 mmol) in 1,4-dioxane:water mixture (4:1; 8 ml) was added (3-cyano-phenyl)boronic acid (0.110 g, 0.750 mmol) and $K_2CO_3$ (0.207 g, 1.50 mmol) at rt. The reaction mixture was degassed with nitrogen for 30 min before addition of $PdCl_2(dppf)$ (0.018 g, 0.03 mmol). The resulting reaction mixture was heated at 75° C. for 1 h. The reaction mixture was cooled to rt, poured into water (50 ml) and extracted with EtOAc (2×50 ml). The combined organic extracts were dried over anhydrous $Na_2SO_4$, filtered and concentrated under reduced pressure. The resulting residue was purified by column chromatography (20% EtOAc in hexane) to obtain tert-butyl 3-(6-(3-cyanophenyl) oxazolo [5,4-b] pyridin-2-yl)-3-fluoropiperidine-1-carboxylate (0.205 g, 0.49 mmol). LCMS: Method C, 2.281 min, MS: ES+ 423.4

Steps d, e.

The title compound was synthesised from the intermediate above using a procedure similar to that described for Example 1, steps c, d. LCMS: Method A, 3.836 min, MS: ES+ 348 (M+H+); $^1$H NMR (400 MHz, DMSO-d6) δ ppm: 8.89 (d, J=2.0 Hz, 1H), 8.79 (d, J=2.0 Hz, 1H), 8.36 (s, 1H), 8.19 (d, J=8.0 Hz, 1H), 7.94 (d, J=8.0 Hz, 1H), 7.76 (t, J=8.4 Hz, 1H), 4.04-3.82 (m, 2H), 3.49-3.46 (m, 1H), 3.35-3.25 (m, 1H), 2.50-2.19 (m, 2H), 2.04-1.95 (m, 1H), 1.81-1.78 (m, 1H).

EXAMPLE 29

3-(6-(3-cyanophenyl)oxazolo[4,5-b]pyridin-2-yl)-3-fluoropiperidine-1-carbonitrile

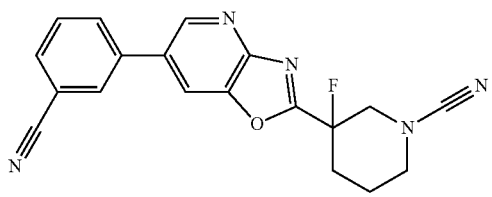 [SMILES: N#Cc1cccc(-c2cnc3nc(C4(F)CCCN(C#N)C4)oc3c2)c1]

The title compound was synthesised using a procedure similar to that described for Example 28, using 2-amino-5-bromo-3-hydroxypyridine (CAS Number 39903-01-0) in step a. LCMS: Method A, 3.646 min, MS: ES+ 348; $^1$H NMR (400 MHz, DMSO-d6) δ ppm: 9.05 (d, J=1.6 Hz, 1H), 8.78 (d, J=2.0 Hz, 1H), 8.34 (s, 1H), 8.21 (d, J=8.0 Hz, 1H), 7.95 (d, J=7.6 Hz, 1H), 7.77 (t, J=8.0 Hz, 1H), 4.01-3.83 (m, 2H), 3.50-3.47 (m, 1H), 3.30-3.26 (m, 1H), 2.50-2.24 (m, 2H), 2.05-1.92 (m, 1H), 1.82-1.79 (m, 1H).

EXAMPLE 30

(R)-4-(2-(1-cyano-3-fluoropiperidin-3-yl)oxazolo[5,4-b]pyridin-6-yl)picolinonitrile

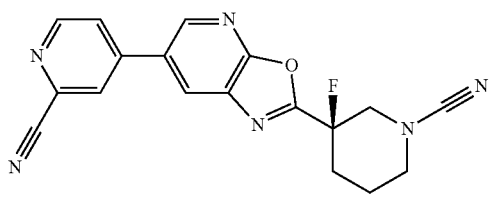 [SMILES: N#Cc1cc(-c2cnc3oc([C@@]4(F)CCCN(C#N)C4)nc3c2)ccn1]

The title compound was synthesised using a procedure similar to that described for Example 28, using 4-(4,4,5,5-tetramethyl-1,3,2-dioxaborolan-2-yl)picolinonitrile (CAS Number 741709-62-6) in step c. LCMS: Method B, 3.513 min, MS: ES+ 349.5; $^1$H NMR (400 MHz, DMSO-d6) δ ppm: 9.06 (d, J=1.2 Hz, 1H), 8.97 (d, J=1.2 Hz, 1H), 8.91 (d, J=4.0 Hz, 1H), 8.65 (s, 1H), 8.29 (d, J=4.0 Hz, 1H), 3.97-3.83 (m, 2H), 3.50-3.45 (m, 1H), 3.30-3.29 (m, 1H), 2.50-2.29 (m, 2H), 2.01-1.98 (m, 1H), 1.82-1.79 (m, 1H).

EXAMPLE 31

(R)-4-(2-(1-cyano-3-fluoropiperidin-3-yl)imidazo[1,2-a]pyridin-7-yl)picolinonitrile

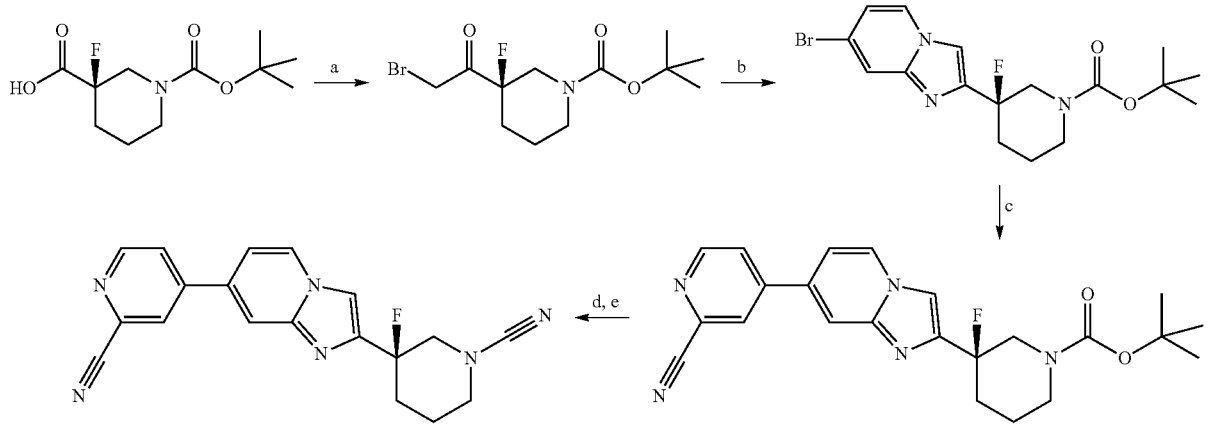

Step a.

To a stirred solution of (R)-1-(tert-butoxycarbonyl)-3-fluoropiperidine-3-carboxylic acid (1.000 g, 4.05 mmol) in DCM (10 ml) was added oxalyl chloride (0.76 ml, 8.91 mmol) and catalytic DMF (0.044 g, 0.61 mmol) at 0° C., warmed to rt and stirred for 30 min. The reaction mass was concentrated under reduced pressure and dissolved in THF:MeCN mixture (1:1; 10 ml). After cooling the solution to 0° C., TMS-diazomethane (0.6M in hexane; 23.5 ml, 14.1 mmol) was added dropwise under nitrogen. The reaction mass was stirred at 0° C. for 2.5 h followed by addition of 48% aqueous HBr (6.71 ml, 39.8 mmol). The reaction was warmed to rt and stirred for a further 10 min. The resulting reaction mixture was poured into water (50 ml) and extracted with EtOAc (2×50 ml). The combined organic extracts were dried over anhydrous Na$_2$SO$_4$, filtered and concentrated under reduced pressure. The residue was purified by column chromatography (6% EtOAc in n-hexane) to give tert-butyl (R)-3-(2-bromoacetyl)-3-fluoropiperidine-1-carboxylate (0.627 g, 1.94 mmol). LCMS: Method C, 1.739 min, MS: ES+ 324.4

Step b.

To a stirred solution of 4-bromopyridin-2-amine (CAS Number 84249-14-9; 0.214 g, 1.24 mmol) in ethanol (3 ml) was added tert-butyl (R)-3-(2-bromoacetyl)-3-fluoro-piperidine-1-carboxylate (0.200 g, 0.62 mmol) at rt and resulting mixture was heated at 100° C. for 5 h. Reaction mixture was concentrated under reduced pressure, crude mass was poured into water (30 ml) and extracted with EtOAc (2×30 ml). The combined organic extracts were dried over anhydrous $Na_2SO_4$, filtered and concentrated under reduced pressure. The resulting residue was purified by column chromatography (28% EtOAc in n-hexane) to obtain tert-butyl (R)-3-(7-bromoimidazo[1,2-a]pyridin-2-yl)-3-fluoro-piperidine-1-carboxylate (0.165 g, 0.42 mmol). LCMS: Method C, 1.775 min, MS: ES+ 398.4

Step c.

To a stirred solution of tert-butyl (R)-3-(7-bromoimidazo[1,2-a]pyridin-2-yl)-3-fluoro-piperidine-1-carboxylate (0.150 g, 0.38 mmol) in DMF:water (4:1; 5 ml) was added 4-(4,4,5,5-tetramethyl-1,3,2-dioxaborolan-2-yl)picolinonitrile (0.129 g, 0.57 mmol) and $NaHCO_3$ (0.095 g, 1.13 mmol) at rt. The reaction mass was degassed for 15 min before addition of $PdCl_2(dppf)$ (0.028 g, 0.04 mmol) and the resulting mixture was heated to 100° C. for 3 h. The reaction mixture was cooled to rt, poured into water (25 ml) and extracted with EtOAc (2×25 ml). The combined organic extracts were dried over anhydrous $Na_2SO_4$, filtered and concentrated under reduced pressure. The residue was purified by column chromatography (100% EtOAc in n-hexane) to provide tert-butyl (R)-3-(7-(2-cyano-pyridin-4-yl)imidazo[1,2-a]pyridin-2-yl)-3-fluoropiperidine-1-carboxylate (0.095 g, 0.23 mmol). LCMS: Method C, 1.719 min, MS: ES+ 422.5

Steps d, e.

The title compound was synthesised from the intermediate above using a procedure similar to that described for Example 1, steps c, d. LCMS: Method B, 3.180 min, MS: ES+ 347.5 (M+H$^+$); $^1$H NMR (400 MHz, DMSO-d6) δ ppm: 8.84 (d, J=5.2 Hz, 1H), 8.31 (d, J=6.8 Hz, 1H), 7.95 (s, 1H), 7.90 (s, 1H), 7.80 (s, 1H), 7.77 (dd, J=5.2 Hz, 1.6 Hz, 1H), 7.13 (dd, J=7.2 Hz, 1.6 Hz, 1H), 3.75-3.53 (m, 3H), 3.21 (t, J=10.8 Hz, 1H), 2.36-2.24 (m, 3H), 1.80-1.76 (m, 1H).

Biological Activity of Compounds of the Invention

Abbreviations:

TAMRA carboxytetramethylrhodamine
PCR polymerase chain reaction
PBS phosphate buffered saline
EDTA ethylenediaminetetraacetic acid
Tris 2-amino-2-(hydroxymethyl)-1,3-propanediol
NP-40 Nonidet P-40, octylphenoxypolyethoxyethanol
BSA bovine serum albumin
PNS peripheral nervous system
BH3 Bcl-2 homology domain 3
PTEN phosphatase and tensin homologue In Vitro USP30 Inhibition Assay USP30 Biochemical Kinetic Assay.

Reactions were performed in duplicate in black 384 well plates (small volume, Greiner 784076) in a final reaction volume of 21 µl. USP30 CD (57-517, #64-0057-050 Ubiquigent) was diluted in reaction buffer (40 mM Tris, pH 7.5, 0.005% Tween 20, 0.5 mg/ml BSA, 5 mM beta-mercaptoethanol) to the equivalent of 0, 0.005, 0.01, 0.05, 0.1 and 0.5 l/well. Buffer was optimised for optimal temperature, pH, reducing agent, salts, time of incubation, and detergent. Reactions were initiated by the addition of 50 nM of TAMRA labelled peptide linked to ubiquitin via an isopeptide bond as fluorescence polarisation substrate. Reactions were incubated at rt and read every 2 min for 120 min. Readings were performed on a Pherastar Plus (BMG Labtech). λ Excitation 540 nm; λ Emission 590 nm.

USP30 Biochemical IC50 Assay

Dilution plates were prepared at 21 times the final concentration (2100 µM for a final concentration of 100 µM) in 50% DMSO in a 96-well polypropylene V-bottom plate (Greiner #651201). A typical 8-point dilution series would be 100, 30, 10, 3, 1, 0.3, 0.1, 0.03 M final. Reactions were performed in duplicate in black 384 well plates (small volume, Greiner 784076) in a final reaction volume of 21 µl. Either 1 µl of 50% DMSO or diluted compound was added to the plate. USP30 was diluted in reaction buffer (40 mM Tris, pH 7.5, 0.005% Tween 20, 0.5 mg/ml BSA, 5 mM beta-mercaptoethanol) to the equivalent of 0.05 µl/well and 10 µl of diluted USP30 was added to the compound. Enzyme and compound were incubated for 30 min at room temp. Reactions were initiated by the addition of 50 nM of TAMRA labelled peptide linked to ubiquitin via an isopeptide bond as fluorescence polarisation substrate. Reactions were read immediately after addition of substrate and following a 2 h incubation at room temperature. Readings were performed on a Pherastar Plus (BMG Labtech). λ Excitation 540 nm; λ Emission 590 nm.

Activity of Exemplary Compounds in USP30 Biochemical IC50 Assay

Ranges:
0.01<A<0.1 µM;
0.1<B<1 µM;
1<C<10 µM;

| Example | IC50 range |
|---------|------------|
| 1 | D |
| 2 | D |
| 3 | D |
| 4 | D |
| 5 | D |
| 6 | C |
| 7 | D |
| 8 | D |
| 9 | A |
| 10 | B |
| 11 | B |
| 12 | C |
| 13 | C |
| 14 | C |
| 15 | B |
| 16 | A |
| 17 | C |
| 18 | B |
| 19 | B |
| 20 | B |
| 21 | C |
| 22 | A |
| 23 | B |
| 24 | B |
| 25 | A |
| 26 | B |
| 27 | B |
| 28 | B |
| 29 | B |
| 30 | B |
| 31 | B |

The invention claimed is:

1. A compound of formula (I):

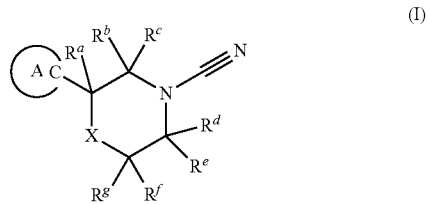

a tautomer thereof, or a pharmaceutically acceptable salt of said compound or tautomer, wherein:

X is $C(R^i)(R^j)$;

$R^a$ is selected from hydrogen, fluoro, $C_1$-$C_3$ alkyl, and $C_1$-$C_3$ alkoxy;

$R^c$, $R^e$, $R^g$ and $R^j$ are hydrogen;

$R^b$, $R^d$, $R^f$ and $R^i$ is are each independently selected from hydrogen and $C_1$-$C_3$ alkyl, which is optionally substituted by $C_1$-$C_6$ alkoxy, halo, hydroxyl, thiol, cyano, amino or nitro;

ring A is a 5 to 6-membered monocyclic heteroaryl ring, which comprises 1 to 4 heteroatoms independently selected from nitrogen, oxygen and sulfur, at least one of which is nitrogen, and is substituted with 1 to 4 $Q^1(R^1)_n$ groups, which may be the same or different;

n is 0 or 1;

when n is 0, $Q^1$ is $Q^{1a}$;

when n is 1, $Q^1$ is $Q^{1b}$;

$Q^{1a}$ is selected from halo, cyano, hydroxyl, methyl, ethyl, methoxy, and ethoxy;

$Q^{1b}$ is a covalent bond or oxygen;

$R^1$ is selected from phenyl and 5 to 6-membered monocyclic heteroaryl, which comprises 1 to 3 heteroatoms independently selected from nitrogen, oxygen and sulfur; wherein $R^1$ is unsubstituted or substituted with 1 to 6 substituents, each independently selected from halo, cyano, oxo, nitro, hydroxyl, $C_1$-$C_6$ alkyl, $C_1$-$C_6$ alkoxy, $C_2$-$C_6$ alkenyl, $C_2$-$C_6$ alkynyl, $R^{11}$, and O—$R^{11}$; and $R^{11}$ is selected from phenyl and 5 to 6-membered monocyclic heteroaryl, each of which may be unsubstituted, or substituted with 1 to 5 substituents each independently selected from halo, cyano, hydroxyl, methyl, ethyl, methoxy, and ethoxy.

2. The compound according to claim 1, wherein the heteroaryl ring of group A is selected from pyridinyl, pyrazinyl, pyrimidinyl, pyridazinyl, furanyl, thiophenyl, pyrrolyl, oxazolyl, thiazolyl, pyrazolyl, triazolyl, tetrazolyl, furazanyl, imidazolyl, isothiazolyl, isoxazolyl, oxadiazolyl, tetrazolyl, thiadiazolyl, pyrazinyl, triazinyl, dihydropyridinyl, and tetrahydropyrazinyl.

3. The compound according to claim 2, wherein the heteroaryl ring of group A is selected from triazolyl, oxazolyl, and oxadiazolyl.

4. The compound according to claim 1, wherein $R^a$ is selected from hydrogen, fluoro, methyl, ethyl, methoxy, and ethoxy.

5. The compound according to claim 4, wherein $R^b$, $R^d$, $R^f$, and $R^i$ are each independently selected from hydrogen, methyl, and ethyl.

6. The compound according to claim 1, wherein $R^1$ is unsubstituted, or substituted with 1 to 5 substituents, each independently selected from halo, cyano, hydroxyl, methyl, ethyl, methoxy and ethoxy.

7. A compound of formula (I), which is selected from:

3-(4-(2-phenoxyphenyl)oxazol-2-yl)piperidine-1-carbonitrile;

3-(4-([1,1'-biphenyl]-3-yl)oxazol-2-yl)piperidine-1-carbonitrile;

(R)-3-(5-([1,1'-biphenyl]-3-yl)-1,3,4-oxadiazol-2-yl)-3-fluoropiperidine-1-carbonitrile;

3-(5-([1,1'-biphenyl]-4-yl)-1,3,4-oxadiazol-2-yl)-3-fluoropiperidine-1-carbonitrile;

(R)-4-(5-(1-cyano-3-fluoropiperidin-3-yl)-1,3,4-oxadiazol-2-yl)-[2,4'-bipyridine]-2'-carbonitrile;

(R)-4-(5-(1-cyano-3-fluoropiperidin-3-yl)-1,3,4-oxadiazol-2-yl)picolinonitrile; and (R)-2'-(5-(1-cyano-3-fluoropiperidin-3-yl)-1,3,4-oxadiazol-2-yl)-[4,4'-bipyridine]-2-carbonitrile;

a tautomer thereof, or a pharmaceutically acceptable salt of said compound or tautomer.

8. A method of inhibiting USP30 in a mammal in need thereof, comprising administering to said mammal a therapeutically effective amount of a compound as defined in claim 1, a tautomer thereof, or a pharmaceutically acceptable salt of said compound or tautomer.

9. A method of inhibiting UPS30 in a mammal in need thereof, wherein the mammal is suffering from condition involving mitochondrial dysfunction or cancer, comprising administering to said mammal a therapeutically effective amount of a compound as defined in claim 1, a tautomer thereof, or a pharmaceutically acceptable salt of said compound or tautomer.

10. The method according to claim 9, wherein the disorder or condition involving mitochondrial dysfunction is selected from a CNS disorder; neurodegenerative disease; multiple sclerosis; mitochondrial encephalopathy, lactic acidosis and stroke-like episodes syndrome; Leber's hereditary optic neuropathy; cancer; neuropathy; ataxia; retinitis pigmentosa; maternally inherited Leigh syndrome; Danon disease; metabolic disorders; heart failure; ischemic heart disease leading to myocardial infarction; psychiatric diseases; schizophrenia; multiple sulfatase deficiency; mucolipidosis II; mucolipidosis III; mucolipidosis IV; GM1-gangliosidosis; neuronal ceroid-lipofuscinoses; Alpers disease; Barth syndrome; Beta-oxidation defects; carnitine-acyl-carnitine deficiency; carnitine deficiency; creatine deficiency syndromes; co-enzyme Q10 deficiency; complex I deficiency; complex II deficiency; complex III deficiency; complex IV deficiency; complex V deficiency; COX deficiency; chronic progressive external ophthalmoplegia syndrome; CPT I deficiency; CPT II deficiency; glutaric aciduria type II; Kearns-Sayre syndrome; lactic acidosis; long-chain acyl-CoA dehydrogenase deficiency; Leigh disease or syndrome; lethal infantile cardiomyopathy; Luft disease; glutaric aciduria type II; medium-chain acyl-CoA dehydrogenase deficiency; myoclonic epilepsy and ragged-red fiber syndrome; mitochondrial cytopathy; mitochondrial recessive ataxia syndrome; mitochondrial DNA depletion syndrome; myoneurogastointestinal disorder and encephalopathy; Pearson syndrome; pyruvate dehydrogenase deficiency; pyruvate carboxylase deficiency; POLG mutations; medium/short-chain 3-hydroxyacyl-CoA dehydrogenase deficiency; very long-chain acyl-CoA dehydrogenase deficiency; and age-dependent decline in cognitive function and muscle strength.

11. The method according to claim 10, wherein the neurodegenerative disease is selected from Parkinson's disease, Alzheimer's disease, amyotrophic lateral sclerosis, Huntington's disease, ischemia, stroke, dementia with Lewy bodies, frontotemporal dementia; and Parkinson's disease related to mutations in a synuclein, parkin and PINK1, autosomal recessive juvenile Parkinson's disease where parkin is mutated.

12. The method according to claim 9, wherein the cancer is selected from breast, ovarian, prostate, lung, kidney, gastric, colon, testicular, head and neck, pancreas, brain, melanoma, bone, cancers of tissue organs, cancers of the blood cells, lymphoma, leukaemia, multiple myeloma, colorectal cancer and non-small cell lung carcinoma.

13. A pharmaceutical composition comprising a compound according to claim 1 together with one or more pharmaceutically acceptable excipients.

14. A pharmaceutical composition, comprising a therapeutically effective amount of a compound selected from the group consisting of:

2-(3-([1,1'-biphenyl]-3-yl)-1H-1,2,4-triazol-5-yl)morpholine-4-carbonitrile;
3-(4-(2-phenoxyphenyl)oxazol-2-yl)piperidine-1-carbonitrile;
3-(4-([1,1'-biphenyl]-3-yl)oxazol-2-yl)piperidine-1-carbonitrile;
(R)-3-(5-([1,1'-biphenyl]-3-yl)-1,3,4-oxadiazol-2-yl)-3-fluoropiperidine-1-carbonitrile;
3-(5-([1,1'-biphenyl]-4-yl)-1,3,4-oxadiazol-2-yl)-3-fluoropiperidine-1-carbonitrile;
(R)-4-(5-(1-cyano-3-fluoropiperidin-3-yl)-1,3,4-oxadiazol-2-yl)-[2,4'-bipyridine]-2'-carbonitrile;
(R)-4-(5-(1-cyano-3-fluoropiperidin-3-yl)-1,3,4-oxadiazol-2-yl)picolinonitrile; and
(R)-2'-(5-(1-cyano-3-fluoropiperidin-3-yl)-1,3,4-oxadiazol-2-yl)-[4,4'-bipyridine]-2-carbonitrile;
or a tautomer thereof, or a pharmaceutically acceptable salt of said compound or tautomer, together with one or more pharmaceutically acceptable excipients.

15. The method according to claim 10, wherein said metabolic disorder is diabetes or diabetic nephropathy.

16. The method according to claim 9, wherein said cancer is a cancer where apoptotic pathways are dysregulated or a cancer where proteins of the BCL-2 family are mutated, or over or under expressed.

* * * * *

UNITED STATES PATENT AND TRADEMARK OFFICE
CERTIFICATE OF CORRECTION

PATENT NO. : 10,927,110 B2
APPLICATION NO. : 16/336363
DATED : February 23, 2021
INVENTOR(S) : Stockley et al.

It is certified that error appears in the above-identified patent and that said Letters Patent is hereby corrected as shown below:

In the Claims

At Column 74, Line 8, "UPS30" should be printed as "USP30."

At Column 74, Line 53, "a" should be printed as "α ."

Signed and Sealed this
Third Day of May, 2022

Katherine Kelly Vidal
*Director of the United States Patent and Trademark Office*